US007083794B2

(12) United States Patent
Curtiss, III et al.

(10) Patent No.: US 7,083,794 B2
(45) Date of Patent: *Aug. 1, 2006

(54) RECOMBINANT VACCINES COMPRISING IMMUNOGENIC ATTENUATED BACTERIA HAVING RPOS POSITIVE PHENOTYPE

(75) Inventors: Roy Curtiss, III, St. Louis, MO (US); Cheryl A. Nickerson, River Ridge, LA (US)

(73) Assignee: Washington University, St. Louis, MO (US)

( * ) Notice: Subject to any disclaimer, the term of this patent is extended or adjusted under 35 U.S.C. 154(b) by 576 days.

This patent is subject to a terminal disclaimer.

(21) Appl. No.: 10/138,239

(22) Filed: May 3, 2002

(65) Prior Publication Data

US 2003/0031683 A1 Feb. 13, 2003

Related U.S. Application Data

(63) Continuation of application No. 09/314,062, filed on May 18, 1999, now Pat. No. 6,383,496, which is a continuation-in-part of application No. 08/970,789, filed on Nov. 14, 1997, now Pat. No. 6,024,961.

(51) Int. Cl.
  A61K 39/02 (2006.01)
  A61K 39/112 (2006.01)
  C12N 15/74 (2006.01)
  C12N 1/21 (2006.01)

(52) U.S. Cl. ............... 424/200.1; 424/93.1; 424/258.1; 435/471; 435/252.3; 435/252.8; 435/879

(58) Field of Classification Search ............ 424/200.1, 424/93.2, 258.1; 435/471, 252.3, 252.8, 435/857, 879
See application file for complete search history.

(56) References Cited

U.S. PATENT DOCUMENTS

| 4,837,151 | A |   | 6/1989 | Stocker |           |
|-----------|---|---|--------|---------|-----------|
| 5,294,441 | A | * | 3/1994 | Curtiss, III | ............ 424/200.1 |
| 5,387,744 | A |   | 2/1995 | Curtiss, III et al. |   |
| 5,656,488 | A |   | 8/1997 | Curtiss, III et al. |   |
| 5,672,345 | A |   | 9/1997 | Curtiss, III |      |
| 6,024,961 | A | * | 2/2000 | Curtiss et al. | ............ 424/200.1 |
| 6,383,496 | B1| * | 5/2002 | Curtiss et al. | ............ 424/200.1 |

FOREIGN PATENT DOCUMENTS

| EP | 0 315 682   | 12/1993 |
|----|-------------|---------|
| WO | WO 92/09684 | 6/1992  |
| WO | WO 94/24291 | 10/1994 |
| WO | WO 94/27634 | 12/1994 |

OTHER PUBLICATIONS

Baumler et al (PNAS USA 93:279-282, 1996).*
Bäumler et al., The *lpf* fimbrial operon mediates adhesion of *Salmonella typhimurium* to murine Peyer's patches, *Proc. Natl. Acad. Sci., USA 93*:279-283 (1996).
Carter and Collins, The Route of Enteric Infection in Normal Mice, *J. Exp. Med. 139*:1189-1203, (1974).
Coynault et al., Virulence and vaccine potential of *Salmonella typhimurium* mutants deficient in the expression of the RpoS ($\sigma^2$) regulon, *Mol. Microbiol. 22*:149-160 (1996).
Curtiss et al., Selective Delivery of Antigens by Recombinant Bacteria, *Current Topics in Microbiology and Immunology 146*:35-49 (1989).
Curtiss et al., Avirulent *Salmonella typhimurium* Δcya Δcrp oral vaccine strains expressing a streptococcal colonization and virulence antigen, *Vaccine 6*:155-160 (1988).
Curtiss, Attenuated *Salmonella* Strains as Live Vectors for the Expression of Foreign Antigens, *New Generation Vaccines*, Woodrow and Levine, Eds., Marcel Dekker, Inc., New York, 1990, pp. 161-188.
Curtiss et al., Strategies for the Use of Live Recombinant Avirulent Bacterial Vaccines for Mucosal Immunization, *Essentials of Mucosal Immunology*, Kagnoff and Kiyono, Eds., Academic Press, San Diego, 1996, pp. 499-511.
Doggett et al., Attenuated *Salmonella* as Vectors for Oral Immunization, *Mucosal Vaccines*, Kiyono et al., Eds. Academic Press, San Diego, 1996 pp. 105-118.
Fang et al., The Alternative σ factor KatF (RpoS) regulates *Salmonella* virulence, *Proc. Natl. Acad. Sci. 89*:11978-11982 (1992).
Forrest, Chapter 2, Clinical Evaluation of Attenuated *Salmonella typhi* Vaccines in Human subjects, in CRC Press, Inc., 59-79 (1994).
Gonzales et al., *Journal of Infectious Diseases 169*:927-931 (1994).
Gulig et al., Plasmid-associated Virulence of *Salmonella typhimurium*, *Infect. Immun. 55*:2891-2901 (1987).
Gulig et al., Cloning and Transposon Insertion Mutagenesis of Virulence Genes of the 100-Kilobase Plasmid of *Salmonella typhimurium*, *Infect. Immun. 56*:3262-3271 (1987).
Hackett et al., The Colonization of Peyer's Patches by a Strain of *Salmonella typhimurium* Cured of the Cryptic Plasmid, *J. Infect. Dis. 153*:1119-1125 (1986).
Herr, *Am. J. Reprod. Immunol.* (*Denmark*) *35*(3):p. 184-9 (1996) (Abstract only Cited).

(Continued)

*Primary Examiner*—Mary E. Mosher
(74) *Attorney, Agent, or Firm*—Thompson Coburn, LLP

(57) ABSTRACT

Attenuated immunogenic bacteria having an RpoS$^+$ phenotype, in particular, *Salmonella enterica* serotype *Typhi* having an RpoS$^+$ phenotype and methods therefor are disclosed. The *Salmonella* have in addition to an RpoS$^+$ phenotype, an inactivating mutation in one or more genes which render the microbe attenuated, and a recombinant gene capable of expressing a desired protein. The *Salmonella* are attenuated and have high immunogenicity so that they can be used in vaccines and as delivery vehicles for genes and gene products. Also disclosed are methods for preparing the vaccine delivery vehicles.

29 Claims, 16 Drawing Sheets

OTHER PUBLICATIONS

Kleckner et al., Genetic Engineering in Vivo Using Translocatable Drug-resistance Elements, *J. Mol. Biol.* 116:125-159 (1977).

Kowarz et al., The *Salmonella typhimurium* katF (rpoS) Gene: Cloning, Nucleotide Sequence, and Regulation of spvR and spvABCD Virulence Plasmid Genes, *J. Bacteriol.* 176:6852-6860 (1994).

Lange et al., Identification of a central regulator of stationary-phase gene expression in *Escherichia coli*, *Mol. Microbiol.* 5:49-59 (1991).

Levine et al., Attenuated, Streptomycin-Dependent *Salmonella typhi* Oral Vaccine: Potential Deleterious Effects of Lyophilization, *J. Infect. Dis.* 133:424-429 (1976).

Levine et al., New and Improved Vaccines Against Typhoid Fever, *New Generation Vaccines* 269-287 (1990).

Loewen et al., The role of the Sigma Factor $\sigma^2$ (KatF) in Facterial Global Regulation, *Annu. Rev. Microbiol.* 48 53-80 (1994).

Nardelli-Haefliger et al., Oral and Rectal Immunization of Adult Female Volunteers with a Recombinant Attenuated *Salmonella typhi* Vaccine Strain, *Infect. Immun.* 64:5219-5224 (1996).

Nickerson et al., *Abstracts of the 96th General Meeting of the American Society for Microbiology*, B-141:179 (1996).

Nickerson and Curtiss, Role of Sigma Factor RpoS in Initial Stages of *Salmonella typhimurium* Infection, *Infect. and Immun.* 65:1814-1823 (1997).

Norel et al., The putative sigma factor KatF (RpoS) is required for the transcript of the *Salmonella typhimurium* virulence gene spuB in *Escherichia coli*, *FEMS Microbiol. Let.* 99:271-276 (1992).

Reitman, Infectivity and Antigenicity of Streptomycin-Dependent *Salmonella typhosa*, *J. Infect. Dis.* 117:101-107 (1967).

Robbe-Saule et al., The live oral typhoid vaccine Ty21a is a rpoS mutant and is susceptible to various environmental stresses, *FEMS Microbiol. Let.* 126:171-176 (1995).

Schodel et al., Hybrid Hepatitis B Virus Core Antigen as a Vaccine Carrier Moiety, *Novel Strategies in Designs and Production of Vaccines*, S. Cohen and A. Shafferman, eds. Plenum Press, New York, pp. 15-21 (1995).

Tacket et al., Comparison of the Safety and Immunogenicity of ΔaroC ΔaroD and Δcya Δcrp *Salmonella typhi* Strains in Adult Volunteers, *Infect. Immun.* 60:536-541 (1992).

Vrtale et al., *Int. Arch Allergy Immunol.* (*Switzerland*) 107(1-3):p. 290-294 (1995) (Abstract Only Cited).

Wilmes-Riesenberg et al., An Altered rpoS Allele Contributes to the Avirulence of *Salmonella typhimurium* LT2, *Infect. Immun.* 65:203-210 (1997).

\* cited by examiner

RECOMBINANT VACCINES COMPRISING IMMUNOGENIC ATTENUATED BACTERIA HAVING RPOS POSITIVE PHENOTYPE

RELATED APPLICATIONS

This application is a continuation of patent application Ser. No. 09/314,062, filed May 18, 1999, now issued as U.S. Pat. No. 6,383,496, which is a continuation-in-part of patent application Ser. No. 08/970,789 filed Nov. 14, 1997, now issued as U.S. Pat. No. 6,024,961 on Feb. 15, 2000.

BACKGROUND OF THE INVENTION (1) Field of the Invention

This invention relates generally to attenuated microbes and, more particularly, to novel attenuated bacteria having an RpoS$^+$ phenotype for use as vaccines and delivery vehicles for genes and gene products and to methods for their preparation. This invention is particularly applicable to *Salmonella* such as *Salmonella enterica* serotype *Typhi* (also referred to as *Salmonella typhi*).

(2) Description of the Related Art

Live attenuated *Salmonella* strains can serve as delivery vehicles for recombinant antigens or other proteins. As antigen carriers, the recombinant *Salmonella* have been shown to be useful in live vaccines (For review see Curtiss et al. in *Essentials of Musocal Immunology*, Kagnoff and Kiyono, Eds., Academic Press, San Diego, 1996, pp. 599–611; Doggett and Brown, in *Mucosal Vaccines*, Kiyono et al., Eds., Academic Press, San Diego, 1996 pp 105–118; see also Hopkins et al. *Infect Immun.* 63:3279–3286, 1995; Srinavasin et al *Vaccines* 95, R. N. Chanock et al., Eds., Cold Spring Harbor Laboratory Press, Plainview, N.Y., p 273–280, 1995).

Ideally, live attenuated vaccine strains should possess a balance between the two properties of attenuation and immunogenicity. Such vaccine strains would not cause any disease or impair normal host physiology or growth, thus being attenuated, and at the same time be able to colonize the intestine and gut associated lymphoid tissue upon oral administration or other lymphoid organs upon administration by some other route so as to be immunogenic. As a practical matter, however, such an ideal balance has not been achieved (Curtiss, in *New Generation Vaccines* Woodrow and Levine, Eds., Marcel Dekker, Inc., New York, 1990, pp. 161–188). This may be a result of the almost exclusive focusing of efforts in *Salmonella* vaccine development on improving the attenuation component of strains rather than on producing strains with high immunogenicity.

Work directed toward achieving attenuation in microbes for use in vaccines has utilized attenuating mutations in biosynthetic genes, regulatory genes and/or genes involved in virulence. (See Doggett and Brown, supra). One such regulatory gene which has been mutated as a means for achieving attenuation has been the rpoS gene. The rpoS gene encodes an alternative sigma factor, RpoS, which is known to regulate the stationary phase expression of over 30 genes (for review, see Loewen and Hengge-Aronis, *Annu Rev Microbiol* 48:53–80, 1994). The rpoS gene has been shown to contribute to the virulence of *Salmonella enterica* serotype *Typhimurium* (also referred to as *Salmonella typhimurium*) in mice by RpoS regulation of chromosomal as well as plasmid-borne genes (Fang et al., *Proc Natl Acad Sci* 89:11978–11982, 1992; Norel et al., *FEBS Microbiol Lett* 99:271–276, 1992; Kowarz et al., *J Bacteriol* 176:6852–6860, 1994). Similarly, RpoS is thought to contribute to the virulence of *Salmonella typhi* in humans by an action on chromosomal gene determinants of virulence, inasmuch as these microbes do not possess the virulence plasmid present in *S. typhimurium* (Robbe-Saule et al., *FEMS Microbiol Let* 126:171–176, 1995; Coynault et al., *Mol Microbiol* 22:149–160, 1996). Mutant rpoS *S. typhimurium* strains have been shown to be attenuated (Fang et al, supra) and capable of eliciting protective immunity in mice (Nickerson and Curtiss, *Abstracts of the 96th General Meeting of the American Society for Microbiology* B-141:179, 1996; Coynault et al., *Mol Microbiol* 22:149–160, 1996). As a result, it has been suggested that rpoS mutants may be attractive candidates for the development of vaccines (Nickerson and Curtiss, supra).

Attenuated strains of *Salmonella typhi* have been used as human vaccines against typhoid fever as well as against heterologous antigens when used as recombinant antigen delivery vehicles (Forrest, in CRC Press Inc., 1994, pp. 59–80; Levine et al, in *New Generation Vaccines* Woodrow and Levine, Eds., Marcel Dekker, Inc., New York, 1990, pp. 269–287). These vaccines based upon *Typhi* strains have almost exclusively been derived from the Ty2 strain, in particular, Ty21a, which contains a galE mutation along with other mutations. Ty2 and its Ty21a derivative vaccine strain have been shown to be rpoS mutants and this mutation may account, at least in part, for the attenuation seen with Ty21a and with other vaccine strains derived from Ty2 presumably by the down regulation of chromosomal virulence genes controlled by the rpoS gene product. The Ty21a vaccine is typical of vaccines derived from Ty2 in that although being attenuated, the Ty21a vaccine has proven to have low vaccine efficacy, requiring three high doses of approximately $10^{10}$ cfu to induce protective immunity in approximately two-thirds of the vaccinated individuals. (Forrest, supra). Thus, there remains a continuing need for *Salmonella typhi* strains which exhibit not only low virulence, but, also high immunogenicity for use in vaccines suitable for the delivery of a desired gene product to a host.

Other strains of *S. typhi* have been reported which may, however, have a functional rpoS gene although this was not appreciated at the time of the report. For example, human vaccines have been reported based upon the 27V and ISP1820 strains (Reitman, *J Infect Dis* 117:101–107, 1967; Levine et al., *J Infect Dis* 133:424–429, 1976; Tacket et al., *Infect Immun* 60:536–541, 1992). Neither of these strains contained a recombinant gene nor were they used to deliver a recombinant gene in a vaccine composition.

In a report of recombinant rpoS$^+$ *S. typhi*, Coynault et al. disclosed the construction of a Ty2 derivative containing a recombinant rpoS gene which gave the microbe an RpoS$^+$ phenotype. However, this Ty2 derivative was used only in a laboratory study and no additional recombinant gene was incorporated nor was there any teaching of the use of this derivative in a vaccine composition.

Finally, the *S. typhi* strains ISP1820 and ISP1822 (U.S. Pat. Nos. 5,387,744 and 5,294,441 and PCT application WO/9424291) and the *S. typhi* strain 531Ty (U.S. Pat. No. 4,837,151) have been used to construct derivative vaccine strains. Although the studies reported herein show ISP1820, ISP1822 and 531Ty to be RpoS$^+$, this was not known at the time of these earlier publications. Furthermore, none of these references recognized the importance of the presence of a functional rpoS gene in achieving a high immunogenicity in a vaccine preparation. As a result, these references did not disclose the selection of vaccine strains based upon the presence of an RpoS$^+$ phenotype.

All references cited in this specification either supra or infra are hereby incorporated by reference. The discussion of the references herein is intended to summarize the assertions made by their authors and no admission is made as to the accuracy or pertinency of the cited references or that any reference is material to patentability.

SUMMARY OF THE INVENTION

In accordance with the present invention, the inventors herein have succeeded in discovering the critical importance of a functional rpoS gene in *Salmonella* vaccine strains in that the presence of a functional rpoS gene and an RpoS$^+$ phenotype confers upon the *Salmonella* the property of high immunogenicity. As a result, when the RpoS$^+$ phenotype is present with one or more inactivating mutations other than a mutation in an rpoS gene, which render the microbe attenuated, a new and advantageous balance of attenuation and high immunogenicity is achieved. This invention is particularly applicable to *S. typhi* based vaccines, however, it is also applicable to other *Salmonella* such as *S. paratyphi* A, B and C as well as to other serotypes of *S. enterica* such as *Typhimurium, Enteritidis, Dublin* and *Choleraesuis.* The invention is also applicable to other bacteria having an rpoS gene, or functional equivalent thereof, that can colonize human tissues, including *Shigella, E. coli,* and hybrids between such bacteria, such as *Salmonella-Shigella* hybrids, *Salmonella-E. coli* hybrids or *Shigell-E. coli* hybrids.

In one embodiment of the present invention, a method is provided for delivery of a desired gene product to a human. The method comprises selecting a strain of bacteria such as *S. typhi* on the basis of the strain having (i) an $RpoS^+$ phenotype, (ii) one or more inactivating mutations which render the strain attenuated, and (iii) a recombinant gene encoding the gene product. The selecting step with respect to $RpoS^+$ phenotype can involve, in whole or in part, testing the strain to determine its RpoS phenotype. The strain thus selected is then administered to the human. The one or more inactivating mutations which render the strain attenuated can involve a mutation in one gene or a mutation in each of two or more genes.

The $RpoS^+$ phenotypic activities of the *Salmonella* or other bacteria can be produced by a chromosomal rpoS gene and/or by a recombinant gene introduced into the strain. Thus, in another embodiment, the method comprises administering to a human a live attenuated strain of bacteria having (a) an $RpoS^+$ phenotype, (b) a recombinant $rpoS^+$ gene, (c) one or more inactivating mutations which render said microbe attenuated and (d) a second recombinant gene encoding the desired product. By recombinant $rpoS^+$ gene or wild-type rpoS gene it is meant that the rpoS gene is capable of producing a functional rpoS gene product. The term recombinant $rpoS^+$ gene is intended to refer to an rpoS gene introduced into a microbe by human intervention and to exclude an rpoS gene transferred from and by a wild-type microbe using a natural means of gene transfer such as conjugation, transduction or transformation, without aid of human intervention.

The attenuated microbes of the present invention contain at least one recombinant gene capable of expressing a desired gene product, which allows their use as carriers or delivery vehicles of the gene product to humans. Examples of gene products deliverable by the microbes of the invention include but are not limited to: antigens, which can be from a human pathogen, or, for use in autoimmune applications, from the human itself, such as, for example, a gamete-specific antigen; enzymes that can synthesize antigens such as polysaccharides, lipoproteins, glycoproteins, and glycolipids; allergens of the human; immunoregulatory molecules; hormones; and pharmacologically active polypeptides. By delivery of the desired gene product it is meant that either the gene product or the polynucleotide, i.e. nucleic acid, either DNA or RNA, encoding the product is delivered to the human. In embodiments in which the attenuated bacteria contains a recombinant rpoS gene, the desired gene product is encoded by a second recombinant gene.

In another embodiment, the present invention provides a method for producing a strain of carrier microbes for delivery of a desired gene product to a human. The method comprises (1) selecting for a strain of *S. typhi* or other bacteria having an $RpoS^+$ phenotype; (2) producing one or more inactivating mutations in the $RpoS^+$ strain to render the strain attenuated; and (3) introducing into the strain a recombinant gene encoding a desired gene product. The selecting step can involve, in whole or in part, testing the strain to determine its RpoS phenotype. Steps 1–3 can be performed in any order.

In a further embodiment, the present invention involves another method for producing carrier microbes for delivery of a desired gene product to a human. The method comprises generating a live attenuated strain of *S. typhi* or other bacteria having (a) an $RpoS^+$ phenotype, (b) a recombinant $rpoS^+$ gene, (c) one or more inactivating mutations which render said microbe attenuated and (d) a second recombinant gene encoding the desired product.

Another embodiment of the present invention provides a carrier microbe for the delivery of a desired gene product to a human. The microbe comprises a live attenuated strain of *S. typhi* or other bacteria having (a) an $RpoS^+$ phenotype, (b) a recombinant $rpoS^+$ gene, (c) one or more inactivating mutations which render said microbe attenuated and (d) a second recombinant gene encoding the desired product.

In another embodiment a vaccine is provided for immunization of a human. The vaccine comprises a live attenuated strain of *S. typhi* or other bacteria having (a) an $RpoS^+$ phenotype, (b) a recombinant $rpoS^+$ gene, (c) one or more inactivating mutations which render said microbe attenuated and (d) a second recombinant gene encoding the desired product.

The present invention also provides in another embodiment, a genetically engineered cell. By genetically engineered cell reference is made to a cell in which the DNA has been manipulated in vitro by human intervention, for example, by gene splicing, to generate a new combination of genes, to place a given gene or genes under the control of a different regulatory system, to introduce specific mutations into the DNA molecule and the like. The generation of the genetically engineered cells can employ any combination of molecular genetic and classical microbial genetic means to effect construction of the genetically engineered cell.

The genetically engineered cell comprises a live attenuated strain of *S. typhi* or other bacteria having (a) an $RpoS^+$ phenotype, (b) a recombinant $rpoS^+$ gene, (c) one or more inactivating mutations which render said microbe attenuated and (d) a second recombinant gene encoding the desired product. A method is also provided for the preparation of a vaccine comprising mixing the genetically engineered cells with a pharmaceutically acceptable formulation suitable for administration to a human.

The present invention also provides a genetically engineered bacteria, in particular *S. typhi,* containing a recombinant virulence gene that is regulated by RpoS, or its functional equivalent, in wild-type bacteria and a method for using the genetically engineered bacteria for the delivery of a desired gene product to a human. The recombinant virulence gene is capable of expressing a gene product that facilitates invasion and colonization of any of the gut associated lymphoid tissues (GALT), nasal associated lymphoid tissue (NALT) or the bronchial associated lymphoid tissue (BALT) and the like which can collectively be called the mucosal associated lymphoid tissue (MALT). The genetically engineered *S. typhi* or other bacteria can be further characterized as having one or more inactivating mutations which render the microbe attenuated as well as a second recombinant gene encoding the desired product.

In still another embodiment, the present invention provides a method for assessing the RpoS phenotype as an indication of the immunogenicity of a bacteria strain, and in particular, of a *Salmonella*. It is believed that many bacterial strains propagated and maintained under laboratory conditions accumulate rpoS mutations. Thus, it would be useful to provide a method for assessing the RpoS phenotype of a *Salmonella* or other bacteria, particularly for a strain being developed for use in a vaccine. The method comprises determining the RpoS phenotype of the bacteria by assessing characteristics of the microbe regulated by RpoS. An increased immunogenicity is indicated by the presence of an $RpoS^+$ phenotype compared to the immunogenicity of an isogenic strain having an $RpoS^-$ phenotype. The isogenic $RpoS^-$ strain does not exhibit an $RpoS^+$ phenotype, but otherwise has the same genetic background as the test strain.

As noted above, the delivery of a polynucleotide encoding the desired gene product to a human is within the scope of the methods and compositions of the present invention. Moreover, each of the embodiments above involving methods and compositions based upon microbes having an $RpoS^+$ phenotype are further contemplated to include methods and compositions for the delivery of a gene or portion thereof to the cells of a human. The gene or portion thereof can comprise a eukaryotic expression cassette that contains the genetic information, either DNA or RNA, that is intended to be delivered to cells of the human.

Thus, in one embodiment of the present invention provides methods for delivery of a gene or portion thereof to the cells of a human. One such method comprises selecting a strain of bacteria such as *S. typhi* on the basis of the strain having (i) an $RpoS^+$ phenotype, (ii) one or more inactivating mutations which render the strain attenuated, and (iii) the gene or portion thereof. The gene or portion thereof can be within a eukaryotic expression cassette. The selecting step with respect to $RpoS^+$ phenotype can involve, in whole or in part, testing the strain to determine its RpoS phenotype. The method can also comprise delivering to cells of a human, a live attenuated strain of bacteria having (a) an $RpoS^+$ phenotype, (b) a recombinant $rpoS^+$ gene, (c) one or more inactivating mutations which render said microbe attenuated and (d) the gene or portion thereof. The gene or portion thereof can be within a eukaryotic expression cassette.

The present invention also provides methods for producing a strain of carrier microbes for delivery of a desired gene or portion thereof to a cell of a human. One such method can comprise (1) selecting for a strain of *S. typhi* or other bacteria having an $RpoS^+$ phenotype; (2) producing one or more inactivating mutations in the $RpoS^+$ strain to render the strain attenuated; and (3) introducing into the strain the gene or portion thereof. The gene or portion thereof can be within a eukaryotic expression cassette. The selecting step can involve, in whole or in part, testing the strain to determine its RpoS phenotype and the steps can be performed in any order. The method can also comprise generating a live attenuated strain of *S. typhi* or other bacteria having (a) an $RpoS^+$ phenotype, (b) a recombinant $rpoS^+$ gene, (c) one or more inactivating mutations which render said microbe attenuated and (d) the desired gene or portion thereof. The gene or portion thereof can be within a eukaryotic expression cassette.

The bacteria that can be used for delivery of a gene or portion thereof can be an attenuated *Salmonella*, *E. coli* or *Shigella* or *Salmonella-Shigella* hybrid, *Salmonella-E. coli* hybrid or *Shigella-E. coli* hybrid so long as the attenuated bacteria releases the nucleic acid within the target host cell.

Among the several advantages achieved by the present invention, therefore, may be noted the provision of a carrier microbe which is capable of colonizing and delivering a desired gene product or a desired polynucleotide to the gut associated lymphoid tissue if administered orally, to the nasal associated lymphoid tissue if administered intranasally and to other lymphoid organs if administered by other routes; the provision of an efficient and inexpensive method for delivery of a nucleic acid molecule to human cells based upon the use of $RpoS^+$ carrier bacteria cells that release the nucleic acid molecule; the provision of vaccine preparations which are highly immunogenic along with being attenuated; the provision of methods of delivering a desired gene product or polynucleotide to an individual by administering the carrier microbe so as to elicit an immune response; the provision of methods of preparing $RpoS^+$ carrier microbes and vaccines wherein the vaccines are not only attenuated but also have high immunogenicity; and the provision of methods for assessing the immunogenicity of a *Salmonella* or other bacteria by determining its RpoS phenotype.

BRIEF DESCRIPTION OF THE DRAWINGS

FIG. 1 illustrates the time course of survival within J774 murine macrophage-like cells of an $rpoS^+$ *Salmonella typhimurium*, χ3339, and an isogenic rpoS mutant *Salmonella typhimurium*, χ4973.

FIG. 2 illustrates the time course of survival within rat bone marrow derived macrophages of an $rpoS^+$ *Salmonella typhimurium*, χ3339, and an isogenic rpoS mutant *Salmonella typhimurium*, χ4973.

FIG. 3 illustrates light micrographs at approximately 200× magnification (indicated by a 50 μm bar) showing normal murine Peyer's patch tissue in FIG. 3A; murine Peyer's patch tissue at one day (FIG. 3B), three days (FIG. 3C), and five days (FIG. 3D) after peroral infection with χ4973; and murine Peyer's patch tissue after peroral infection with χ3339 at one day (FIGS. 3E and 3F), three days (FIG. 3G), and five days (FIG. 3H) post infection.

FIG. 4 illustrates transmission electron micrographs at approximately 2000× magnification (indicated by a 5 μm bar) showing normal murine Peyer's patch lymphoid tissue (FIG. 4A), and murine Peyer's patch lymphoid tissue at five days after peroral infection with χ4973 (FIG. 4B) or χ3339 (FIG. 4C).

FIG. 5 illustrates transmission electron micrographs at approximately 2000× magnification (indicated by a 50 μm bar) showing normal murine Peyer's patch tissue (FIG. 5A), and normal murine Peyer's patch tissue five days after peroral infection with χ4973 (FIG. 5B) or χ3339 (FIG. 5C).

FIG. 6 illustrates the construction of plasmid vectors and bacterial strains with the defined ΔphoPQ23 mutation.

FIG. 7 illustrates the construction of plasmid vectors and bacterial strains with the defined ΔasdA16 mutation.

FIG. 8 illustrates the expression of the recombinant HBV core-pre-S protein by *S. typhimurium* Δcya Δcrp Δasd $RpoS^+$ and RpoS⁻ strains containing Asd⁺ vector, pYA3167, expressing the HBV core-pre-S antigen constructed by introducing the Asd⁺ vector into *S. typhimurium* χ8296 (Δcys Δcrp Δasd) and χ8309 (Δcys Δcrp Δasd rpoS) examined by (A) Coomassie blue stained 12% sodium dodecyl sulfate (SDS) polyacrylamide gel electrophoresis (PAGE) and (B) Western blot with a monoclonal antibody directed to the preS2 epitope with lanes in both gels as follows: lane 1, molecular markers; lane 2, χ8296 (Δcya-27 Δcrp-28 ΔasdA16 cfs RpoS⁺); lanes 3 & 4, χ8296 containing pYA3167 (Asd⁺ vector expressing HBV core-pre-S Ag); lane 5, χ8309 (Δcya-27 Δcrp-28 ΔasdA16 cfs rpoS); lanes 6 and 7, χ8309 plus pYA3167 (Asd⁺ vector expressing HBV core-pre-S Ag).

FIG. 9 illustrates the induction of antibody titers to HBV core-pre-S protein expressed by *S. typhimurium*, SL1344 strains in which mice were orally immunized with $10^9$ CFU or χ8296 (Δcya Δcrp Δasd RpoS⁺) containing pYA3167 (Asd⁺ vector specifying HBV core-pre-S) or the corresponding RpoS⁻ derivative, χ8309 (Δcya Δcrp Δasd RpoS⁺ containing pYA3167) showing (A) serum IgG antibody titer and (B) IgA antibody in vaginal washings determined at 4 and 6 weeks after immunization by ELISA using a recombinant polypeptide representing the full length pre-S sequence as a coating antigen (n=4).

FIG. 10 illustrates the levels of serum IgG antibodies to (A) recombinant HBV pre-S protein and (B) *typhimurium* LPS in groups of 8 mice perorally immunized with 2 doses of $10^9$ CFU of the RpoS⁺ strain, χ8296(pYA3167), (open circles) or the RpoS⁻ strain, χ8309(pYA3167), (open squares) and $10^8$ CFU of RpoS⁺ strain, χ8296(pYA3167), (solid circles) or the RpoS⁻ strain, χ8309(pYA3167), (solid squares) wherein serum samples were collected on weeks 2, 4, 6, and 8 weeks after dosing, pooled (N=8), diluted 1:400, measured by ELISA and expressed in the figure as optical density at 405 nm.

FIG. 11 illustrates the levels of serum IgA antibodies to (A) recombinant HBV pre-S protein and (B) *typhimurium* LPS in groups of 8 mice perorally immunized with 2 doses of $10^9$ CFU of the RpoS⁺ strain, χ8296(pYA3167), (solid bars) or the RpoS⁻ strain, χ8309(pYA3167), (hatched bars) wherein serum samples were collected on weeks 2, 4, 6, and 8 weeks after dosing, pooled (N=8), diluted 1:400, measured by ELISA and expressed in the figure as optical density at 405 nm.

Figure 14:
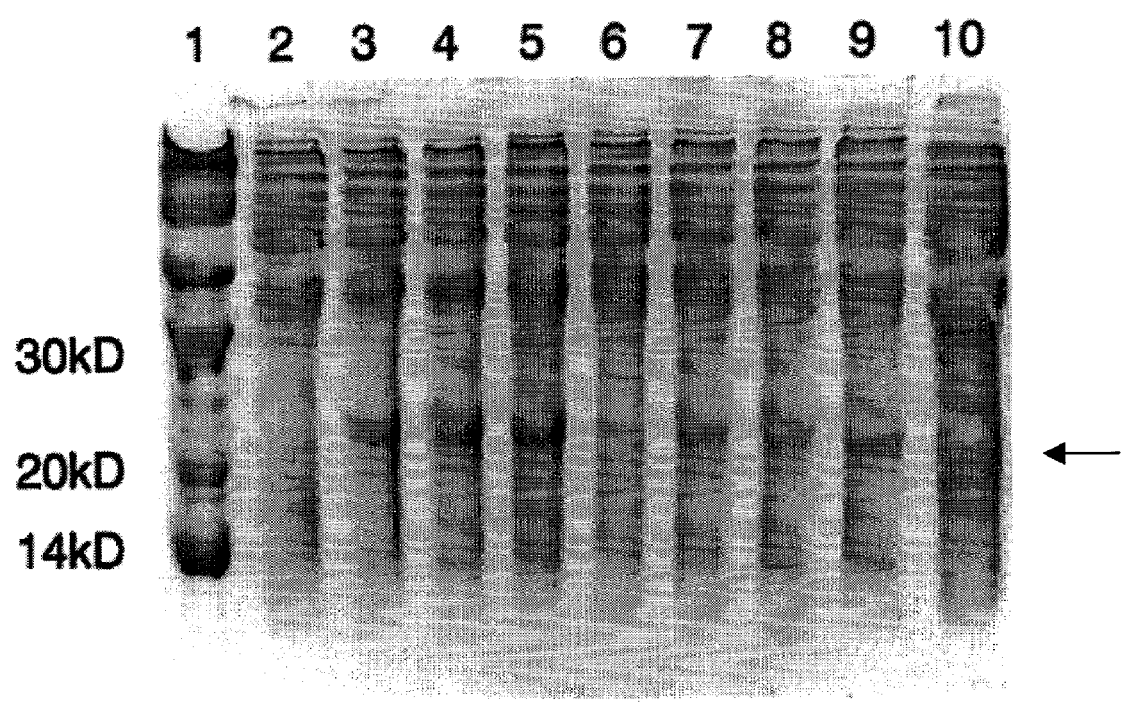

FIG. 14 illustrates Coomassie staining of 12% sodium dodecyl sulfate (SDS), polyacrylamide gel electrophoresis (PAGE) to show expression of the recombinant hybrid HBcAg-pre-S antigen in *S. typhi* ΔphoPQ Δasd vaccine strains, wherein the arrow indicates the position of the recombinant antigen for lane 1, polypeptide SDS-PAGE size standards; lane 2, MGN-1191; lane 3, MGN-1191/pYA3167, transformant #1 (χ8281); lane 4, MGN-1191/pYA3167, transformant #2; lane 5, MGN-1191/pYA3167, transformant #3; lane 6, MGN-1256; lane 7, MGN-1256/pYA3167, transformant #1 (χ8280); lane 8, MGN-1256/pYA3167, transformant #2; lane 9, MGN-1256/pYA3167, transformant #3; and lane 10, χ6212/pYA3167.

Figure 15:
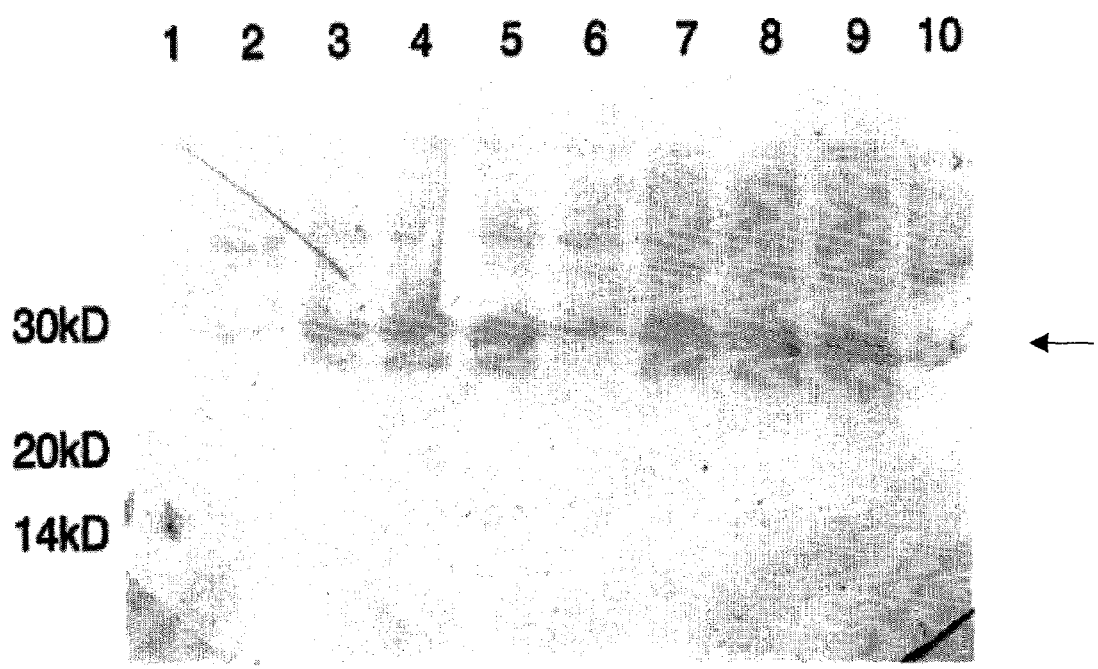

FIG. 15 illustrates immunostaining with anti-HBV-preS monoclonal antibody following SDS-12% PAGE to show expression of the recombinant hybrid HBcAg-pre-S antigen in *S. typhi* ΔphoPQ Δasd vaccine strains, wherein the arrow indicates the position of the recombinant antigen for lane 1, polypeptide SDS-PAGE size standards; lane 2, MGN-1191; lane 3, MGN-1191/pYA3167, transformant #1 (χ8281); lane 4, MGN-1191/pYA3167, transformant #2; lane 5, MGN-1191/pYA3167, transformant #3; lane 6, MGN-1256; lane 7, MGN-1256/pYA3167, transformant #1 (χ8280); lane 8, MGN-1256/pYA3167, transformant #2; lane 9, MGN-1256/pYA3167, transformant #3; and lane 10, χ6212/pYA3167.

Figure 16:
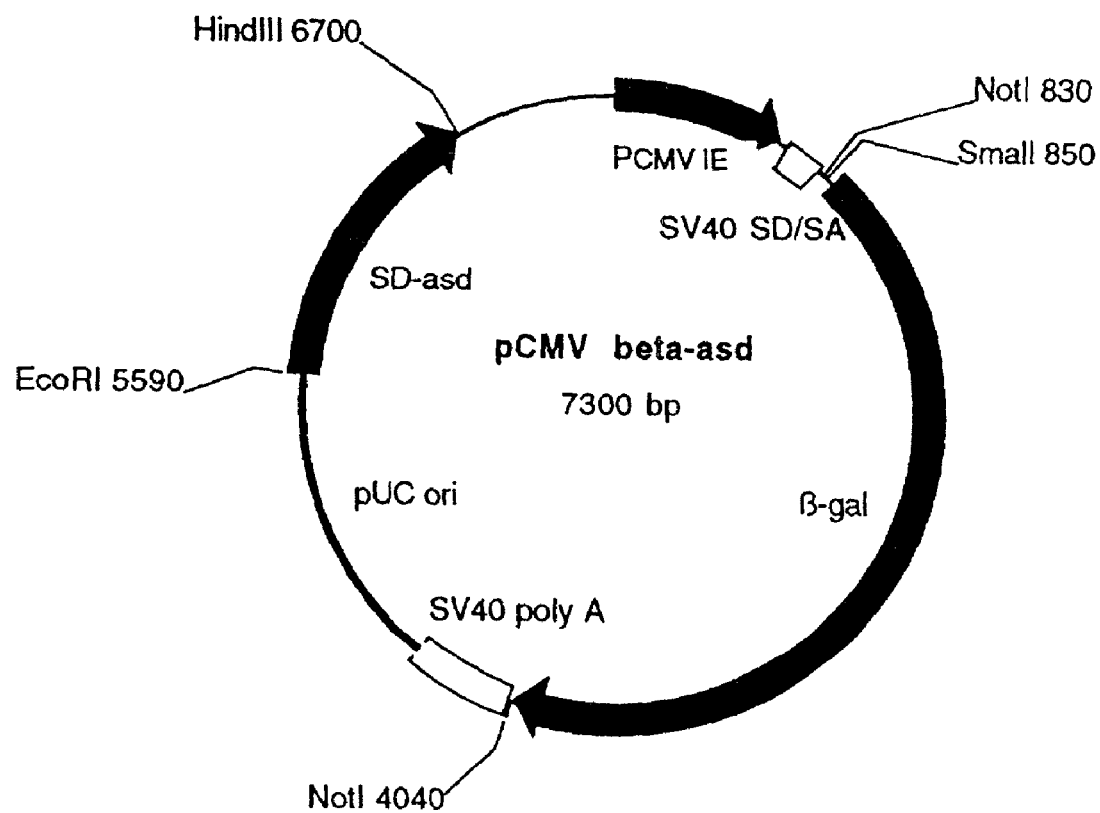

FIG. 16 illustrates the pCMV beta-asd plasmid.

DESCRIPTION OF THE PREFERRED EMBODIMENTS

The present invention is based upon the discovery made in *S. typhimurium*, which is predictive for other *Salmonella* such as *S. typhi*, that *Salmonella* having a functional rpoS gene and an RpoS⁺ phenotype have a high immunogenicity and can be advantageously used as vaccines and as carrier microbes. Such vaccines and carrier microbes can serve as vehicles for delivering desired gene products such as antigens to humans as well as for delivering nucleic acids, either DNA or RNA, to target human cells.

The rpoS gene product contributes to the virulence of *Salmonella typhimurium* in mice, at least in part, by regulating expression of chromosomal gene determinants of virulence and is believed to contribute to *S. typhi* virulence in humans through a similar mechanism. Much of the work that has led to the development of live *S. typhi* vaccines for immunization of humans has relied upon studies using strains of *S. typhimurium* tested in mice. These *S. typhimurium* strains cause an invasive infection in susceptible mice that resembles typhoid in humans. (Carter and Collins, *J. Exp. Med.* 139:1189–1203; Hohmann et al., *Infect Immun* 22:763–770, 1978; Coynaut et al. *Molecular Microbiol.* 22:149–160, 1996). Furthermore, the role of the rpoS gene in the invasiveness and virulence of *Salmonella typhimurium* is relevant to the invasiveness and virulence of *Salmonella typhi* which lack a virulence plasmid inasmuch as strains of *Salmonella typhimurium* cured of the virulence plasmid have been shown to colonize Peyers patches with efficiency similar to that of the wild-type microorganisms (Gulig and Curtiss, *Infect Immun* 55:2891–2901, 1987; Hackett et al., *J Infect Dis* 153:1119–1125, 1986). The results of studies in *Salmonella typhimurium*, which are thus also applicable to *Salmonella typhi*, show that the rpoS gene product controls the expression of chromosomally encoded genes which are important for invasiveness and virulence. (Nickerson and Curtiss, *Infect and Immun* 65:1814–1823, 1997; Kowarz et al, *J Bacteriol* 176:6852–6860, 1994).

In studies described in the Examples below, the inventors herein found that the presence of a functional rpoS gene is necessary for the early stages of the *Salmonella typhimurium* infection process at the level of the Peyer's patches and that the rpoS gene product acts through an interaction with chromosomal genes. In particular, it was discovered that an rpoS mutant of *S. typhimurium* exhibited wild-type abilities to attach to and invade cells of a human embryonic intestinal epithelial cell line, Int-407, and a murine macrophage-like cell line, J774. In addition, mutation in the rpoS gene did not affect the intracellular survival of *S. typhimurium* in either the J774 macrophage-like cells or rat bone marrow-derived macrophages. However, the rpoS mutant demonstrated a decreased ability to colonize murine Peyer's patches after oral inoculation as compared to its wild-type virulent parent strain.

In addition, virulence plasmid-cured derivatives of the rpoS mutant were recovered in lower numbers from murine Peyer's patches than were plasmid-cured derivatives of the isogenic wild-type *S. typhimurium*. This indicates that RpoS regulation of chromosomally-encoded genes is important for colonization of the murine gut associated lymphoid tissue (GALT) by *S. typhimurium*.

Microscopic analysis of histological sections taken from Peyer's patches after peroral infection of mice showed that, unlike its wild-type virulent parent strain, the isogenic rpoS mutant did not destroy the follicle-associated epithelium of the GALT. Furthermore, the rpoS mutant demonstrated a decreased ability to adhere to histological sections of murine Peyer's patches as compared to its wild-type parent. These data implicate the rpoS gene in the initial stages of systemic infection by *Salmonella* involving interaction of *Salmonella* with cells of the Peyer's patches.

As a result of the decreased ability of rpoS mutants to colonize Peyer's patches, earlier reports have suggested that *Salmonella* strains having an inactivating mutation in the rpoS gene are attractive candidates for use in live oral attenuated vaccines. (Nickerson and Curtiss, supra, 1996). In contrast to this earlier work, however, the present invention is directed to *Salmonella* strains and other bacteria having a functional rpoS$^+$ gene along with an attenuating mutation in another gene. As a result, the strains of the present invention are able to colonize Peyer's patches, or similar tissues including, for example, other lymphoid tissues of the GALT in humans, without destroying the invaded cells in order to achieve a high immunogenicity upon administration orally. Furthermore, the M cells of the follicle-associated lymphoid tissue of the GALT are functionally, morphologically and structurally the same as the M cells associated with other mucosal associated lymphoid tissues (MALT) in the body such as conjunctiva associated lymphoid tissue (CALT), bronchus associated lymphoid tissue (BALT) and nasal associated lymphoid tissue (NALT), as well as lymphoid tissues in the rectum, etc. Thus, it is believed that the presence of a functional rpoS$^+$ gene in the *Salmonella* will play an important role in the invasion and colonization of these tissues when administration is by routes including oral, intranasal, rectal, etc. In fact, as shown in the examples below, RpoS$^+$ *S. typhimurium*, both non-recombinant and recombinant expressing a foreign antigen, are superior to isogenic RpoS$^-$ *S. typhimurium* strains in conferring protective immunity and in eliciting antibody responses to the foreign antigens when delivered intranasally where colonization of the NALT and BALT should be of prime importance.

The *Salmonella* and other bacterial strains within the scope of the present invention can be selected on the basis of their having a functional rpoS$^+$ gene which produces a functional rpoS gene product. The rpoS gene product is known to be a stationary-phase sigma factor which is responsible for the control of a regulon of over 30 genes expressed in response to starvation, during the transition to stationary phase and in response to stresses. Protein products of genes under the control of RpoS regulate a number of cell functions including protection against DNA damage, the determination of morphological changes, the mediation of virulence, osmoprotection, thermotolerance (Loewen and Hengge-Aronis, *Annu. Rev. Microbiol.* 48:53–80, 1994) and acid tolerance (Lee et al., *Mol. Microbiol.* 17:155–167, 1995). Many of these stresses are encountered by bacteria during infection or immunization of an animal or human host. Reference to RpoS phenotype herein is intended to mean the manifestation of cell functions regulated by rpoS gene expression in the microbe.

Many of the cell functions controlled by RpoS regulation can be assessed in determining the RpoS phenotype of a microbe. For example, one can analyze cultures for catalase production. This test is based upon RpoS positive regulation of the katE gene, which produces hydroperoxidase II catalase. The culture medium of strains carrying the wild-type rpoS allele grown to stationary phase, bubble vigorously upon addition of hydrogen peroxide, whereas minimal bubbling occurs in the stationary phase culture medium of strains carrying a mutant rpoS allele (Lowen, *J. Bacteriol.* 157:622–626, 1984; Mulvey et al., *Gene* 73:337–345, 1988). The RpoS phenotypes of the attenuated *S. typhimurium* strains can also be assayed by determining the sensitivity of these strains to nutrient deprivation, acid or oxidative stresses, and defective glycogen biosynthesis ability. In a variation of this approach, the RpoS phenotype could be determined by P22HTint-mediated transduction of the rpoS allele into wild-type *S. typhimurium* χ3339, with subsequent testing of the derived microbe for catalase production as described above.

One can also genetically alter a strain which does not contain a functional rpoS$^+$ gene using conjugation, transformation, or transduction to introduce a functional recombinant rpoS$^+$ gene which provides an RpoS$^+$ phenotype in the catalase test. The recombinant rpoS$^+$ gene can be from any suitable homologous or heterologous source, preferably a homologous source.

It may also be possible to introduce into *Salmonella* containing a functional rpoS$^+$ gene another functional recombinant rpoS$^+$ gene on a plasmid replicon or integrated into the chromosome to further enhance the expression of genes regulated by the RpoS protein. This might be desirable in certain situations such as, for example, in microbes having diminished rpoS gene expression, i.e., microbes which display nonoptimal colonization of the GALT, or even in microbes in which the rpoS gene expression is not diminished but a greater than normal expression is desired.

It is also possible to provide a *Salmonella* or other bacteria strain that is able to effectively colonize the GALT or other lymphoid tissues even though it does not express functional RpoS. For example, the RpoS$^-$ phenotype could be circumvented by incorporating into an rpoS mutant strain at least one recombinant virulence gene. Recombinant virulence gene or recombinant RpoS virulence gene as referenced herein is intended to mean that the recombinant gene is capable of expressing a gene product having the same biological function, i.e. facilitating effective colonization of the GALT or other lymphoid tissue, as that of a chromosomal virulence gene normally regulated by RpoS. However, expression of the incorporated recombinant virulence gene is controlled by regulatory elements that are not dependent upon the presence of functional RpoS, thereby providing expression of the recombinant virulence gene product in the absence of functional RpoS. For example, a functional rpoS$^+$ gene is shown to be important for adherence by *Salmonella* to Peyer's patches, which is necessary for colonization of this tissue. One or more genes responsible for this adherence is believed to be regulated by RpoS. One group of candidate genes controlling adherence to Peyer's patches that may be regulated by RpoS may be the lpf fimbrial operon (Bäumler et al., *Proc. Natl. Acad. Sci., USA* 93:279–283, 1996). Thus, the invasiveness and immunogenicity of an rpoS mutant microbe can be enhanced by transforming the microbe with one or more virulence genes under the control of regulatory elements that are not dependent upon the presence of functional RpoS.

In one embodiment of the present invention, the rpoS$^+$ bacterial strains, in particular rpoS$^+$ *Salmonella* strains, are attenuated derivatives of a pathogenic strain. By derivative or derived strain reference is made to a strain that has been genetically modified from its parent from which it is descended. By pathogenic it is meant that the microbe is capable of causing disease or impairing normal physiological functioning. Reference to avirulence or attenuation herein, is intended to mean that a particular microbe strain is incapable of inducing a full suite of symptoms of the disease state that is normally associated with its virulent non-attenuated pathogenic counterpart. Thus, avirulence or attenuation includes a state of diminished virulence or ability to produce disease conditions and the attenuated or avirulent microorganisms are not necessarily completely absent of any ability to impair normal physiological functioning of the host. In addition, an attenuated or avirulent microbe is not necessarily incapable of ever functioning as a pathogen, but the particular microbe being used is attenuated with respect to the particular individual being treated.

The rpoS$^+$ strains of the present invention, including rpoS$^+$ *Salmonella* strains, are attenuated by virtue of their containing an attenuating mutation in one or more genes that renders the microorganism attenuated. In a preferred embodiment, the strains have at least two mutations each of which act to attenuate the microorganism and which, in combination, significantly increase the probability that the microorganism will not revert to wild-type virulence. Mutations can be insertions, partial or complete deletions or the like so long as expression of the gene is diminished and virulence is decreased. Attenuating mutations can be in biosynthetic genes, regulatory genes and/or genes involved in virulence. (See Doggett and Brown, supra). Examples of mutations include, but are not limited to a mutation in a pab gene, a pur gene, an aro gene, asd, a dap gene, nadA, pncB, galE, pmi, fur, rpsL, ompR, htrA, hemA, cdt, cya, crp, dam, phoP, phoQ, rfc, poxA, galU, metL, metH, mviA, sodC, recA, ssrA, ssrB, sirA, sirB, sirC, inv, hilA, hilC, hilD, rpoE, flgM, tonB, slyA, and combinations thereof. The skilled artisan will readily appreciate that any suitable gene mutation can be used in the present invention so long as the mutation of that gene renders the microorganism attenuated.

Methods are known in the art that can be used to generate mutations to produce the attenuated microbes of the present invention. For example, the transposon, Tn10, can be used to produce chromosomal deletions in a wide variety of bacteria, including *Salmonella* (Kleckner et al., *J. Mol. Biol.* 116:125–159, 1977; EPO Pub. No. 315,682; U.S. Pat. No. 5,387,744).

Recently, new methods have become available for producing specific deletions in genes. These methods involve initially selecting a gene in which the deletion is to be generated. In one approach the gene can be selected from a genomic library obtained commercially or constructed using methods well known in the art (Sambrook et al., Molecular Cloning: A Laboratory Manual, 2nd Ed., 1989, Cold Spring Harbor Press, Cold Spring Harbor, N.Y.). Clones containing the gene are isolated from the genomic library by complementation of a strain which contains a mutation in the same gene. Alternatively, when the DNA sequence of the gene is known, selected primers for the polymerase chain reaction method (PCR) can amplify the gene, often with some flanking sequence, from a sample of bacteria or from purified genomic DNA and the PCR product can be inserted into a cloning vector.

A specific deletion in the selected gene can be generated by either of two general methods. The first method generates a mutation in a gene isolated from a population of clones contained in a genomic DNA library using restriction enzymes and the second method generates the mutation in a gene of known sequence using PCR.

Using the first method, the position of the gene on a vector is identified using transposon tagging and a restriction map of the recombinant DNA in the vector is generated. Information derived from the transposon tagging allows all or a portion of a gene to be excised from the vector using the known restriction enzyme sites.

The second method which is based upon PCR methodology can be used when the DNA sequence of the gene is known. According to this method, divergent PCR primers amplify the upstream and downstream regions flanking a specified segment of DNA to be deleted from the gene and generate a PCR product consisting of the cloning vector and upstream and downstream flanking nucleotide sequences (Innes et al. Eds., PCR Protocols, 1990, Academic Press, New York). In a variation of this method, PCR products are produced representing portions of the gene or flanking sequence, which are then joined together in a cloning vector.

The DNA containing the mutant gene can be introduced into the bacterial host by transformation using chemical means or electroporation, by recombinant phage infection, or by conjugation. In preferred embodiments the mutant gene is introduced into the chromosomes of the bacteria which can be accomplished using any of a number of methods well known in the art such as, for example, methods using temperature-sensitive replicons (Hamilton et al., *J. Bacteriol.* 171:4617–4622, 1989), linear transformation of recBC mutants (Jasin et al., *J. Bacteriol.* 159:783–786, 1984), or host restricted replicons known as suicide vectors (Miller et al., *J. Bacteriol.* 170:2575–2583, 1988). The particular method used is coupled with an appropriate counter selection method such as, for example, fusaric acid resistance or sucrose resistance followed by subsequent screening for clones containing the mutant allele based upon phenotypic characteristics or by using PCR, nucleic acid hybridization, or an immunological method.

The attenuated rpoS$^+$ bacteria strains of the present invention, in particular, attenuated *S. typhi* mutants, can be used in the form of vaccines to deliver recombinant antigens to a human or nucleic acids to target cells of a human. Thus, it is apparent that the present invention has wide applicability to the development of effective recombinant vaccines against bacterial, fungal, parasite or viral disease agents in which local immunity is important and might be a first line of defense. Some examples are recombinant vaccines for the control of bubonic plague caused by *Yersinia pestis*, of gonorrhea caused by *Neisseria gonorrhoea*, of syphilis caused by *Treponema pallidum*, and of venereal diseases as well as eye infections caused by *Chlamydia trachomatis* or of pneumonia caused by *C. pneumoniae*. Species of *Streptococcus* from both group A and group B, such as those species that cause sore throat or heart disease, *Neisseria meningitidis*, *Mycoplasma pneumoniae*, *Haemophilus influenzae*, *Bordetella pertussis*, *Mycobacterium tuberculosis*, *Mycobacterium leprae*, *Streptococcus pneumoniae*, *Brucella abortus*, *Vibrio cholerae*, *Shigella* species, *Legionella pneumophila*, *Helicobacter pylori*, *Campylobacter jejuni*, *Borrelia burgdorferi*, *Rickettsia* species, *Pseudomonas aeruginosa*, and pathogenic *E. coli* such as ETEC, EPEC, UTEC, EHEC, and EIEC strains are additional examples of microbes within the scope of this invention from which genes could be obtained. Recombinant anti-viral vaccines, such as those produced against influenza viruses, are also encompassed by this invention. Recombinant anti-viral vaccines can also be produced against viruses, including RNA viruses such as Picornaviridae, Caliciviridae, Togaviridae, Flaviviridae, Coronaviridae, Rhabdoviridae, Filoviridae, Paramyxoviridae, Orthomyxoviridae, Bunyaviridae, Arenaviridae, Reoviridae or Retroviridae; or DNA viruses such as Hepadnaviridae, Paroviridae, Papovaviridae, Adenoviridae, Herpesviridae or Poxviridae. Recombinant vaccines to protect against infection by pathogenic fungi, protozoa or parasites are also contemplated by this invention. All of the above examples of pathogens are provided for illustrative purposes and are not intended to be construed in a limiting sense.

Thus, in one set of embodiments, the present invention can be described as a vaccine for the immunization of a human comprising a live attenuated derivative of a pathogenic bacteria such as a pathogenic *S. typhi* wherein the derivative contains a functional rpoS gene and expresses an RpoS+ phenotype. The attenuated bacteria is also capable of expressing a recombinant gene derived from an organism that is a pathogen of or that produces an allergen of the human.

In embodiments in which the immunogenic component of the vaccine is an allergen of the host, such a vaccine can be used in an exposure regimen designed to specifically desensitize an allergic host. Allergies to pollens, mold spores, insect parts, animal dander and the like are due to the inhalation of air and/or ingestion of feed containing such allergens. The allergies that result are associated with a presence of IgE antibodies that bind to allergens which activate mast cells for release of histamines. As is well known, desensitization against allergens can be achieved by repetitive parenteral immunization of extracts containing the allergen. Likewise, it is known that oral ingestion of raw honey containing pollens can be used to effectively induce a state of tolerance against those allergens. Oral ingestion with such allergens can on the one hand induce an SIgA response that could block the ability of allergens to react with IgE and mast cells or if administered in sufficient quantity could serve to suppress the synthesis of IgE antibodies, that is to induce tolerance. Since the specific allergenic molecule in many allergens has been identified and the cDNA cloned to obtain the nucleotide sequence specifying the allergen, it is now possible to genetically engineer heterologous host cells to express the allergen (see for example, Valenta et al, *Allergy* 53:552–561. 1998; Olsson et al., *Clin. Exp. Allergy* 28:984–991. 1998; Soldatova et al., *J. Allergy Clin. Immunol.* 101:691–698, 1998; Asturias et al, *Clin Exp Allergy* 27:1307–1313; Twardosz et al, *Biochem Biophys Res Commun* 239:197–204, 1997). Accordingly, the attenuated RpoS+ *Salmonella* of the present invention can be engineered to express an allergen, possibly in a modified immunogenic but nonallergenic form to induce a state of tolerance or to actively promote the production of SIgA against the allergen. The RpoS+ attenuated *Salmonella* described herein have been shown to be effective in eliciting immune responses and, hence, it follows that use of such RpoS+ *Salmonella* to express modified allergens would be likely to be effective in ameliorating the consequences of exposure of humans to allergens by inhalation or ingestion.

In other embodiments, the recombinant gene expresses a gamete-specific antigen which is capable of eliciting an immune response that confers an antifertility effect upon the immunized individual (See, U.S. Pat. No. 5,656,488).

The attenuated microbes of this invention can additionally be used as vectors for the synthesis of various host proteins. Because the attenuated microbes of this invention are able to traverse a variety of immunocompetent structures including gut-associated lymphoid tissue (GALT), mesenteric lymph nodes and spleen after introduction into the host, such microbes can be used to target a variety of immunoregulatory products. Accordingly, one or more genes encoding immunoregulatory proteins or peptides can be recombinantly introduced into the attenuated microbes such that when the microbes taking up residence in the appropriate immunocompetent tissue are capable of expressing the recombinant product to suppress, augment or modify the immune response in the host. Examples of immunoregulatory molecules include but are not limited to: colony stimulating factors (macrophage, granulocyte, or mixed), macrophage chemotoxin, macrophage inhibition factor, leukocyte inhibitory factors, lymphotoxins, blastogenic factor, interferon, interleukins, tumor necrotizing factor, cytokines, and lymphokines.

The attenuated microbes of the present invention are also contemplated for use to deliver and produce pharmacologically active products that might stimulate or suppress various physiological functions (i.e., growth rate, blood pressure, development of sexual maturity etc.). In such microbes, the recombinant gene encodes said pharmacologically active products.

The recombinant gene of the microbes of the present invention can be incorporated into a "balanced-lethal" system which selects for microorganisms containing and capable of expressing the recombinant gene by linking the survival of the microorganism to the continued presence of the recombinant gene. "Balanced-lethal" mutants of this type are characterized by a lack of a functioning native chromosomal gene encoding an enzyme which is essential for cell survival, preferably an enzyme which catalyzes a step in the biosynthesis of diaminopimelic acid (DAP) and even more preferably a gene encoding beta aspartate semialdehyde dehydrogenase (Asd). DAP pathway enzymes and Asd are required for cell wall synthesis. The mutants also contain a first recombinant gene which can serve to complement the non-functioning chromosomal gene and this is structurally linked to a second recombinant gene encoding the desired product. Loss of the complementing recombinant gene causes the cells to die by lysis when the cells are in an environment where DAP is lacking. This strategy is especially useful since DAP is not synthesized by eukaryotes and, therefore, is not present in immunized host tissues. Methods of preparing these types of "balanced lethal" microbes are disclosed in U.S. Pat. No. 5,672,345.

By immunogenic agent is meant an agent used to stimulate the immune system of an individual, so that one or more functions of the immune system are increased and directed towards the immunogenic agent. Immunogenic agents include vaccines. Immunogenic agents can be used in the production of antibodies, both isolated polyclonal antibodies and monoclonal antibodies, using techniques known in the art.

An antigen or immunogen is intended to mean a molecule containing one or more epitopes that can stimulate a host immune system to make a secretory, humoral and/or cellular immune response specific to that antigen.

An epitope can be a site on an antigen to which an antibody specific to that site binds. An epitope could comprise 3 amino acids in a spatial conformation which is unique to the epitope; generally, an epitope consists of at least 5 amino acids and more usually, at least 8–10 amino acids. The term "epitope" is intended to be interchangeable with the term "antigenic determinant" as used herein. The term "epitope" is also intended to include T-helper cell epitopes in which an antigenic determinant is recognized by T-helper cells through association with major histocompatibility complex class II molecules. In addition, the term epitope includes any antigen, epitope or antigenic determinant which is recognized by cytotoxic T cells when presented by a MHC class I molecule on the surface of an antigen presenting cell. A cytotoxic T cell epitope can comprise an amino acid sequence of between about 6 to about 11 amino acids, and preferably comprises a sequence of 8 or 9 amino acids.

By vaccine is meant an agent used to stimulate the immune system of an individual so that protection is provided against an antigen not recognized as a self-antigen by the immune system. Immunization refers to the process of inducing a continuing high level of antibody and/or cellular immune response in which T-lymphocytes can either kill the pathogen and/or activate other cells (e.g., phagocytes) to do so in an individual, which is directed against a pathogen or antigen to which the organism has been previously exposed. Although the phrase "immune system" can encompass responses of unicellular organisms to the presence of foreign bodies, in this application the phrase is intended to refer to the anatomical features and mechanisms by which an individual produces antibodies against an antigenic material which invades the cells of the individual or the extra-cellular fluid of the individual and is also intended to include cellular immune responses. In the case of antibody production, the antibody so produced can belong to any of the immunological classes, such as immunoglobulins, A, D, E, G or M. Of particular interest are vaccines which stimulate production of immunoglobulin A (IgA) since this is the principle immunoglobulin produced by the secretory system of warm-blooded animals, although vaccines of the invention are not limited to those which stimulate IgA production. For example, vaccines of the nature described herein are likely to produce a broad range of other immune responses in addition to IgA formation, for example cellular and humoral immunity. Immune responses to antigens are well studied and widely reported. A survey of immunology is provided in Elgert, Klaus D., *Immunology,* Wiley Liss, Inc., (1996); Stites et al., *Basic & Clinical Immunology; 7th Ed.,* Appleton & Lange, (1991) the entirety of which are incorporated herein by reference.

An "individual" treated with a vaccine of the present invention is defined herein as referring to a human host.

Microbes as used herein can include bacteria, protozoa and both unicellular and multicellular fungi. The term parasite as used herein is intended to include protozoans such as species of *Plasmodium* and *Toxoplasma* as well as species of *Entamoeba, Leishmania* and *Trypanosoma* and helminths such as trematodes, cestodes and nematodes. Viruses as used herein can include RNA viruses such as, for example, Picornaviridae, Caliciviridae, Togaviridae, Flaviviridae, Coronaviridae, Rhabdoviridae, Filoviridae, Paramyxoviridae, Orthomyxoviridae, Bunyaviridae, Arenaviridae, Reoviridae and Retroviridae; and DNA viruses such, for example, as Hepadnaviridae, Paroviridae, Papovaviridae, Adenoviridae, Herpesviridae and Poxviridae.

Reference to a recombinant gene is intended to mean genetic material that is transferred by human intervention from a first organism into a second organism which upon reproduction gives rise to descendants containing the same genetic material. Generally, such exchange of genetic material from the first organism to the second organism either does not take place or rarely takes place in nature.

The term gene as used herein in its broadest sense represents any biological unit of heredity. It is not, however, necessary that the recombinant gene be a complete gene as is present in the parent organism and capable of producing or regulating the production of a macromolecule such as for example, a functioning polypeptide. The recombinant gene may, thus, encode all or part of an antigenic product. Furthermore, the recombinant gene can also include DNA sequences that serve as promoters, enhancers or terminators and DNA sequences that encode repressors or activators that regulate expression of a recombinant gene encoding all or part of an antigen. A recombinant gene can also refer to gene fusions which encode polypeptide fusion products. The encoded gene product can, thus, be one that was not found in that exact form in the parent organism. For example, a functional gene coding for a polypeptide antigen comprising 100 amino acid residues can be transferred in part into a carrier microbe so that a peptide comprising only 75, or even 10, amino acid residues is produced by the cellular mechanisms of the host cell. However, if this gene product can serve as an antigen to cause formation of antibodies against a similar antigen present in the parent organism or as a T-cell epitope recognized by T-helper cells, the gene is considered to be within the scope of the term gene as defined in the present invention. Alternatively, if the amino acid sequence of a particular antigen or fragment thereof is known, it is possible to chemically synthesize the DNA fragment or analog thereof by means of automated gene synthesizers or the like and introduce said DNA sequence into the appropriate expression vector. This might be desirable in order to use codons that are preferred codons for high level expression in *Salmonella*. At the other end of the spectrum is a long section of DNA coding for several gene products, one or all of which can be antigenic. For example, such a long section of DNA could encode 5 to 15 proteins necessary for the synthesis of fimbrial antigens (fimbriae), which mediate adhesion of pathogens to host cells (Bäumler et al., supra). The induction of an immune response against fimbriae can provide protection against the pathogen. Thus, a gene as defined and claimed herein is any unit of heredity capable of producing an antigen. The gene can be of chromosomal, plasmid, or viral origin. It is to be understood that the term gene as used herein further includes DNA molecules lacking introns such as, for example, is the case for cDNA molecules, so long as the DNA sequence encodes the desired gene product. Further, the term gene includes within its meaning RNA molecules that serve as genes of RNA viruses or the complement of such RNA molecules wherein the RNA molecule or complement thereof can serve as an mRNA to be transcribed into a viral protein which is immunogenic. The term gene as used herein also includes a DNA sequence specifying the viral strand that serves as an mRNA to be translated into the viral protein which is immunogenic.

In order for the gene to be effective in eliciting an immune response, the gene must be expressed. Expression of a gene means that the information inherent in the structure of the gene (the sequence of DNA bases) is transformed into a physical product in the form of an RNA molecule, polypeptide or other biological molecule by the biochemical mechanisms of the cell in which the gene is located. The biological molecule so produced is referenced as the gene product. The term gene product as used here refers to any biological product or products produced as a result of the biochemical reactions that occur under the control of a gene. The gene product can be, for example, an RNA molecule, a peptide, or a product produced under the control of an enzyme or other molecule that is the initial product of the gene, i.e., a metabolic product. For example, a gene can first control the synthesis of an RNA molecule which is translated by the action of ribosomes into an enzyme which controls the formation of glycans in the environment external to the original cell in which the gene was found. The RNA molecule, the enzyme, and the glycan are all gene products as the term is used here. Any of these as well as many other types of gene products, such as glycoproteins, glycolipids and polysaccharides, will act as antigens if introduced into the immune system of an individual. Protein gene products, including glycoproteins and lipoproteins, are preferred gene products for use as antigens in vaccines.

In order for a vaccine to be effective in stimulating cellular immunity or in producing antibodies, the antigenic materials must be released and/or presented in such a way to trigger the induction of a cellular immunity and/or induce the antibody-producing mechanism of the vaccinated individual. Therefore, the microbe carrier of the gene product must be introduced into the individual. In order to stimulate a preferred response of the gut-associated lymphoid tissue (GALT) or bronchus-associated lymphoid tissue (BALT), introduction of the microbe or gene product directly into the gut or bronchus is preferred, such as by oral administration, gastric intubation or intranasally in the form of aerosols, although other methods of administering the vaccine, such as intravenous, intramuscular, subcutaneous injection or intramammary or intrapenial or vaginal or rectal administration, are possible.

The attenuated microbe can be used as a carrier microbe, for example, for an antigen or for a DNA or RNA vaccine vector, and once the carrier microbe is present in the individual, the antigen needs to become available to the individual's immune system. In the case of a carrier microbe for delivery of a nucleic acid molecule, the nucleic acid molecule needs to be released within the target cell. This can be accomplished when the carrier microbe dies so that the antigen molecules or nucleic acid molecules are released. Of course, the use of "leaky" attenuated mutants that release the contents of the periplasm without lysis is also possible.

Alternatively, a gene can be selected that controls the production of an antigen that will be made available by the carrier cell to the outside environment prior to the death of the cell. In this way, it is possible to use a viable microbe that will persist in the vaccinated individual, for example in its Peyer's patches or other GALT, NALT or BALT, etc., and continue to produce antigen, thereby continually inducing antibody formation and/or a cellular immune response. A preferred gene product under these circumstances is a product that is transferred through the cell membrane of the attenuated carrier microbe into the external environment or a product that becomes attached to or embedded in the external membrane so that all or part of the gene product is exposed to the environment. Typical of this latter type of gene product are antigens normally found on the surface of the organism against which protection is desired. If these antigens are transported to the bacterial cell surface in a normal manner, antibody formation against the antigens will be enhanced.

Nucleic acid vaccines are well known in the art (see e.g., Ulmer et al., *Amer. Soc. Microbiol. News* 62:476–479, 1996; Ulmer et al., *Curr. Opinion. Immunol.* 8:531–536, 1996; and Robinson, H. L., *Vaccine* 15:785–787, 1997) and delivery of DNA vaccines by attenuated bacteria with subsequent stimulation of an immune response against the protein-encoded by the DNA vaccine has been described (Sizemore et al., *Vaccine* 15:804–806, 1997). Thus, it is expected that the attenuated microbes of the present invention can also be used as delivery vehicles for DNA vaccines. Typically, bacteria containing such DNA vaccines do not themselves express the gene product encoded by the DNA vaccine, but release the DNA vaccine into one or more human tissues, where the gene product is then expressed by host cell transcription and translation machinery. However, it is also contemplated that a DNA vaccine for immunization against RNA viruses can be constructed in which copies of the RNA viral genome, or of a protein-encoding portion thereof, will be made in the cytoplasm of the attenuated bacteria. Such RNA molecules would be released into the human tissues, e.g., by lysis of the attenuated bacteria, where they would serve as mRNA for synthesis of immunogenic viral protein(s). It is also contemplated that the DNA vaccine vector within the attenuated bacterial host could synthesize the mRNA for a desired gene product within the bacteria which could then be delivered to the eukaryotic cell where the mRNA would be directly translated into the desired gene product. In this case, the mRNA would possess information or signals that caused translation to be dependent on the eukaryotic host cell and which would preclude, for the most part, translation within the attenuated bacterial cell.

The use of pathogens to deliver antigens from other pathogens to the GALT or BALT would be inappropriate if it were not for the fact that such pathogens can be rendered attenuated while retaining ability to colonize these tissues.

The organism from which the recombinant gene is derived can be any human pathogen or may be an organism that produces an allergen or other antigen to which a human can be sensitive. Allergens are substances that cause allergic reaction, in this case in the human which will be vaccinated against them. Many different materials can be allergens, such as animal dander and pollen, and the allergic reaction of individuals will vary for any particular allergen. It is possible to induce tolerance to an allergen in an individual that normally shows an allergic response. The methods of inducing tolerance are well-known and generally comprise administering the allergen to the individual in increasing dosages. Further discussion of tolerance induction is given in the Barrett textbook previously cited. Lastly, the host individual itself can serve as a source of genetic material when immunoregulatory genes or genes for other pharmacologically active substances are being expressed by the vectors.

Administration of a live vaccine of the type disclosed above to an individual can be by any known or standard technique. These include oral ingestion, gastric intubation, or broncho-nasal-ocular spraying. All of these methods allow the live vaccine to easily reach the NALT, GALT or BALT cells and induce antibody formation and cell mediated immunity and are the preferred methods of administration. Other methods of administration, such as intravenous injection, that allow the carrier microbe to reach the individual's blood stream can be acceptable. Intravenous, intramuscular or intramammary injection are also acceptable with other embodiments of the invention, as is described later.

Any of a number of commonly used recombinant DNA techniques can be used in producing the attenuated microbes of the present invention which are capable of expressing a recombinant gene. Following ligation to a plasmid, phage or cosmid vector the recombinant molecules so formed can be transferred into a host cell by various means such as conjugation, or transformation (uptake of naked DNA from the external environment, which can be artificially induced by the presence of various chemical agents, such as calcium ions), including electroporation. Other methods such as transduction are also suitable, wherein the recombinant DNA is packaged within a phage such as transducing phage or cosmid vectors. Once the recombinant DNA is in the carrier cell, it may continue to exist as a separate autonomous replicon or it may insert into the host cell chromosome and be reproduced along with the chromosome during cell division.

Once the genetic material has been transferred, the microbes containing the transferred genetic material are selected.

The immunization dosages required will vary with the antigenicity of the gene product and need only be an amount sufficient to induce an immune response. Routine experimentation will easily establish the required amount. Multiple dosages are used as needed to provide the desired level of protection.

The pharmaceutical carrier or excipient in which the vaccine is suspended or dissolved may be any solvent or solid or encapsulating material such as for a lypholized form of the vaccine. The carrier is non-toxic to the inoculated individual and compatible with the microorganism or antigenic gene product. Suitable pharmaceutical carriers are known in the art and, for example, include liquid carriers, such as normal saline and other non-toxic salts at or near physiological concentrations, and solid carriers, such as talc or sucrose. Gelatin capsules can serve as carriers for lypholized vaccines. Adjuvants may be added to enhance the antigenicity if desired. When used for administering via the bronchial tubes, the vaccine is preferably presented in the form of an aerosol. Suitable pharmaceutical carriers and adjuvants and the preparation of dosage forms are described in, for example, Remington's Pharmaceutical Sciences, 17th Edition, (Gennaro, Ed., Mack Publishing Co., Easton, Pa., 1985).

Immunization of an individual with a pathogen-derived gene product can also be used in conjunction with prior immunization with the attenuated derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the pathogen-derived gene product to stimulate the lymphoid cells of the GALT or BALT. The enhanced response is known as a secondary, booster, or anamnestic response and results in prolonged immune protection of the host. Booster immunizations may be repeated numerous times with beneficial results.

In another embodiment, the present invention provides a method for assessing the immunogenicity of a *Salmonella* comprising determining the RpoS phenotype of the *Salmonella*. The method is also applicable for other bacteria such as *Shigella* and *E. coli* and *Salmonella-Shigella* hybrids, *Salmonella-E. coli* hybrids and *Shigella-E. coli* hybrids. The presence of an $RpoS^+$ phenotype confers upon the microbe the ability to invade and colonize the lymphoid tissue associated with the particular route of administration used such as, for example, the GALT following oral administration or other lymphoid tissues, such as the NALT or BALT following other routes of administration. This in turn results in a high level of immunogenicity. Thus, detecting the presence of an $RpoS^+$ phenotype indicates that the microbe will have a high level of immunogenicity compared to a microbe that is $RpoS^-$, but otherwise genetically identical.

The $RpoS^+$ phenotype can be assessed by determining the properties of the microbe. This can be done by any of a number of possible methods. For example, by analyzing cultures for catalase production. This test is based upon RpoS positive regulation of the katE gene, which produces hydroperoxidase II catalase. The culture medium of strains carrying the wild-type rpoS allele bubble vigorously upon addition of hydrogen peroxide, whereas minimal bubbling occurs in the culture medium of strains carrying a mutant rpoS allele (Lowen, *J. Bacteriol.* 157:622–626, 1984; Mulvey et al., *Gene* 73:337–345, 1988). Other methods can also be used for determining the RpoS phenotypes of the attenuated *Salmonella* or other bacteria strains including determining the sensitivity of the strains to nutrient deprivation, acid or oxidative stresses, and defective glycogen biosynthesis ability. In a variation of this approach, the rpoS allele can be transduced into a wild-type *Salmonella* and the resultant derivative *Salmonella* tested for RpoS phenotype.

One can also assess the $RpoS^+$ phenotype by determining the genetic make up of the microbe wherein the presence of a functional $rpoS^+$ gene capable of producing a functional rpoS gene product indicates an $RpoS^+$ phenotype.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

General Methods:

The bacterial strains used in the present studies were constructed using the following general materials and methods. Listings of phages, plasmids and micro organisms used in constructing the strains are given in Tables 1 and 2.

TABLE 1

Microorganisms

| Strain Designation | Relevant Genotype | Source/Reference/Derivation |
|---|---|---|
| *Salmonella typhi* Strains | | |
| χ3743 | ISP1804 Type 46 | 1983 isolate from Chilean patient, received from D. Hone, Center for Vaccine Development, MD |
| χ3744 | ISP1820 Type 46 cys trp | ATCC 55116; 1983 isolate from Chilean patient; received from D. Hone |
| χ3745 | ISP2822 Type E1 | ATCC 55114; 1983 isolate from Chilean patient; received from D. Hone |
| χ3746 | ISP2825 Type E1 | 1983 isolate from Chilean patient; received from D. Hone |
| χ3769 | Ty2 Type E1 rpoS cys | Louis Baron, Walter Reed Army Institute of Research |
| χ3927 | Ty2 Δcrp-11 Δ[zhb: :Tn10] Δcya-12 Δ[zid-62: :Tn10] | ATCC 55117 |

TABLE 1-continued Microorganisms

| Strain Designation | Relevant Genotype | Source/Reference/Derivation |
|---|---|---|
| χ4073 | Ty2 Δ[crp-cdt]-10 Δ[zhb: :Tn10] Δcya-12 Δ[zid-62 : :Tn10] | ATCC 55118 |
| χ8203 | cys trp | ATCC 9992V; AMC strain Boxhill 58V |
| χ8204 | cys trp | ATCC 33458; CDC 2862–79 |
| χ8205 | Ty21a galE rpoS cys trp | ATCC 33459; CDC 2861–79 |
| χ8206 | cys trp aroA serC purA155 | ATCC 39926; Stanford 531Ty; derivative of CDC10–80 |
| χ8207 | cys trp | ATCC 10749; AMC 42-A-63 |
| χ8208 | Ty2 cys | ATCC 19430; NCTC 8385 |
| χ8209 | cys trp | ATCC 9993; AMC 42-A-63 |
| MGN-1018 | Ty2 rpoS cys trp ΔphoPQ23 | MEGAN Health Inc., St. Louis, MO |
| MGN-1038 | ISP1820 cys trp ΔphoPQ23 | MEGAN Health, Inc., St. Louis, MO |
| MGN-1191 | ISP1820 cys trp ΔphoPQ23 ΔasdA16 | MEGAN Health, Inc., St. Louis, MO |
| MGN-1256 | Ty2 rpoS cys ΔphoPQ23 ΔasdA16 | MEGAN Health, Inc., St. Louis, MO |
| χ8280 | MGN-1256 (pYA3167) | |
| χ8281 | MGN-1191 (pYA3167) | |
| χ8434 | Ty2 rpoS+ cys ΔphoPQ23 | MGN-1018 by introducing recombinant rpoS+ gene from pYA3467 |
| χ8435 | Ty2 rpoS+ cys ΔphoPQ23 ΔasdA16 (pYA3167) | χ8280 by introducing recombinant rpoS+ gene from pYA3467 |
| χ8438 | Ty2 Type E1 rpoS+ cys (RpoS+) | χ3769 by introducing recombinant rpoS+ gene from pYA3467 |
| *Salmonella typhimurium* Strains | | |
| χ3000 | LT2-Z prototroph | Received from C. Turnbough |
| χ3181 | SR-11 pStSR100+ wild type | Isolated by passage from murine Peyer's patch. Gulig and Curtiss, Infect. Immun. 65:2891–2901 (1987). |
| χ3339 | SL1344 pStSL100+ hisG rpsL, colicin+ | Animal passaged isolate of SL1344, isolated from liver of moribund mouse after p.o. infection. Gulig and Curtiss, Infect. Immun. 65:2891–2901 (1987). |
| χ3340 | SL1344 pStSL100− hisG rpsL, colicin+ | Virulence plasmid-cured derivative of χ3339; Gulig and Curtiss, Infect. Immun. 65:2891–2901 (1987). |
| χ3420 | SL1344 hisG rpsl xyl fli-8007: :Tn10 | P22HTint (χ3376)→χ3339 with selection for Tc$^R$ Mot$^-$ Fla$^-$. |
| χ3422 | SR-11 fli-8007: :Tn10 | P22HTint (χ3376)→χ3181 with selection for Tc$^r$ Mot$^-$ Fla$^-$ |
| χ3679 | SR-11 ΔaroA554 | P22HTint (χ3678)→χ3181 selecting Tc$^r$ and screening for Aro$^-$ followed by selection for tetracycline sensitivity, Aro$^-$. |
| χ3761 | UK-1 wild-type prototroph | ATCC 68169; splenic isolate from infected chick. |
| χ4937 | UK-1 rpoS: :RR10 | P22HTint (SF1005)→χ3761 with selection for ampicillin resistance |
| χ4973 | SL1344 pStSL100+ hisG rpsL rpoS: :RR10, colicin+ | Nickerson and Curtiss, Infect. Immun., 65:1814–1823 (1997) |
| χ8125 | SL1344 pStSL100− hisG rpsL rpoS: :RR10, colicin+ | P22HTint (SF1005)→χ3340 with selection for ampicillin resistance; Nickerson and Curtiss, Infect. Immun., 65:1814–1823 (1997) |
| χ8214 | UK-1 rpoS: :RR10 Δcya-27 Δcrp-27 | P22HTint (SF1005)→χMGN-431 with selection for ampicillin resistance |
| χ8215 | SR-11 rpoS: :RR10 ΔaroA554 | P22HTint (SF1005)→χ3679 with selection for ampicillin resistance |
| χ8217 | UK-1 rpoS: :RR10 Δcya-27 | P22HTint (SF1005)→MGN-232 with selection for ampicillin resistance |
| χ8296 | SL1344 pStSL100+ Δcya-28 Δcrp-27 ΔasdA16 (RpoS+) | MEGAN Health, Inc.; χ3339 derivative with three defined deletion mutations |
| χ8309 | SL1344 pStSL100t Δcya-28 Δcrp-27 ΔasdA16 rpoS (RpoS−) | P22HTint (χ4973)→χ8296 |
| MGN-232 | UK-1 Δcya-27 | MEGAN Health, Inc.; defined cya deletion derivative of χ3761 |
| MGN-431 | UK-1 Δcya-27 Δcrp-27 | MEGAN Health, Inc.; defined crp deletion derivative of MGN-232 |
| ATCC 14028s | prototroph, Tet$^s$ | wild-type invasive strain obtained from F. Heffron |
| SF1005 | 14028s rpoS: :RR10 | F. Fang, Univ. Colorado Health Sci. Center |

TABLE 1-continued

Microorganisms

| Strain Designation | Relevant Genotype | Source/Reference/Derivation |
|---|---|---|
| *Shigella flexneri* 2a Strains | | |
| 3457T | wild-type | Curtiss collection |
| 15D | Δasd::kan | Sizemore et al. (Science, 270:299–302, 1995; Vaccine 15:804–807, 1997) |
| *E. coli* Strains | | |
| χ6101 | K-12 DH5α F⁻ Ø80d lacZ ΔM15 Δ(lacZYA-argF)-4169 gln44 λ⁻ gyrA recA1 relA1 endA1 hsdR17 ($r_k-$, $m_k+$) | Guy Cardineau, Sungene Technologies, Inc., San Jose, CA |
| χ6212 | K-12 F⁻ Ø80d lacZ ΔM15 Δ(lacZYA-argF)-4169 supE44 λ⁻ gyrA recA1 relA1 endA1 ΔasdA4 Δ[zhf-2::Tn10] hsdR17 ($r_k-$, $m_k+$) | This lab |
| MGN-026 | K-12 F⁻ Ø80d lacZ ΔM15 Δ(lacZYA-argF)-4169 supE44 λpir gyrA recA1 relA1 endA1 hsdR17 ($r_k-$, $m_k+$) | λpir→χ6101; MEGAN Health, Inc., St. Louis, MO |
| MGN-617 | thi-1 thr-1 leuB6 supE44 tonA21 lacY1 recA RP4-2-Tc::Mu λpir, ΔasdA4 Δ[zhf-2::Tn10] | MEGAN Health, Inc., St. Louis, MO |

TABLE 2

Phages and Plasmids

| | Description | Source/Reference |
|---|---|---|
| Bacteriophage | | |
| P22HTint | high frequency generalized transducing mutant of the temperate lambdoid phage P22 | Schmeiger, Mol. Gen. Genet. 119:75–88, 1972; Jackson et al., J. Mol. Biol. 154:551–563, 1982; Ray et al., Mol. Gen. Genet. 135:175–184, 1974. |
| P22 H5 | clear plaque forming mutant of P22HTint | Casjens et al., J. Mol. Biol. 194:411–422, 1987. |
| Plasmids | | |
| psK::rpoS | *S. typhimurium* 14028 rpoS+ gene cloned into the EcoRV site of pBlueScript/SK | F. Fang, Univ. Colorado Health Sci. Center |
| pMEG-003 | pir-dependent R6K ori Tc$^r$ asd+ | MEGAN Health, Inc., St. Louis, MO |
| pMEG-006 | pir-dependent R6K ori Tc$^r$ ΔasdA16 | Megan Health, Inc., St. Louis, MO |
| pMEG-068 | Contains phoQ gene | MEGAN Health, Inc., St. Louis, MO |
| pMEG-149 | Amp$^R$ mobilizable pir-dependent suicide vector; containing the sacBR genes from *B. subtillis*, RK2 mob, R6K ori | MEGAN Health, Inc., St. Louis, MO |
| pMEG-210 | phoQ deletion of pMEG-068 | MEGAN Health, Inc., St. Louis, MO |
| pMEG-213 | Derivative of pMEG-149 containing phoPQ23 defined deletion of pMEG-210 | MEGAN Health, Inc., St. Louis, MO |
| pMEG-328 | Derivative of pNEB-193 containing the *S. typhimurium* UK-1 rpoS+ gene cloned into the Bam HI and XbaI sites | MEGAN Health, Inc., St. Louis, MO |
| pMEG-375 | cat gene from pACYC184 cloned into pMEG-149 | MEGAN Health, Inc., St. Louis, MO |
| pNEB-193 | pUC19 derivative that carries single restriction sites for unique 8bp cutters AscI, PacI and PneI within the polylinker region | New England Biolabs |
| pYA3167 | asd-complementing plasmid; expresses the Hepatitis B virus (HBV) nucleocapsid pre-S1 and pre-S2 epitopes on HBV core | Nardelli-Haefliger et al., Infect. Immun. 64:5219–5224, 1996 |
| pYA3342 | Asd+ cloning vector with pBR replicon | This lab |
| pYA3433 | contains rpoS+ gene cloned from pSK::rpoS into SmaI site of pMEG-149 | This lab |
| pYA3467 | contains *S. typhimurium* UK-1 rpoS+ gene from pMEG-328 cloned into PmeI and Sma I sites of pMEG-375 | This lab |

Bacterial strains were maintained as duplicate −70° C. frozen cultures suspended in 1% Bacto-peptone (Difco) containing 5% glycerol and were also stored at −20° C. in 1% Bacto-peptone and 50% glycerol for routine use. Bacteria were generally cultured in L Broth (Lennox, *Virology*

1:190–206, 1965) or Luria Broth (Luria et al., *J. Bacteriol.* 74:461–476, 1957). Agar plates contained 1.5% Difco Agar. Carbohydrate utilization was evaluated by supplementing MacConkey (Difco) or Eosin Methylene Blue agar base (Curtiss, *Genetics* 58:9–54, 1968) with 1% final concentration of an appropriate carbohydrate. Minimal liquid (ML) and minimal agar (MA) were prepared as described in Curtiss (*J. Bacteriol.* 89:28–40, 1965) and supplemented with nutrients at optimal levels. Buffered saline with gelatin (BSG) was used routinely as a diluent (Curtiss, 1965 supra).

Bacteriophage P22HTint was used for transduction using standard methods (Davis et al., A Manual for Genetic Engineering—Advanced Bacterial Genetics, Cold Spring Harbor Laboratory Press, Cold Spring Harbor, N.Y., 1979). An overnight culture of a donor strain was diluted 1:20 into prewarmed Luria broth, grown for one hour with shaking at 37° C., and then infected with P22HTint at a multiplicity of infection (MOI) of 0.01. The infection mixture was shaken overnight or for approximately fifteen hours. A few drops of chloroform were added to ensure complete bacterial cell lysis, and the mixture was allowed to shake an additional ten minutes at 37° C., then centrifuged at 7,000 rpm in a Sorvall SS-34 rotor for ten minutes to remove bacterial debris. The supernatant fluid was extracted and removed to a clean tube with a drop or two of fresh chloroform and stored at 4° C. This method generally provides a phage lysate containing about $10^{10}$ PFU/ml titered on χ3000. Tetracycline was used in plates at 12.5 µg/ml to select for Tn10 transductants, Tn10-induced mutations, or merodiploid strains expressing the Tn10-derived tetracycline-resistance genes from a chromosomally integrated suicide vector. The Tn10 transposon excises from the chromosome at a low frequency, often deleting a portion of the genome flanking the transposon. Cells which undergo an excision event also become sensitive to tetracycline, and can be identified by plating on media containing fusaric acid, which kills tetracycline-resistant bacteria (Maloy and Nunn, *J. Bacteriol.* 145:1110–1112, 1981). Tetracycline-sensitive strains which have lost an integrated suicide plasmid along with the plasmid linked tetracycline-resistance genes can also be selected on fusaric acid media.

Tetracycline-resistant cultures were grown standing overnight in L broth containing 12.5 µg/ml tetracycline at 37° C. to approximately $5 \times 10^8$ CFU/ml. These cultures were diluted 1:40 into prewarmed L broth without tetracycline and aerated at 37° C. to a titer of about $2 \times 10^9$ CFU/ml, serially diluted into BSG, and plated from these dilutions onto fusaric acid media. Fusaric acid resistant colonies were selected after incubation for 48 hours at 37° C. Fusaric acid resistant isolates were restreaked to fusaric acid media, then patched to Penassay agar (Difco) with and without tetracycline to confirm the loss of the Tn10-derived antibiotic resistance element. Other phenotypes were scored where indicated using appropriate media.

Suicide vectors containing an ampicillin-resistance gene, a sucrose-utilization cassette, and an incP mobilization site were constructed. Mutant genes which have been introduced into these plasmids can be introduced into the bacterial chromosome after transformation, or preferably by conjugation, to generate ampicillin-resistant (100 µg/ml) merodiploids. Such merodiploids can be grown on media containing 5% sucrose to select for the loss of the integrated plasmid along with the ampicillin-resistance and sucrose-utilization genes. Ampicillin-sensitive strains can be phenotypically characterized for the presence of appropriate defined deletion mutant alleles.

Improved selection of merodiploids can be achieved by introducing a cat gene conferring resistance to chloramphenical (40 µg/ml) in addition to an ampicillin-resistance gene on the suicide vector. After merodiploid formation, selection on media with 5% succrose leads to loss of both drug-resistance genes and the succrose-utilization genes. These recombinants can then be screened for the desired allele replacement.

EXAMPLE 1

This example illustrates the role of the rpoS gene in efficient invasion and colonization of the GALT by *S. typhimurium* using an rpoS mutant strain, χ4973, compared to its wild-type parent, χ3339.

Strain Construction:

χ3339 is a wild-type, virulent, animal-passaged isolate of *S. typhimurium* strain SL1344 described in Gulig et al. (*Infect Immun* 55:2891–2901, 1987). SF1005 is an rpoS:: RR10 mutant derived from *S. typhimurium* strain ATCC 14028s and containing an ampicillin resistance gene linked to the rpoS::RR10 mutant allele (Fang et al., *Proc. Nat'l. Acad. Sci., USA* 89:11978–11982, 1992). The mutant rpoS:: RR10 allele was moved into χ3339 using a P22HTint transducing phage lysate prepared on SF1005 and selecting for ampicillin resistance ($Ap^r$) due to the presence of the β-lactamase gene (bla) linked to the RR10 insertion in the rpoS gene. The allelic exchange between SF1005 and χ3339 was confirmed by Southern blot analysis, and the resulting χ3339 rpoS::RR10 mutant derivative was designated as χ4973. Transductants were screened for sensitivity to P22HTint by cross streaking with P22H5, a clear plaque mutant. Pseudolysogenic colonies were distinguished from non-lysogens on Evans blue and uranine (EBU) indicator agar (Sternberg et al., *Meth. Enzymol.* 204:2–43, 1991). Media were supplemented with 50 µg ampicillin per ml when required to select for χ4973.

The presence of smooth lipopolysaccharide (LPS) in χ4973 was confirmed using the method of Hitchcock et al. (*J. Bacteriol.* 154:269–277, 1983). LPS was silver stained by the method of Tsai et al. (*Anal Biochem* 119:115–119, 1982). This experiment showed that the mutation in rpoS did not affect LPS structure.

Virulence of an RpoS Mutant in Mice:

The virulence of χ3339 was compared to that of the rpoS mutant strain χ4973 upon oral inoculation of eight- to ten-week old female BALB/c mice. Animal inoculation for the determination of the fifty per cent lethal dose ($LD_{50}$) was performed as described earlier with minor modifications (Gulig et al., *Infect Immun* 55:2891–2901, 1987). Mice were deprived of food and water for four to six hours prior to peroral inoculation. Gastric acidity was not neutralized prior to infection. $LD_{50}$ titers were determined according to the method of Reed and Muench (*Am. J. Hyg.* 27:493–497, 1938) for each strain using results obtained from four mice per inoculum dose evaluated for a period of thirty days.

The peroral $LD_{50}$ for the rpoS mutant strain χ4973 was greater than $8 \times 10^9$ colony forming units per dose. This value represented more than a four log increase over the oral lethal dose of $8 \times 10^5$ colony forming units observed for the wild-type parent strain χ3339. This result is consistent with Fang et al., supra, who reported a three log increase in the oral $LD_{50}$ dose for SF1005, as compared to the $rpoS^+$ parent strain ATCC 14028s. Further studies were then conducted to determine why the rpoS mutant strain was attenuated compared to its wild-type parent.

Comparative Testing of Attachment, Invasion and Survival:

Human embryonic intestinal epithelial cell line Int-407 (Henle et al., *J. Immunol.* 79:54–59, 1957) and murine macrophage-like cell line J774 (Ralph et al., *Nature* 257:393–394, 1975) were used to examine the effect of rpoS on the adherence and invasive abilities of *S. typhimurium*. Each cell line was maintained in Minimal Essential Medium (MEM; GibcoBRL, Grand Island, N.Y.) containing Hank's Balance Salt Solution (HBSS; GibcoBRL), 2 mM glutamine, and 10% fetal calf serum (FCS; HyClone, Logan, Utah) at 37° C. in an atmosphere containing 5% $CO_2$. Cells were passaged every two to three days with medium changes. Macrophage monolayers used in an infection assay were prepared by gently scraping passaged cells into solution, diluting the cell suspension, inoculating wells of a 24-well microtiter dish, and incubating at 37° C. in a 5% $CO_2$ environment. Int-407 cells were distributed in a similar fashion, but were trypsinized for removal from monolayers.

Bacterial attachment and invasion assays using cells from the human intestinal epithelial cell line, Int-407, and the mouse macrophage-like cell line, J774, followed methods according to Galan et al., *Proc Natl Acad Sci, USA* 86:6383–6387, 1989, with minor modifications. Bacteria were grown as static cultures in L broth at 37° C. to mid log phase or about 0.5 optical density as measured at 600 nm. Because expression of rpoS and RpoS-regulated genes increases as cells enter into stationary phase, a control culture was also grown statically for four days to saturation in order to establish the maximal level of rpoS expression. Bacterial cultures were washed and resuspended in HBSS immediately prior to infection of monolayers. Int-407 monolayer attachment and invasion was allowed to proceed for two hours at 37° C. in MEM in an atmosphere of 5% $CO_2$ and at an MOI of between two and ten bacterial cells per Int-407 cell. Attachment and invasion assays using J774 cells were performed as with Int-407 cells, except that only one hour was allowed for adherence and invasion. As a control for distinguishing adhesion from phagocytosis of bacterial cells by the monolayer cells, J774 cells were monitored at 4° C. in the presence of bacteria according to the method of Lee et al., *Proc. Nat'l. Acad. Sci., USA* 87:4304–4308, 1990.

Infected monolayers were washed three times with isotonic phosphate-buffered saline (PBS) after the attachment and invasion incubation, and then lysed with PBS containing 0.1% sodium deoxycholate to assess the total number of bacteria associated with the cultured cells. Duplicate monolayers infected in parallel were incubated an additional two hours with MEM containing 10 μg/ml gentamicin in order to kill extracellular bacteria prior to lysis so that the number of internalized bacteria could be enumerated. Viable bacterial cell counts were obtained by plating dilutions of lysed monolayers onto L agar and incubating at 37° C. for eighteen to twenty four hours. Results are shown in Tables 3 and 4 below.

TABLE 3

Effect of an rpoS: :RR10 mutation on adherence to and invasion of Int-407 cells by *S. typhimurium* χ3339 and its rpoS mutant derivative, χ4973[a]

| Strain | Growth phase | Percent adhesion[b] | Percent invasion[c] |
|---|---|---|---|
| χ3339 | Exponential | 59.2 ± 0.3 | 83.0 ± 26.9 |
| χ4973 | Exponential | 51.4 ± 0.2 | 88.0 ± 22.0 |
| χ3339 | Stationary | 12.8 ± 2.3 | 25.0 ± 2.4 |
| χ4973 | Stationary | 34.0 ± 18.0 | 50.0 ± 4.0 |

[a]The data are given as the means ± SEM for three trials.
[b]Percent of inoculum adherent to cells after incubation for 2 hours.
[c]Percent of inoculum recovered after incubation for 2 additional hours in gentamicin [10 μg/ml].

TABLE 4

Effect of an rpoS: :RR10 mutation on the adherence to and invasion of J774 cells by *S. typhimurium* χ3339 and its rpoS mutant derivative, χ4973[a]

| Strain | Growth phase | Percent adhesion[b] | Percent invasion[c] |
|---|---|---|---|
| χ3339 | Exponential | 55 ± 4.1 | 66 ± 3.7 |
| χ4973 | Exponential | 57 ± 1.5 | 46 ± 4.4 |
| χ3339 | Stationary | 44 ± 3.2 | 14 ± 3.5 |
| χ4973 | Stationary | 19 ± 2.4 | 11 ± 0.3 |

[a]The data are given as the means ± SEM for three trials.
[b]Percent of inoculum adherent to cells after incubation for 1 hour.
[c]Percent of inoculum recovered after incubation for 2 additional hours in gentamicin [10 μg/ml].

When the *S. typhimurium* strains were grown to exponential phase, the rpoS::RR10 mutant, χ4973, attached to Int-407 and J774 cells to the same extent as its wild-type parent, χ3339 (Tables 3 and 4). Percent invasion was also the same for both strains in the intestinal epithelial cell line, Int-407 (Table 3). However, invasion showed a small decrease with the rpoS::RR10 mutant in the macrophage cell line, J774, compared to the wild-type parent (Table 4). These data indicate that when the *S. typhimurium* were in the exponential growth phase, the rpoS gene contributed little or nothing to the ability of the bacteria to attach to or invade into the cells. When the bacterial cells were in the stationary phase, however, results were equivocal. Whereas adhesion and invasion were slightly increased with rpoS::RR10 mutants grown to stationary phase in Int-407 cells, adhesion was slightly decreased for the rpoS::RR10 mutants grown to stationary phase in J774 cells (Tables 3 and 4, respectively). In additional studies not shown, no difference was observed in the ability of these strains to adhere to or invade into J774 cells when assays were conducted at 4° C. (data not shown). These data indicate that the rpoS gene product has little or no effect on in vitro attachment to or invasion of intestinal epithelial cells and macrophage-like cells during the exponential and stationary growth phases of *S. typhimurium* and are consistent with what has been reported for SL1344-derived *S. typhimurium* containing an altered rpoS allele from *S. typhimurium* LT-2 (Wilmes-Riesenberg et al., *Infec. Immun.* 65:203–210, 1997).

*S. typhimurium* bacteria having an rpoS mutation were also able to survive when internalized in J774 murine macrophage-like cells or rat bone-marrow derived macrophages. Rat bone-marrow derived macrophages were obtained from the femurs and tibias of Sprague Dawley rats (Harlan Sprague Dawley, Indianapolis, Ind.) and grown in a 75 $cm^2$ flask containing Dulbecco Minimal Essential Medium (DMEM; GibcoBRL, Grand Island, N.Y.) containing 10% fetal calf serum (FCS), 100 units penicillin/ml and 100 µg streptomycin/ml for 10 days. The macrophages were then cultured in DMEM containing 10% fetal calf serum (FCS), 5% horse serum (HS; Sigma, St. Louis, Mo.), 10% L-cell-conditioned medium, 1 mM glutamine, and 1% penicillin for twenty four hours at 37° C. in an environment containing 5% $CO_2$. Nonadherent cells were removed, spent medium was replaced, and the cells were incubated an additional five days. Macrophages were gently scraped from the surface of the flask, resuspended in fresh DMEM supplemented with 10% FCS, 5% HS and 10% L-cell conditioned medium without antibiotics and used to seed wells of a 24-well microtiter plate prior to infection experiments, at a concentration of $5 \times 10^5$ or $1 \times 10^6$ cells per ml of rat bone marrow-derived macrophages or J774 cells, respectively.

χ3339 or χ4973 were grown to stationary phase as described above and used in an intracellular survival assay in J774 cells or rat bone-marrow derived macrophages according to Buchmeier et al., *Infect. Immun.* 57:1–7, 1989, with minor modifications. Bacteria were opsonized with 10% normal mouse serum for thirty minutes prior to infection of the monolayers prepared above at a multiplicity of infection (MOI) of between two and ten bacteria per cell. Infected monolayers were incubated for twenty minutes to allow for invasion or phagocytosis, and then washed two times with PBS to remove bacteria remaining in solution phase. Fresh growth media containing 10 µg/ml gentamicin was added to washed, infected monolayers to eliminate extracellular bacterial growth. Infected monolayers were incubated for the indicated times after gentamicin addition, washed to remove traces of antibiotic, and then lysed with 0.1% sodium deoxycholate in PBS. Dilutions of lysates were plated onto L agar and incubated at 37° C. for twenty four to thirty six hours in order to enumerate surviving intracellular bacteria.

Figure 1:
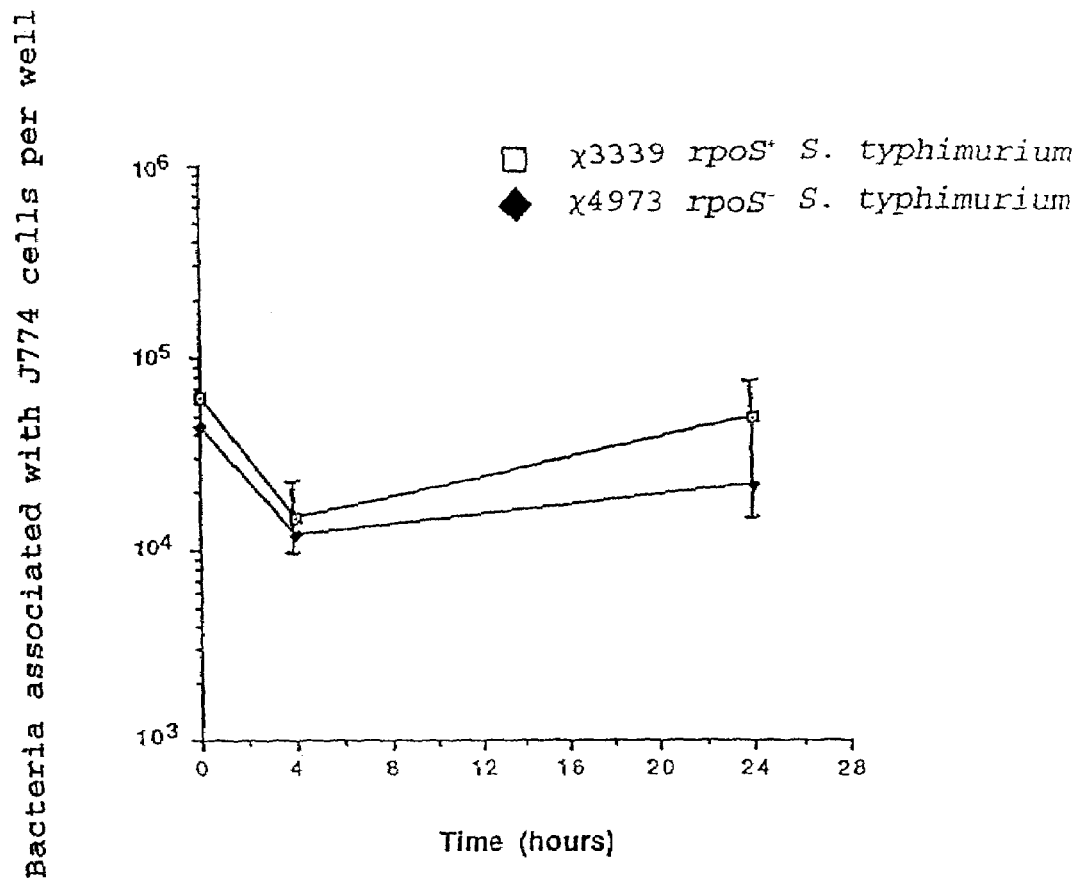
Figure 2:
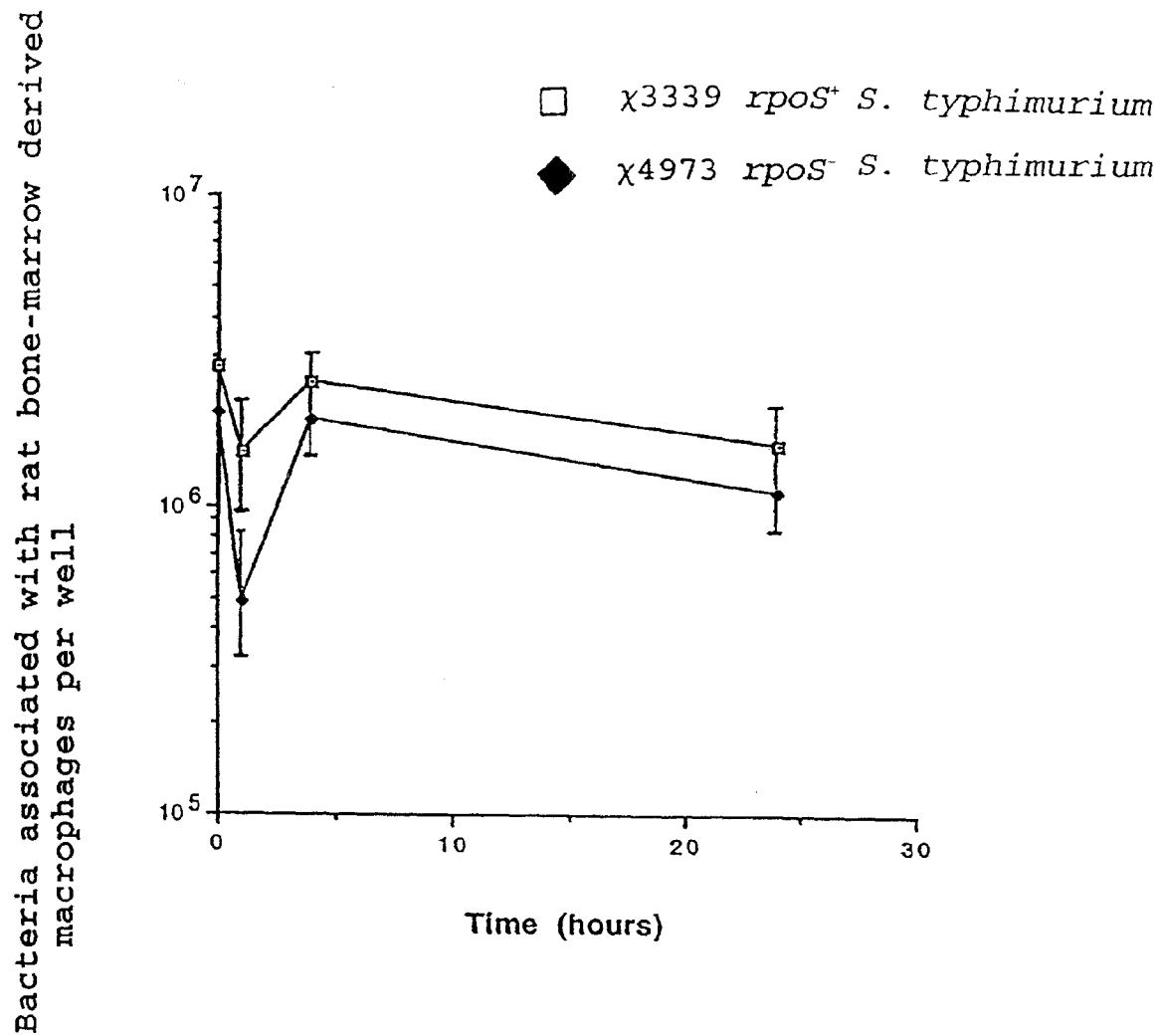

FIGS. 1 and 2 illustrate the log of the mean and standard deviations of counts of bacteria associated with cells obtained from three wells over the time course of 24 hours. Both χ3339 and χ4973 exhibited a decrease in bacterial cell count during the first two to four hours, followed by an increase in cell count during the next 20 hours in J774 cells. However, a decrease in the viable number of these bacteria was observed between 4 and 20 hours in rat bone marrow macrophages, yet significant numbers of bacteria survived during the course of the study with little difference between the rpoS wild-type or rpoS mutant strains. Thus, *S. typhimurium* rpoS mutants are able to survive in either murine macrophage-like J774 cells or in rat bone marrow-derived macrophages as well as their wild-type parent, indicating that the rpoS gene product plays little or no role in the survival of the microbe in these macrophages.

Tissue Distribution of rpoS Mutants After P.O. Infection:

To compare the GALT colonization abilities of the rpoS::RR10 mutant and wild-type strains, animal infectivity studies were performed.

Bacteria used in these studies were grown aerobically in a volume of 100 ml L broth at 37° C. to an optical density of 0.8 as measured at 600 nm. Bacteria were harvested by centrifugation for ten minutes at 7,000 rpm. The cell pellet was resuspended in 1 ml buffered saline with gelatin (BSG).

Eight- to ten-week old female BALB/c mice purchased from Charles River Laboratories (Wilmington, Mass.) were either coinfected with both the χ4973 rpoS mutant and χ3339 wild-type strains or individually infected with each strain. In each of the coinfection and individual infection experiments, four groups of three mice each were perorally inoculated with approximately equal numbers of bacteria. Mice were euthanized by $CO_2$ asphyxiation at one hour and at one, three and five days after oral inoculation. Organs and tissues of interest were aseptically removed and homogenized with a tissue homogenizer (Brinkman Instruments). Five to ten lymphoid follicles representing the Peyer's patches were collected from each mouse and combined before homogenization. Homogenates were diluted into BSG and plated onto MacConkey/1% lactose agar with and without ampicillin. This allows a comparison between the total number of both wild-type and rpoS mutant *Salmonella typhimurium* which successfully colonize the tissues, to the total number of rpoS mutant bacteria which successfully colonize the same tissues. The data for the coinfection and individual infection experiments are shown below in Tables 5 and 6, respectively.

TABLE 5

Ratios of *S. typhimurium* wild-type to rpoS mutants in mouse tissues after peroral coinfection[a]

| Time after infection | Intestinal Contents | Intestinal Wall[b] | Peyer's Patches | Spleen | Liver |
|---|---|---|---|---|---|
| 1 hour | 1.7 ± 0.4 | 1.7 ± 0.5 | N.D.[c] | N.D.[c] | N.D.[c] |
| 1 day | 2.1 ± 0.4 | 1.5 ± 0.1 | 1.1 ± 0.10 | N.D.[c] | N.D.[c] |
| 3 days | 2.1 ± 0.1 | 8.7 ± 4.3 | 10.9 ± 5.4 | 815 ± 743 | 122 ± 38 |
| 5 days | 2.7 ± 0.2 | 6.0 ± 4.2 | 469 ± 325 | 250,000 ± 249,800 | 11,750 ± 10,250 |

[a]Approximately equal numbers of χ3339 (wild-type) and χ4973 rpos (4.5 × 10$^9$ and 4.0 × 10$^9$ colony forming units (CFU) , respectively) were administered perorally to 10-week old BALB/c mice. Mean ratios of CFU/g of tissue for χ3339/χ4973 ± SEM (n = 3) are given. Only bacterial counts greater than 20 CFU/g were considered when calculating the ratios.
[b]Small and large intestine with Peyer's patches removed.
[c]N.D., bacterial numbers were not determined.

TABLE 6

Colonization of mouse tissues after individual infection with *S. typhimurium* wild-type or rpoS mutant strains[a]

| Time[b] | Tissue | Bacterial numbers χ3339 | (cfu/g tissue) χ4973 |
|---|---|---|---|
| Day 3 | Wall[c] | 2.1 × 10$^3$ ± 1.2 × 10$^3$ | 2.7 × 10$^3$ ± 6.4 × 10$^2$ |
|  | Peyer's patches | 1.7 × 10$^5$ ± 4.1 × 10$^4$ | 5.8 × 10$^4$ ± 1.1 × 10$^4$ |
| Day 5 | Wall[c] | 1.9 × 10$^4$ ± 6.6 × 10$^3$ | 6.5 × 10$^3$ ± 2.5 × 10$^3$ |
|  | Peyer's patches | 9.9 × 10$^5$ ± 2.4 × 10$^5$ | 4.5 × 10$^4$ ± 1.6 × 10$^4$ |

[a]Ten-week old BALB/c mice were administered perorally with either wild-type χ3339 (2.7 × 10$^9$ CFU) or rpoS mutant χ4973 (1.1 × 10$^9$ CFU) bacteria. Only bacterial counts greater than 20 CFU/g were considered significant.
[b]The intestinal wall and the Peyer's patches were excised after the indicated time. Three mice were euthanized at each time point. Standard errors are shown for each experiment.
[c]Small and large intestine with Peyer's patches removed.

The rpoS mutant strain χ4973 and the wild-type strain χ3339 initially colonized the gastrointestinal tract with similar efficiency as judged by the numbers of bacteria associated with the intestinal wall at day three in both mixed (Table 5) and individual (Table 6) infections. Thus the rpoS mutants survived passage through the stomach as well as the wild-type parent strain.

However, the rpoS mutant strain χ4973 was much less efficient in colonizing the Peyer's patches as compared to its wild-type parent strain, χ3339 (Tables 5 and 6). This disadvantage of the rpoS strain was even more pronounced in the spleen (Table 5). Thus, the S. typhimurium strain with the rpoS mutant allele is defective in its ability to colonize the GALT and the spleen, which are two primary lymphoid organs in which immune responses are elicited.

To determine whether the rpoS gene product regulates expression of chromosomally-encoded genes whose products are important for S. typhimurium colonization of Peyer's patches, the wild-type χ3339 and rpoS mutant χ4973 strains were cured of their virulence plasmids to generate plasmid-cured isogenic derivatives χ3340 and χ8125, respectively. The ability of these derivative strains to colonize Peyer's patches was examined following peroral administration of χ3340 and χ8125 in a 1:1 ratio and the data are shown in Table 7 below.

TABLE 7

Ratios of wild-type to rpoS mutants for virulence plasmid-cured S. typhimurium in mouse tissues after peroral coinfection[a]

| Time after Infection | Intestinal Contents | Intestinal Wall[b] | Peyer's Patches |
|---|---|---|---|
| 3 days | 37.7 ± 11.8 | 4.4 ± 3.5 | UD[c] |
| 5 days | 3.2 ± 1.2 | 1.2 ± 0.3 | 5.4 ± 0.5 |

[a]Approximately equal numbers of χ3340 and χ8125 (4.0 × 10$^9$ CFU and 3.4 × 10$^9$ CFU, respectively) were administered perorally to 10-week old BALB/c mice. Mean ratios of CFU/g of tissue for χ3340/χ8125 ± SEM (n = 3) are given. Only bacterial counts greater than 20 CFU/g were considered when calculating the ratios.
[b]Small and large intestine with Peyer's patches removed.
[c]Bacterial numbers undetectable at a 1:100 dilution.

As shown in Table 7, χ8125, the RpoS⁻ derivative of χ3340, which in turn is the virulence plasmid-cured derivative of the SL1344 wild-type strain, χ3339, exhibited a reduced ability (ca. 5.4 fold) to colonize Peyer's patches at 5 days postinfection as compared to the colonizing ability of χ3340. These data indicate that RpoS regulates expression of chromosomally-encoded gene(s) whose products are important for successful colonization of murine Peyer's patches after oral inoculation.

Effect of RpoS⁻ Strain on Histology of Peyer's Patches:

Peyer's patches were removed from the intestinal wall of mice at various times after peroral inoculation with χ3339 or χ4973 and were immediately fixed in an ice-cold solution of 1.5% glutaraldehyde and 1.5% paraformaldehyde in a 0.1M sodium phosphate buffer, pH 7.4, followed by fixation in 2.5% glutaraldehyde also in sodium phosphate buffer, pH 7.4 for one hour at room temperature. Thick sliced sections of fixed tissue were stained with Epoxy Tissue Stain (Electron Microscopy Sciences, Fort Washington, Pa.) to locate domes of the Peyer's patches. Thin sliced sections were examined with a Hitachi H-600 transmission electron microscope (TEM) operated at 75 kV accelerating voltage.

Figure 3:
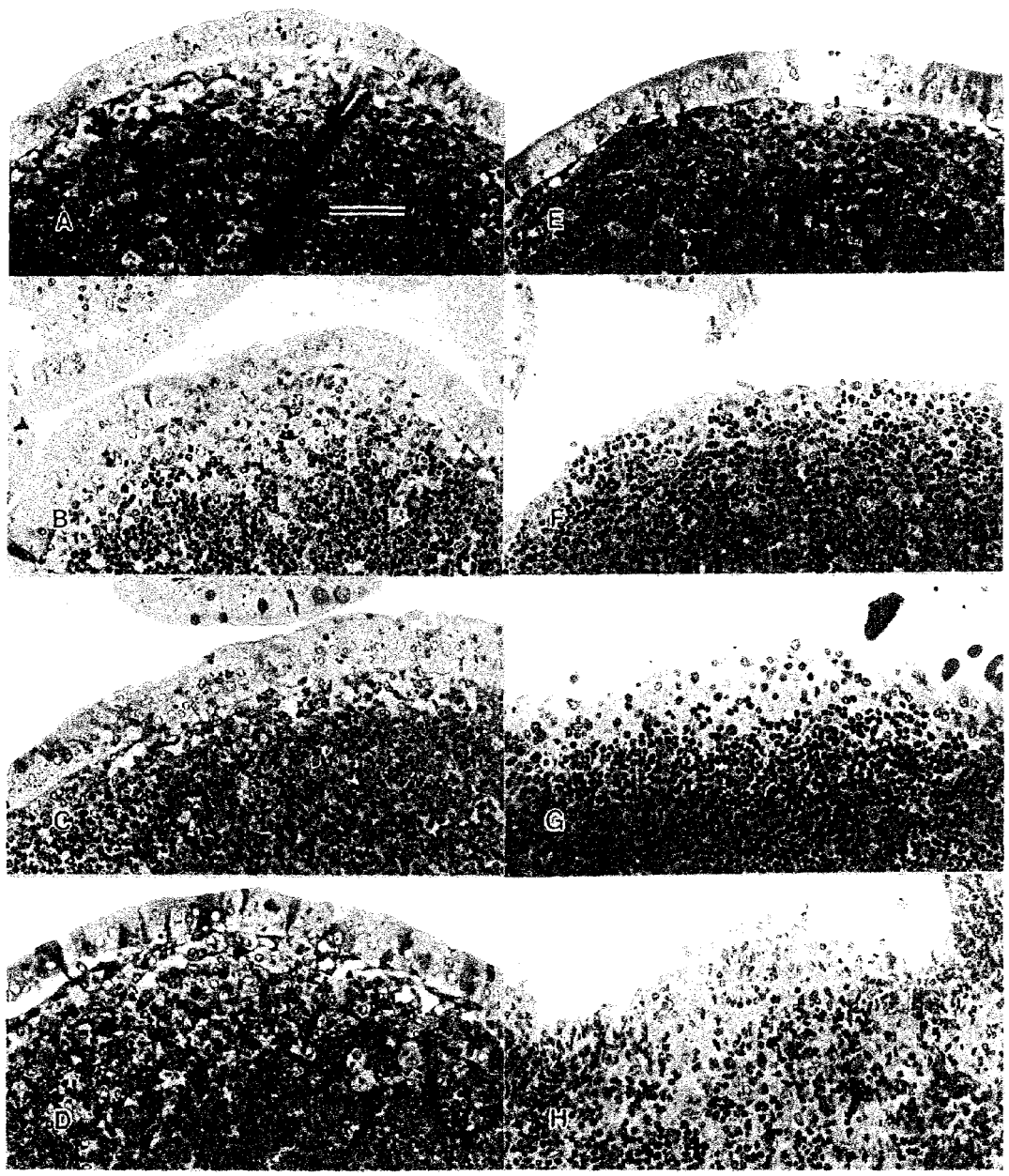
Figure 4:
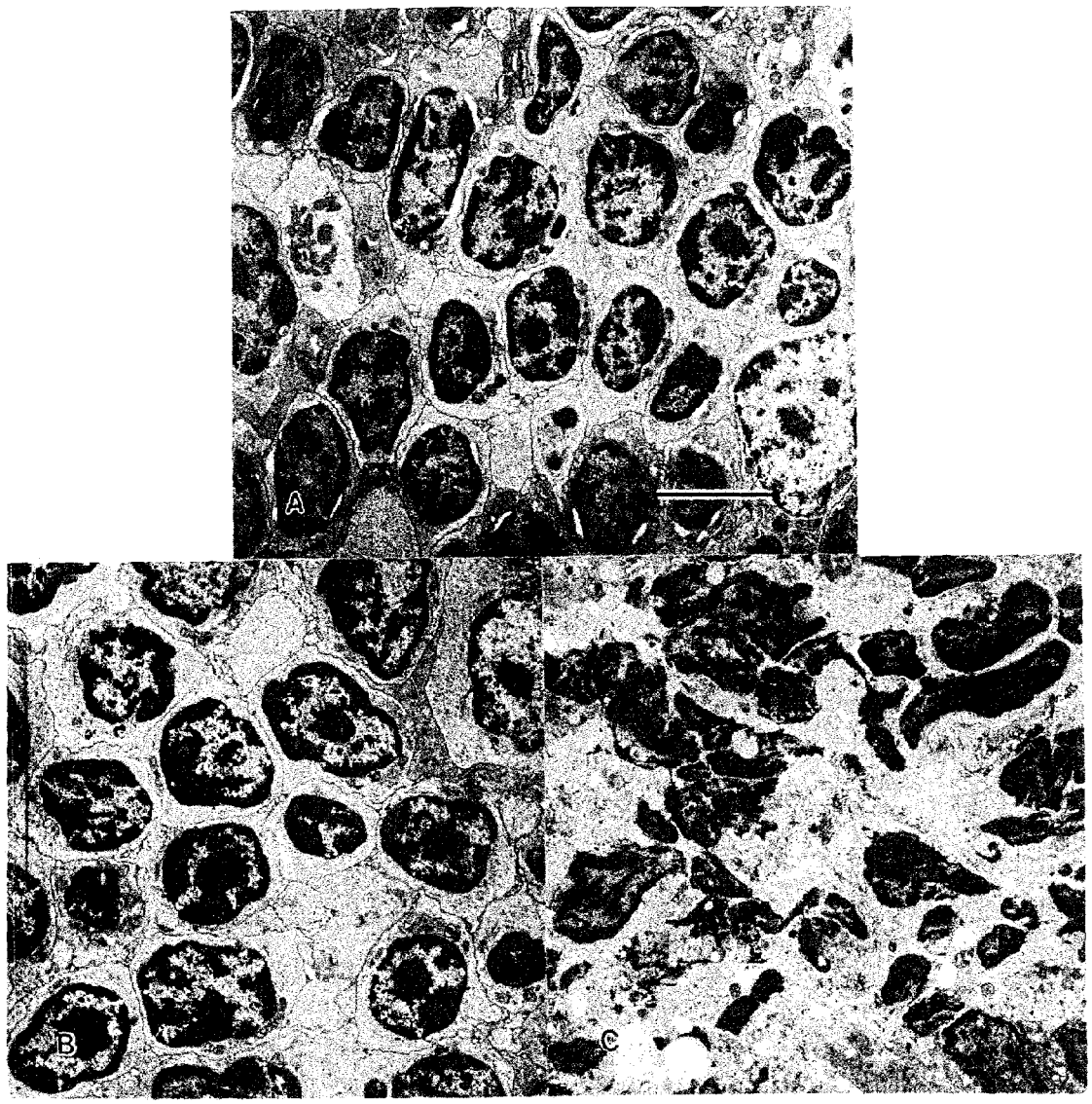

Observation of sections using light or TEM microscopy revealed major morphological changes in the integrity of the Peyer's patch epithelium as early as one day after oral inoculation with the wild-type virulent strain χ3339 (FIGS. 3E and 3F). The destruction of the follicle-associated epithelium (FAE) at three and five days after oral inoculation with χ3339 was even more apparent as seen in FIGS. 3G and 3H. The enterocytes had been completely sloughed from the dome epithelium and extensive tissue necrosis was observed. In addition, there was a dramatic decrease in cell density of the Peyer's patch lymphoid follicle tissue five days after oral inoculation of mice with χ3339 (FIGS. 3h and 4c).

In contrast, Peyer's patches from mice that were uninfected or infected with the rpoS mutant strain χ4973 did not exhibit the dramatic changes in tissue morphology caused by χ3339 infection. Instead, the integrity of the dome epithelium was uncompromised and very little decrease in cell density of the underlying lymphoid tissue was observed at one, three and five days after oral inoculation (FIGS. 3B–3D).

Figure 5:
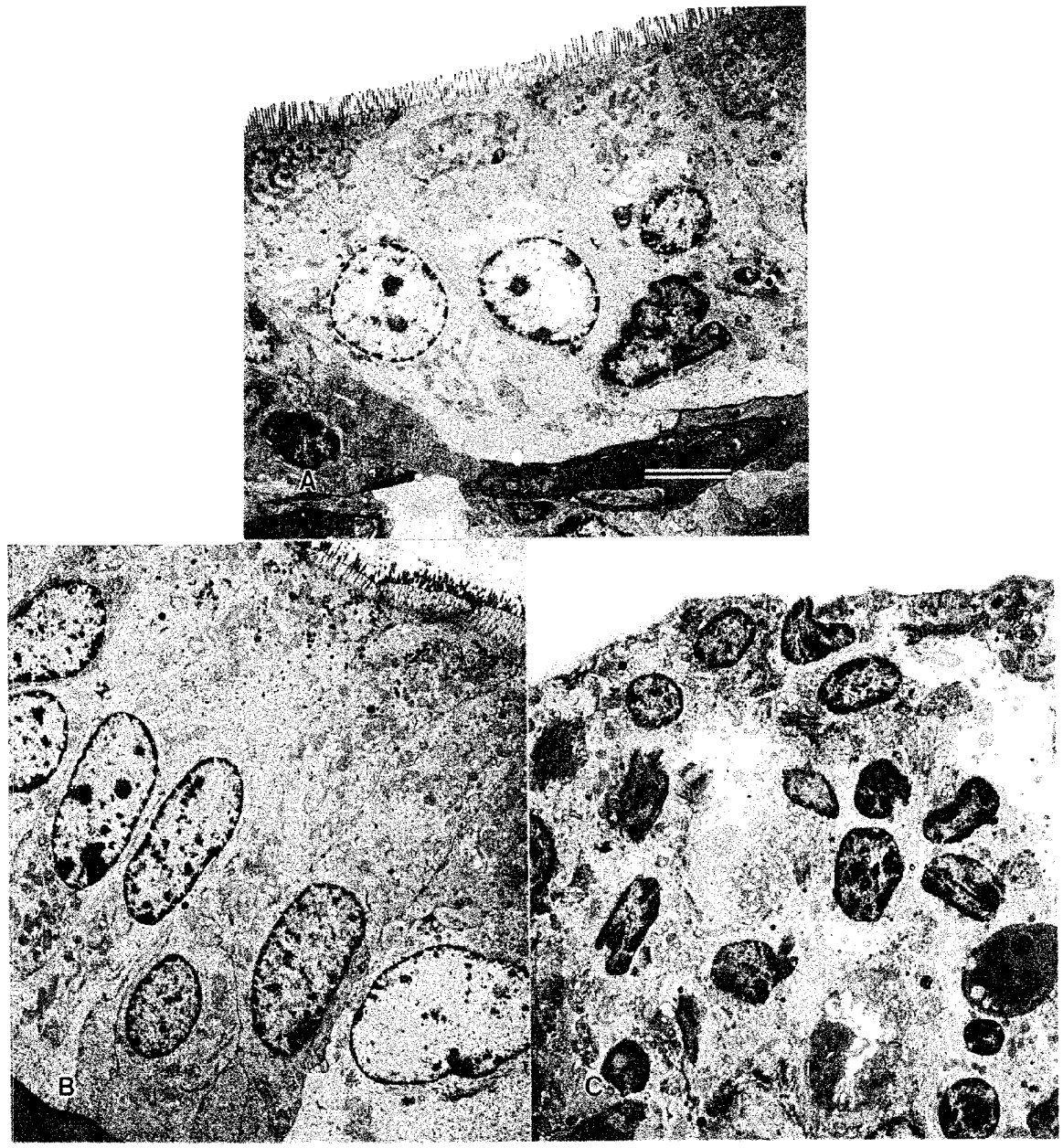
Figure 6:
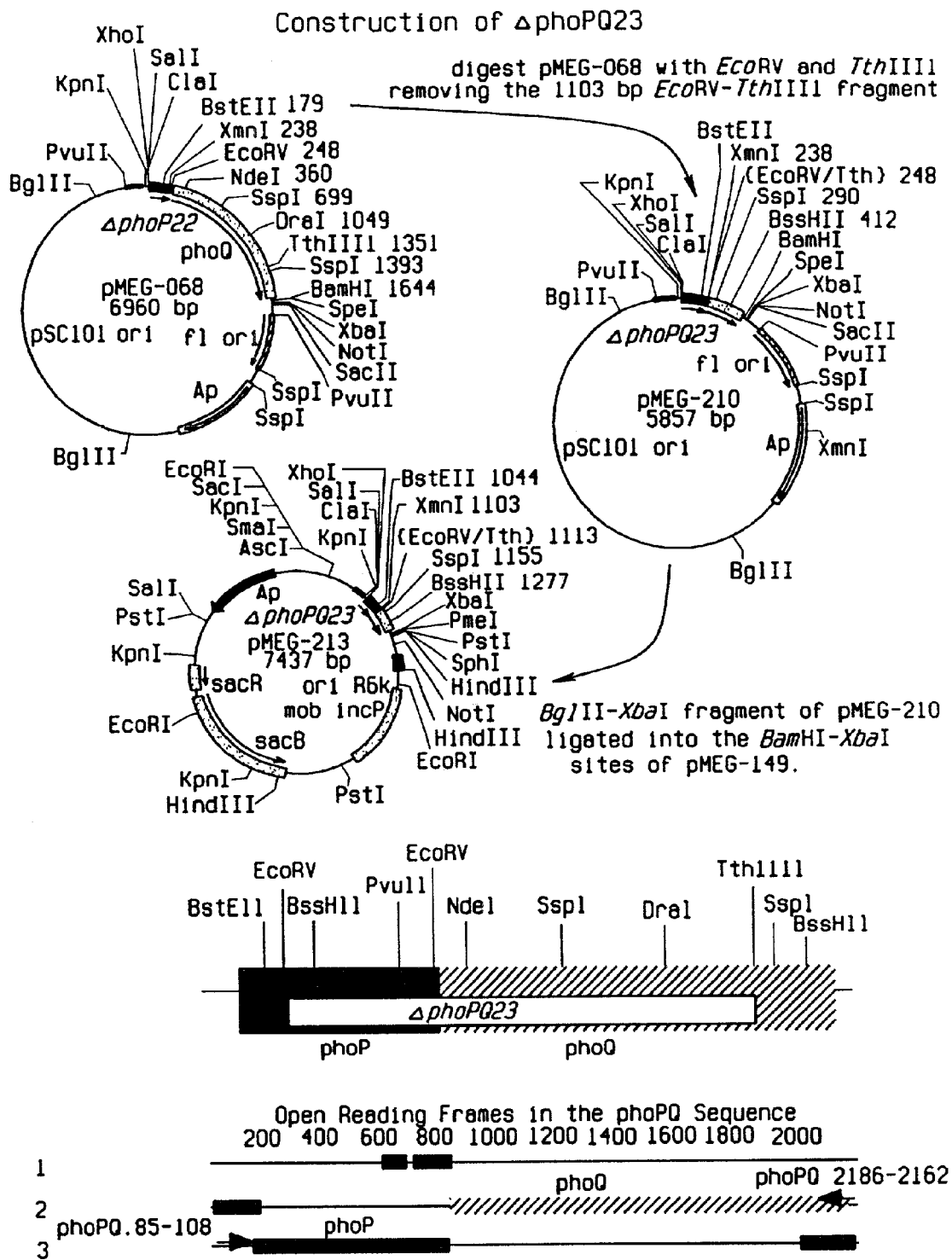
Figure 7:
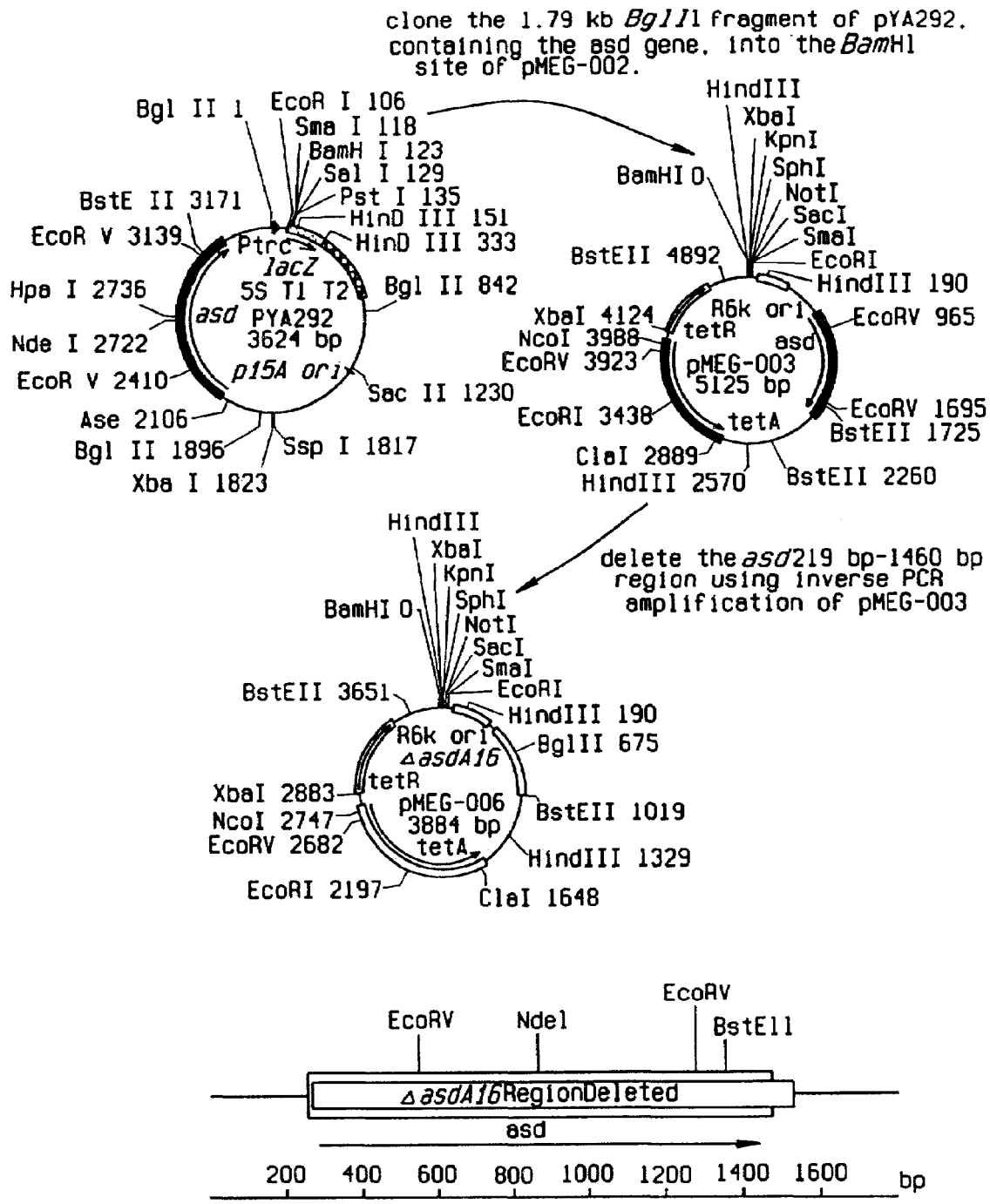

TEM analysis of Peyer's patch tissue before and five days after oral inoculation with the rpoS mutant χ4973 showed that the FAE remained intact (FIGS. 5A and 5B), whereas the FAE was totally destroyed in χ3339 infected Peyer's patches as early as one day after oral inoculation (FIG. 5F).

Dramatic morphological changes in the underlying lymphoid tissue were also clearly apparent when viewed by TEM. Five days after infection with χ4973, lymphoid cells within the Peyer's patch follicle appeared healthy and similar in morphology to Peyer's patches from uninfected mice (FIGS. 5A and 5B). In contrast, extensive changes in gross morphology were observed in Peyer's patch lymphoid cells five days after infection with χ3339 (FIG. 5C).

These data show that rpoS mutant S. typhimurium do not efficiently invade and colonize the GALT. As a result, the rpoS mutants would be expected to be defective in stimulating a generalized mucosal immune response, which is dependent upon colonization of the GALT. Furthermore, because the GALT is the portal of entry into mesenteric lymph nodes and the spleen, the mutants would also be expected to be ineffective in invading and colonizing these deeper lymphoid tissues. This would be expected to result in the mutants being defective in stimulating systemic humoral immunity as well as cellular immune responses, which are dependent upon colonization of the mesenteric lymph nodes and spleen. In contrast, strains containing the wild-type rpoS allele more efficiently invade and colonize the GALT and deeper lymphoid tissues and are, as a result, more effective in eliciting mucosal, humoral and cellular immune responses.

On the other hand, the rpoS⁺ strains destroyed the Peyer's patch tissue, making such strains less than ideal candidates for use in vaccines. Therefore, it is desirable to modify the rpoS⁺ microbes with at least one virulence reducing mutation so that the microbes are still able to invade and colonize the Peyer's patches, but without destroying the Peyer's patch tissue.

EXAMPLE 2

This example illustrates methods which can be used in constructing defined deletion mutations in genes to confer an attuation upon rpoS⁺ S. typhimurium and S. typhi strains as well as other bacteria suitable for use as vaccines for humans.

The generation of chromosomal deletions using transposon Tn10 has been previously described in a wide variety of bacteria, including Salmonella (Kleckner et al., J. Mol. Biol. 116:125–159, 1977; EPO Pub. No. 315,682; U.S. Pat. No. 5,387,744; which are incorporated by reference). Recently, new methods have become available for introducing specific mutations into genes. The gene to be mutated can be selected from a population of clones contained in a genomic DNA library constructed in a cloning vector, or by cloning the amplified product containing all or a portion of the gene into a plasmid using PCR methodology. Mutations introduced into such genes or portions of genes are known as defined deletions and these are constructed using one of two general methods.

One method employs restriction enzymes to remove all or a portion of an isolated gene from a recombinant vector. This method allows the mutation of genes for which DNA sequence information is unavailable. However, this method is limited to the use of restriction sites present within the gene or within the DNA flanking the cloned gene.

Another method employs the use of divergent PCR primers synthesized based upon known DNA sequence either within the gene to be deleted or within DNA flanking the gene. The primers are mixed with a vector containing a cloned gene and subjected to an inverse PCR reaction, resulting in the amplification of the entire plasmid but deleting all or a portion of the target gene (Innis et al., infra). The PCR reaction amplifies upstream and downstream regions flanking a specified segment of DNA to be deleted from the cloned gene and generates a product consisting of the cloning vector and upstream and downstream flanking sequences. The inverse PCR method is preferred because it allows the placement of mutations of any size at any position within a gene of known DNA sequence, and allows the introduction of novel restriction sites to be engineered into the PCR primers or target DNA which then can be used for the subsequent insertion of other cloned sequences. An alternative PCR method for generating defined deletions relies on amplified PCR products which represent portions of the gene or flanking DNA sequence. These are ligated together in a cloning vector to construct the defined deletion mutation.

A genomic library can be constructed in any number of cloning vectors (Sambrook et al., supra). Clones containing a gene in which a deletion is to be generated can be isolated from the genomic library by complementation in a bacterial strain which contains a mutation in the same gene.

For example, genomic DNA libraries from wild-type *Salmonella typhimurium* UK-1 (χ3761) can be constructed in a suitable cloning vector such as pNEB-193 (New England Biolabs), which is a pUC19 derivative that carries single sites for the unique 8-base cutters: AscI, PacI and PmeI. Generally, genomic DNA is isolated according to standard methods (Sambrook et al., Molecular Cloning/A Laboratory Manual Second Edition, Cold Spring Harbor Press, Cold Spring Harbor, N.Y., 1989). Sau3A1 partially digested genomic DNA is sized on an agarose gel and extracted using commercially available methods in kit form obtained from Promega, Quiagen, or Bio101. DNA fragments between 2 and 6 kb are isolated and ligated into a plasmid first digested with BamHI or BglII, then dephosphorylated using alkaline phosphatase according to the manufacturers' instructions. The resulting plasmid library is then introduced into an appropriate *E. coli* strain in order to amplify the genomic library and to obtain a population of recombinant plasmids containing random genomic DNA inserts ranging in size from 2 to 6 kb. Relevant clones are isolated from a genomic library by complementation of mutant *E. coli* or *S. typhimurium* strains.

Where the DNA sequence of a gene is already known, PCR primers are synthesized and the gene and often some flanking sequence is amplified using PCR methodology directly from a sample of bacteria or from purified genomic DNA, and the product, cloned into a plasmid vector such as pNEB-193. Thus, where the gene sequence is known, screening a genomic library is not required.

Virtually any cloning vector can be used in constructing the strains of the present invention, so long as the defined deletion is located on the vector and is linked to a selectable marker. There are a number of different methods available for introducing the defined deletion mutations into the chromosome, including temperature-sensitive replicons (Hamilton et al., *J. Bacteriol.* 171:4617–4622, 1989), linear transformation of recBC mutants (Jasin et al., *J. Bacteriol.* 159:783–786, 1984), and host restricted replicons known also as suicide vectors (Miller et al., *J. Bacteriol.* 170: 2575–2583, 1988). All of these methods can result in an allele replacement, whereby a mutant allele constructed on a vector replaces a wild-type allele on the chromosome, or vice versa.

The pir-dependent R6K replicon has been used by numerous investigators and is one of the most reliable suicide vectors available for allele replacement. Replication of the R6K plasmid requires the pir gene product. A pir-dependent plasmid will not replicate in a pir$^-$ host bacterium, and so the presence of a defined deletion mutation on a pir-dependent plasmid will allow for the selection of rare events in which the plasmid has integrated into the host chromosome within a homologous region flanking the deletion constructed on the plasmid. This event will confer some selectable phenotype upon the strain into which the plasmid has integrated, because even though the plasmid cannot replicate, the integration event provides a mechanism of stable maintenance of the elements on the plasmid. Antibiotic-resistance elements are generally used to select for the presence of the integrated plasmid, and can be selected from genes which encode resistance to ampicillin, kanamycin, chloramphenicol, gentamicin, spectinomycin and tetracycline, and others well known in the art. The host strain which contains a defined deletion along with an integrated suicide vector is characterized as a merodiploid, since it contains two different alleles of the same gene. Generally, the deletion constructed on the vector will represent a gene deletion and the integrated product on the chromosome will have the structure characterized by the presence of a wild-type allele flanking one end of the integrated vector, and the defined deletion mutant allele at the other end of the vector. Other constructions are well known in the art.

Bacteria in which the suicide vector has been excised from the chromosome along with the antibiotic-resistance marker can be selected on specialized media. Two such counter selection methods have been employed to identify these antibiotic-sensitive strains. One method, which is described in Example 1, relies on fusaric acid sensitivity of tetracycline resistant strains. Colonies which appear on fusaric acid plates are screened for the loss of tetracycline resistance and the presence of the mutant allele. Another counter selection method takes advantage of sucrose sensitivity using the sacRB system (Kaniga et al., *Gene* 109: 137–141, 1991) in which expression of levanosucrase in the presence of 5% sucrose is toxic to cells retaining the sacb gene.

Following the introduction of any defined deletion mutant allele into a strain, phenotypes associated with the mutant gene are characterized using standardized tests well known in the art. These tests include determination of phenotypic reversion frequency, confirmation of deletion by Southern blot or PCR, agglutination by O-group specific antisera, production of complete LPS, presence of flagellar H antigen, motility, plasmid content and confirmation of auxotrophies.

Mutant strains may be shown by Southern blot to possess a loss of genetic material corresponding to the region deleted, as revealed by a mobility shift of DNA relative to the wild-type and the defined deletion mutant allele constructed on a plasmid. PCR analysis of mutant strains significantly reduces the time required for confirming the presence of defined deletions since no DNA isolation is required and results can be completed in less than one day. The PCR method also allows the identification of erroneous recombination events or retention of delivery vector sequences, revealed as mobility shifts or the production of multiple DNA fragments other than those expected upon gel analysis of PCR products.

After construction, strains with defined deletion mutations are fully evaluated for properties associated with the mutation and/or which are important for a strain to be immunogenic as well as attenuated. For example, production of full-length LPS similar to the parental wild-type strain is evaluated using silver stained gels. The confirmation of correct O-antigen is determined by antisera agglutination of mutant cells. Mutant strains are evaluated for positive agglutination using diluted poly H antiserum (Difco) and subjected to motility tests in soft agar motility tubes relative to the parent strains and non-flagellated control strains, $\chi$3420 and $\chi$3422. Standard clinical API test strips are used following isolation of each mutant strain to obtain fermentation and biochemical data for comparison to parental strains. Growth rates and plasmid content of the mutant strains are also compared to that of parental strains. With *S. typhi* strains, the plasmid content is not evaluated because the large virulence plasmid present in *S. typhimurium* is absent in *S. typhi* (Gulig et al., Infect. Immun. 56:3262–3271, 1987).

Construction of Defined Deletions in phoP, phoQ, and phoPQ Genes

The *Salmonella* phoPQ operon consists of phoP and the adjacent downstream phoQ genes. Defined deletions in the phoP and phoQ genes can be constructed using an inverse PCR strategy since the entire nucleotide sequence of the operon and some flanking sequence is known. The DNA sequence reveals the presence and position of restriction sites which can be useful in constructing defined deletions in these genes. The genes can be isolated on a single 2,110 base pair PCR product and cloned into a plasmid vector. The recombinant vector containing the phoPQ gene cassette can be digested with restriction enzymes to delete most of the phoP gene, leaving the phoQ gene intact. The defined phoP deletion on the phoPQ gene cassette can be inserted into a suicide vector, and introduced into the chromosome of a wild-type phoPQ *Salmonella* to produce an antibiotic-resistant merodiploid, which can be grown on appropriate media to select for the loss of the integrated plasmid along with the antibiotic-resistance marker. Antibiotic-sensitive strains can be phenotypically characterized for the presence of an appropriate defined deletion phoP mutant allele by screening for the loss of acid phosphatase activity using the agar overlay method of Kier et al. (*J. Bacteriol.* 130:399–410, 1997). A mutation in either phoP or phoQ is sufficient to confer a PhoP⁻ phenotype.

Defined deletion mutants in phoQ or in both phoP and phoQ can be generated using a similar strategy, using restriction enzymes to delete defined segments of DNA from either phoQ or from both phoP and phoQ, and introduced into the chromosome on a suicide vector to generate merodiploids, which can be counter selected on appropriate media for the loss of the integrated plasmid and antibiotic-resistance marker, and phenotypically screened for the presence of the relevant defined deletion mutant allele using PCR to verify the genotype.

Construction of Defined Deletions in the cya Gene

A recombinant vector which confers a maltose positive phenotype to an *E. coli* cya mutant strain when grown on MacConkey maltose media can be used to construct a defined deletion in a *Salmonella* cya gene. Divergent primers based on the known *Salmonella* cya gene sequence can be used in an inverse PCR reaction with the complementing recombinant vector as a template to generate a linear product consisting of the vector and DNA flanking either end of the deleted DNA specified by the PCR primer positions. Alternatively restriction enzymes can be used to delete all or a portion of the complementing cya gene from the recombinant vector.

A defined deletion constructed using either method can be excised from the cloning vector using restriction enzymes and introduced into a suicide vector containing an antibiotic-resistance marker. The resulting recombinant suicide vector containing the defined deletion cya allele can be introduced into the chromosome of a wild-type cya *Salmonella* strain to generate an antibiotic-resistant merodiploid. The merodiploid would be grown on appropriate media to select for the loss of the integrated plasmid along with the antibiotic-resistance marker. Antibiotic-sensitive strains would be phenotypically characterized for the presence of an appropriate defined deletion Δcya-27 mutant allele. MGM-232 and $\chi$8217 are two *S. typhimurium* UK-1 strains with defined Δcya-27 mutations that were constructed by these methods (see Table 1).

Construction of Defined Deletions in the crp Gene

Defined deletions in the *Salmonella* crp gene can be constructed using a strategy similar to that used for construction of a defined deletion in cya. A recombinant vector can be selected which confers a maltose positive phenotype to an *E. coli* crp mutant strain when grown on MacConkey maltose media. Divergent PCR primers can be used to delete the known *Salmonella* crp gene and flanking sequences, and the resulting defined deletion introduced into the chromosome of a wild-type crp *Salmonella* on a suicide vector to generate an antibiotic-resistant merodiploid. The merodiploid could be grown on appropriate media to select for the loss of the antibiotic resistance and the integrated plasmid, and antibiotic-sensitive strains could be phenotypically characterized for the presence of an appropriate defined deletion crp mutant allele.

Construction of Δcya Δcrp Double Mutants

Strains which contain defined deletion mutations in both cya and crp can also be constructed. For example, cya mutants can be constructed as described above, and then a defined deletion mutant crp allele can be introduced on a suicide vector to generate merodiploids selected on an appropriate antibiotic medium. Growth of merodiploids on an appropriate medium such as fusaric acid or 5% sucrose as described above can be used to counter select for the loss of the suicide vector along with the antibiotic-resistance gene from the chromosome, and an appropriate defined deletion crp mutant can be phenotypically identified on MacConkey maltose medium containing 2 mM cAMP. This is because cAMP which is the product of adenylate cyclase encoded by the cya gene causes a cya mutant to be phenotypically Cya⁺ on MacConkey maltose agar. However, a crp mutation renders the cya mutant strain no longer capable of fermenting maltose and thus selection on maltose medium allows easy detection of strains with both of the defined Δcya and Δcrp mutations. MGN-431 and $\chi$8214 are two strains with defined cya and crp deletion mutations constructed in this way (see Table 1).

Construction of Defined Deletions in pmi and cdt Genes

Mutations in other genes have also been shown to confer an attenuation on *Salmonella*, including cdt and pmi alleles. Defined deletions in the pmi gene can be constructed using an inverse PCR strategy, or restriction enzymes. A recombinant vector which confers a mannose-positive phenotype to an *E. coli* or *Salmonella* mutant pmi strain when grown on MacConkey mannose media can be used to construct a defined deletion mutant pmi allele using either restriction enzymes or inverse PCR. The defined deletion pmi allele can be inserted into a suicide vector and integrated into the chromosome of a $pmi^+$ *Salmonella* to generate an antibiotic-resistant merodiploid, which can be grown on appropriate media to select for the loss of the integrated plasmid along with the antibiotic-resistance gene. Antibiotic-sensitive strains would be phenotypically characterized for the presence of an appropriate defined deletion pmi mutant allele by screening for a reversible rough-smooth phenotype, detecting a smooth phenotype due to the synthesis of LPS O-antigen repeats when grown in the presence of mannose, and a rough phenotype when grown in the absence of mannose detected by the absence of agglutination in the presence of LPS O-antisera.

A defined deletion which confers a $Cdt^-$ phenotype upon *Salmonella* can be constructed using restriction enzymes to delete DNA associated with this phenotype from a recombinant vector which complements a *Salmonella* cdt mutant. The mutant allele constructed using this strategy can be inserted into a suicide vector and introduced into the chromosome of a $cdt^+$ *Salmonella* to generate antibiotic-resistant merodiploids. Merodiploids can be grown on appropriate media to select for the loss of the integrated vector along with the antibiotic-resistance marker, and antibiotic-sensitive strains can be phenotypically characterized for the presence of an appropriate defined deletion cdt mutant allele.

EXAMPLE 3

This example illustrates the construction of defined ΔphoPQ23 and ΔasdA16 deletions in *S. typhi* ISP1820 and Ty2 to produce strains MGN-1191 and MGN-1256, respectively.

The construction of the defined ΔphoPQ23 ΔasdA16 *S. typhi* strains in both the ISP1820 and Ty2 backgrounds involved the use of two suicide plasmids, pMEG-213 containing the ΔphoPQ23 region and pMEG-006 containing the ΔasdA16 region.

The ΔphoPQ23 deletion was obtained by digesting pMEG-068 with EcoRV and TthIIII1 removing the 1103 bp EcoRV-TthIII1 fragment encoding the C terminal end of PhoP and the His region of PhoQ, responsible for phosphorylation of PhoP (FIG. 6). The linearized plasmid was then treated with T4 DNA polymerase and religated to produce pMEG-210 (FIG. 6). The BamHI-XbaI fragment of pMEG-210 containing the ΔphoPQ23 deletion was then inserted in the pir-dependent suicide vector pMEG-149 to produce pMEG-213 (FIG. 6). Since pMEG-213 is a mobilizable suicide vector encoding for the selectable marker for ampicillin resistance and the counter-selectable marker, levanosucrase, resulting in sensitivity to sucrose, the plasmid can be conjugated into any strain desired selecting for ampicillin resistance followed by counter-selection for the replacement of the wild-type phoPQ genes with the mutant phoPQ23 in the presence of sucrose. The host strain responsible for the delivery of pMEG-213 was obtained by transforming pMEG-213 into the $Pir^+$ $Asd^-$ delivery host MGN-617 to produce MGN-758.

Introduction of the ΔphoPQ23 deletion into *S. typhi* ISP1820, χ3744, and *S. typhi* Ty2, χ3769, was accomplished by conjugating MGN-758 with the wild-type *S. typhi* parents and selecting for ampicillin-resistant isolates which grew without DAP (diaminopimelic acid). The isolates obtained from this conjugation represent the first integration of the ΔphoPQ23 deletion into the chromosome producing a duplication of the wild-type gene with the mutant ΔphoPQ23. These isolates, MGN-1037 and MGN-1017, were then plated on Luria agar with 5% sucrose to select for loss of the ampicillin-resistant suicide vector. The isolates obtained by this selection were then screened for acid phosphatase activity using the agar overlay method of Kier et al. (*J. Bacteriol.* 130:399–410, 1977). The white phosphatase-negative colonies were then confirmed for the ΔphoPQ23 phosphatase minus phenotype and stocked as MGN-1038 for *S. typhi* ISP1820 and MGN-1018 for *S. typhi* Ty2.

The introduction of a defined asd deletion was then needed to provide a vaccine strain for the delivery of heterologous antigens. The defined asd deletion present on pMEG-006 was obtained by performing inverse PCR on pMEG-003 to remove the majority of the coding region of the asd gene between 219 and 1460 bp to produce pMEG-006 containing a new unique BglII site (FIG. 7). pMEG-006 has a pir-dependent replicon and the tetracycline-resistance gene from the transposon Tn10, but has no mobilization functions to allow conjugation.

Introduction of the defined ΔasdA16 deletion into any strain requires plasmid DNA to be electroporated into the strain desired followed by selection for tetracycline resistance. The tetracycline-resistant isolates obtained can then be plated on fusaric acid containing media to select for loss of the tetracycline-resistant elements of the suicide vector (Maloy et al., *J. Bacteriol.* 145:1110–1112, 1981) followed by screening for the $Asd^-$ DAP-requiring phenotype. Both MGN-1038 and MGN-1018 were electroporated with pMEG-006 and tetracycline-resistant isolates obtained. These isolates were then plated on fusaric acid plates containing 50 ug DAP/ml and the isolated colonies obtained screened for the loss of the tetracycline-resistance element of the suicide vector and replacement of the wild-type asd gene with the ΔasdA16 mutation. Isolates were then confirmed for tetracycline sensitivity and requirement of DAP. An *S. typhi* ΔphoPQ23 ΔasdA16 derivative of each strain was selected for further work, which are designated herein as MGN-1191 (ISP1820) and MGN-1256 (Ty2) (See Table 1).

EXAMPLE 4

This example illustrates methods for testing *Salmonella* and other Enterobacteriaceae strains for an $RpoS^+$ phenotype.

Testing for catalase activity provides one method for determining the rpoS allelic state of strains since RpoS positively regulates expression of hydroperoxidase II catalase from the katE gene in *S. typhimurium.* (Lowen, supra). Cultures can be analyzed for catalase production as an indicator of the RpoS phenotype, by adding 100 μl of hydrogen peroxide ($H_2O_2$) to one milliliter of each strain grown to stationary phase (Mulvey et al., *Gene* 73:337–345, 1988). Vigorous bubbling of a stationary phase culture after addition of $H_2O_2$ would suggest that the strain contained a wild-type rpoS allele, whereas minimal bubbling would imply that the strain contained a defective rpoS allele.

The RpoS phenotype of attenuated *Salmonella* strains can also be determined by assessing the sensitivity of the strains to nutrient deprivation and acid and oxidative stress. *Salmonella* rpoS mutants are known to have a reduced ability to survive these stresses as compared to wild-type parents (Fang et al., *Proc. Natl. Acad. Sci.* 89:11978–11982, 1992). Evaluation of prolonged stationary-phase survival can be performed in M9 medium on a rotary shaker at 37° C. for 6 days. Susceptibility to pH 4.0 can be determined by pelleting stationary-phase bacteria and resuspending cells in L-broth adjusted to pH 4.0 with citrate buffer. Sensitivity of strains to oxidative stress can be determined by the addition of hydrogen peroxide to stationary-phase bacteria in L-broth to a final concentration of 15 mM. In each of these experiments, bacteria are removed at timed intervals, eluted and plated onto L-agar for quantitation of viable cells.

The response of an *S. typhimurium* rpoS mutant strain to each of the above mentioned stresses has been reported and compared to its virulent parent strain (Fang et al., supra). Specifically, the rpoS *S. typhimurium* mutant exhibited a 7-fold reduced ability to survive a prolonged stationary phase relative to its wild-type parent in M-9 media on a rotary shaker at 37° C. for 6 days. Likewise, the rpoS *S. typhimurium* mutant was 10-fold more susceptible to killing by pH 4.0 as compared to its wild-type parent after stationary-phase cultures of these strains were resuspended in L-broth adjusted to pH 4.0 with citrate buffer. In addition, 98% of an inoculum of the rpoS *S. typhimurium* mutant did not survive a 60 minute exposure to 15 mM $H_2O_2$, whereas the wild-type parent was unaffected by this treatment.

Another approach that can be used to determine the RpoS phenotype involves assessing the ability of the *Salmonella* to synthesize glycogen. It has been shown that rpoS null mutations result in a glycogen-negative phenotype (Lang et al., *Mol Microbiol.* 5:49–59, 1991). Specifically, the glgS gene is an rpoS-dependent gene which is involved in glycogen synthesis. Furthermore, since a null glgS mutant accumulates more glycogen than a rpoS mutant, rpoS may have further effects on glycogen synthesis in addition to glgS induction. Thus, it is possible to determine the rpoS allelic state of strains by analyzing their ability to accumulate glycogen.

Accumulation of glycogen is tested by growing cells as single colonies or patches on Q-3 medium which contains 0.06M $K_2HLPO_4$, 0.03M $KH_2PO_4$, 0.008M $(NH_4)_2SO_4$, 0.0017M sodium citrate, $8.1 \times 10^{-4}$M $MgSO_4$, $1.9 \times 10^{-4}$ histidine HCl, $1.5 \times 10^{-5}$M thiamine HCl, and 0.056M glucose. When analyzing the glycogen biosynthesis abilities of auxotrophic strains, the appropriate nutrient supplements are added to Q-3 media. For example, methionine (20 μg/ml), threonine (80 μg/ml), leucine (20 μg/ml), and DAP (100 μg/ml) must be added to Q-3 media to sustain the growth of Δasd mutant strains. Furthermore, since *S. typhi* Ty2 and ISP1820 are cys and cys trp mutants, respectively, Q-3 media must be supplemented with each of these amino acids at a concentration of 20 μg/ml. After about 20 hours of growth at 37° C., the cells are treated with a solution of iodine and potassium iodide. Strains which are wild-type and functional with respect to glycogen biosynthesis turn brown after iodine treatment, while those strains which are defective in glycogen biosynthesis stain yellow.

In a variation of the above approaches, the RpoS phenotype can be determined by first moving the rpoS allele into either a wild-type *S. typhimurium* such as χ3339 if the allele to be tested is expected to have a rpoS mutation or into the rpos mutant χ4973 if the allele is expected to be rpoS+ using P22HTint-mediated transduction followed by subsequent testing of the derived microbe for RpoS phenotype by any of the tests as described above. Final proof of the allelic state of an rpoS allele can be achieved by DNA sequencing using PCR methods.

EXAMPLE 5

This example illustrates the superior ability of attenuated *S. typhimurium* rpoS+ strains having attenuating mutations in the cya, aroA, or in both the cya and crp genes in colonizing Peyer's patches of the GALT, compared to the colonizing ability of corresponding rpoS mutant *S. typhimurium* strains.

The attenuated rpoS+ *S. typhimurium* strains tested were MGN-431, a Δcya/Δcrp mutant; χ3679, an ΔaroA mutant; and MGN-232, a Δcya mutant (see Table 1 for derivations). Comparative *S. typhimurium* strains containing an inactive rpoS allele were constructed as described below to obtain χ8214, χ8215 and χ8217.

Cultures were maintained as frozen cultures suspended in 1% Bacto-peptone containing 5% glycerol and fast-frozen in dry-ice ethanol for storage in duplicate at −70° C. and also suspended in 1% Bacto-peptone containing 50% glycerol for storage at −20° C. for routine use.

Complex medium for routine cultivation of *S. typhimurium* strains was L broth as described above. Difco agar was added to Lennox broth at 1.5% for base agar and 0.65% for soft agar. L agar was used for routine enumeration of bacteria. Fermentation was evaluated by supplementing MacConkey base agar (Difco, Detroit, Mich.) with 1% final concentration of lactose.

In generating comparative rpoS mutant cultures, media were supplemented with ampicillin (50 μg/ml) to select for ampicillin-resistant *S. typhimurium* strains containing the inactive rpoS allele. Buffered saline with gelatin (BSG) (Curtiss, 1965 supra) was used routinely as a diluent.

Bacteriophage P22HTint propagated on SF1005 was used to transduce the rpoS mutant allele into MGN-431, χ3679, and MGN-232 to generate χ8214, χ8215, and χ8217, respectively (see Davis et al., supra). An overnight culture of the donor strain was diluted 1:20 into prewarmed L broth, grown for 60 minutes with shaking at 37° C. and then infected with P22HTint at a multiplicity of 0.01. The infection mixture was shaken overnight for approximately 15 h, chloroform added and allowed to shake an additional 10 minutes at 37° C., and the suspension centrifuged (Sorvall RC5C, SS-34 rotor, 7,000 rpm, 10 min) to remove bacterial debris. The supernatant fluid containing the phage (ca. $10^{10}$/ml) was stored at 4° C. over chloroform. Ampicillin to a concentration of 50 μg/ml was used to select for transductants containing an inactive rpoS allele.

The RpoS phenotype of the *S. typhimurium* strains was determined by testing for catalase and glycogen synthesis activities as described in Example 4. Results are shown in Table 8.

TABLE 8

Catalase and Glycogen Activity Tests on *S. typhimurium* Strains.

| Strain | Relevant Genotype | Catalase Activity | Glycogen Synthesis Activity |
|---|---|---|---|
| χ3339 | SL1344 pStSL100+ hisG rpsL, colicin+ | + | + |
| χ4973 | SL1344 pStSR100+ hisG rpsL, rpoS: :RR10, colicin+ | − | − |

TABLE 8-continued

Catalase and Glycogen Activity Tests on *S. typhimurium* Strains.

| Strain | Relevant Genotype | Catalase Activity | Glycogen Synthesis Activity |
|---|---|---|---|
| χ3761 | UK-1 wild-type prototroph | + | + |
| χ4937 | UK-1 rpoS: :RR10 | – | – |
| MGN-232 | UK-1 Δcya-27 | + | + |
| χ8217 | UK-1 rpoS: :RR10 Δcya-27 | – | – |
| MGN-431 | UK-1 Δcya-27 Δcrp-27 | + | – |
| χ8214 | UK-1 rpoS: :RR10 Δcya-27 Δcrp-27 | – | – |

Those *Salmonella* known to have a wild-type rpoS gene showed catalase activity, whereas, those strains having a mutation in the rpoS gene showed no catalase activity. Results with glycogen activity testing agreed with catalase testing with the exception that MGN-431, which has an rpoS gene and was catalase positive, nevertheless, gave negative results in the glycogen test. This is undoubtedly due to the fact that glycogen synthesis is also dependant on crp gene function.

Female BALB/c mice (6 to 10 weeks old) (Charles River Laboratories, Wilmington, Mass.) were used for infectivity and/or immunization experiments. Animals were held for one week in a quarantined room prior to being used in experiments. Experimental mice were placed in Nalgene filter-bonnet-covered cages with wire floors. Food and water were withheld for 4–6 hours prior to peroral infection.

The animal infectivity of *S. typhimurium* strains was determined following peroral (p.o.) inoculation. Bacteria for inoculation in mice were grown overnight as standing cultures at 37° C. in L broth. These cultures were diluted 1:200 into prewarmed broth and aerated at 37° C. for approximately 4 h to an $OD_{600}$ of 0.8. The cells were concentrated 50-fold by centrifugation in a GSA rotor at 7,000 rpm for 10 min at 4° C. in a Sorvall RC5C centrifuge followed by suspension in BSG. Suitable dilutions were plated on L agar for titer determination. For all p.o. inoculations with *S. typhimurium*, mice were deprived of food and water for 4–6 h prior to inoculation. They were then fed 20 μl of *S. typhimurium* suspended in BSG using a Pipetman P20. Food and water were returned 30 minutes after oral inoculation.

In order to assess the colonization of the GALT and, in particular, Peyer's patches, by rpoS$^+$ attenuated *S. typhimurium* strains, three groups of three mice each were inoculated perorally with equal numbers (approximately $10^9$ CFU) of an rpoS$^+$ attenuated *S. typhimurium* strain and its corresponding rpoS::RR10 mutant derivative, which were grown according to the conditions described above. Quantitation of viable *S. typhimurium* in Peyer's patches was performed as follows. The mice were euthanized at 3, 5, and 7 days after p.o. infection and their Peyer's patches collected. The Peyer's patches from each mouse were aseptically removed and placed in polypropylene tubes with BSG, homogenized with a Brinkmann tissue homogenizer (Brinkmann Instruments) and placed on ice. Appropriate dilutions of the homogenate were plated on MacConkey agar supplemented with lactose at 1% with and without ampicillin. Differentiation of the strains was facilitated by the presence of an ampicillin-resistance marker within the inactive rpoS::RR10 allele. Plates were incubated for 12–15 hours at 37° C. Titers in the respective Peyer's patches were determined for each time period and the geometric means calculated for 3 mice per group at each time of sampling.

Table 9 below shows the distributions of rpoS$^+$ and rpoS::RR10 mutant *S. typhimurium* strains containing Δcya/Δcrp, ΔaroA, or Δcya mutations in murine Peyer's patches after peroral infection.

TABLE 9

Geometric mean ratios of attenuated rpoS$^+$ *S. typhimurium* Δcya/Δcrp, ΔaroA, or Δcya strains to their corresponding isogenic rpoS: :RR10 mutant Δcya/Δcrp, ΔaroA or Δcya derivatives in murine Peyer's patches after peroral coinfection[a]

| Time afer infection | rpoS$^+$ Δcya/Δcrp rpoS: :RR10 Δcya/Δcrp | rpoS$^+$ ΔaroA rpoS: :RR10 ΔaroA | rpoS$^+$ Δcya rpoS: :RR10 Δcya |
|---|---|---|---|
| 3 days | 2.1 ± 0.7 | 1.2 ± 0.2 | 6.5 ± 2.6 |
| 5 days | 1,468 ± 1,271 | 4.3 ± 3.0 | 1.7 ± 0.8 |
| 7 days | 308 ± 196 | 4,135 ± 4,132 | 7.1 ± 4.2 |

[a] Approximately equal numbers of MGN-431 (rpoS$^+$ Δcya/Δcrp) and χ8214 (rpoS: :RR10 Δcya/Δcrp) (5.2 × $10^8$ and 5.4 × $10^8$, respectively); χ3679 (rpoS$^+$ ΔaroA) and χ8215 (rpoS: :RR10 ΔaroA) (6.0 × $10^8$ and 6.0 × $10^8$, respectively); or MGN-232s (rpoS$^+$ Δcya) and χ8217 (rpoS: :RR10 Δcya) (6.8 × $10^8$ and 6.4 × $10^8$, respectively), were administered p.o. to 8-week-old BALB/c mice. Geometric mean ratios ± S.E.M. are given (n = 3).

The rpoS$^+$ *S. typhimurium* strain containing Δcya/Δcrp mutations, MGN-431, exhibited a significantly greater ability to colonize Peyer's patches at 5 days after oral infection compared to its rpoS::RR10 derivative strain, χ8214. At 3 and 5 days after oral infection, the rpoS$^+$ ΔaroA *S. typhimurium* strain χ3679 and its rpoS::RR10 derivative, χ8215, did not exhibit any significant differences in ability to colonize the Peyer's patches. However, by 7 days postinfection, the rpoS::RR10 ΔaroA mutant displayed a significantly lower ability to colonize Peyer's patches as compared to its ΔaroA parent strain, χ3679.

Coynault et al. have also reported that rpoS ΔaroA derivatives are defective in colonizing murine Peyer's patches compared to rpoS$^+$ parent strains, however, the decrease in colonization was observed at the earlier times of 2 and 5 days after oral infection compared to the decrease in colonization at 7 days reported here. (Coynault et al., *Mol. Microbiol.* 22:149–160, 1996).

Similar studies were done with Δcya mutants. As shown in Table 9, when administered orally to mice in approximately a 1:1 ratio, the rpoS::RR10 Δcya mutant strain χ8217 exhibited a reduced ability to colonize Peyer's patches at 3 and 7 days (ca. 6 and 7 fold, respectively) as compared to its parent strain, MGN-232.

EXAMPLE 6

This example illustrates the superior balance of high immunogenicity and low virulence of the rpoS$^+$ *S. typhimurium* strains of Example 5 having either aroA or cya mutations, compared to that of the corresponding isogenic rpoS$^-$ mutant *S. typhimurium* strains.

Protective immunity elicited by attenuated *S. typhimurium* strains having an rpoS$^+$ genotype compared to the corresponding rpoS mutant strains was determined in BALB/c mice following peroral inoculation as follows. Five mice per group were p.o. inoculated with $10^6$, $10^7$, $10^8$ and $10^9$ CFU of the attenuated *S. typhimurium* rpoS$^+$ strain or its isogenic rpoS mutant derivative, respectively. Four weeks after immunization, mice were challenged p.o. with $10^9$ CFU of the wild-type SR-11 or UK-1 virulent parent strain. The degree of protection is determined by the number of mice alive 30 days after challenge and the data are shown in Tables 10 and 11 below.

TABLE 10

Protection in mice against challenge with the virulent wild-type SR-11 strain (χ3181) after immunization with (A) χ3679 (rpoS$^+$ ΔaroA) or (B) its isogenic rpoS mutant derivative, χ8215

| Immunization Dose[a] | Challenge Dose of SR-11[a] | Live/Total (%) |
|---|---|---|
| A. χ3679 | | |
| $1.6 \times 10^6$ | $1 \times 10^9$ | 2/5 (40%) |
| $1.6 \times 10^7$ | $1 \times 10^9$ | 2/5 (40%) |
| $1.6 \times 10^8$ | $1 \times 10^9$ | 4/5 (80%) |
| $1.6 \times 10^9$ | $1 \times 10^9$ | 4/5 (80%) |
| B. χ8215 | | |
| $1.4 \times 10^6$ | $1 \times 10^9$ | 0/5 (0%) |
| $1.4 \times 10^7$ | $1 \times 10^9$ | 1/5 (20%) |
| $1.4 \times 10^8$ | $1 \times 10^9$ | 3/5 (60%) |
| $1.4 \times 10^9$ | $1 \times 10^9$ | 3/5 (60%) |

[a]Data represented as colony forming units per ml.

TABLE 11

Protection in mice against challenge with the virulent wild-type UK-1 strain (χ3761) after immunization with (A) MGN-232 (rpoS$^+$ Δcya) or (B) its isogenic rpoS derivative, χ8217

| Immunization Dose[a] | Challenge Dose UK-1[a] | Live/Total (%) |
|---|---|---|
| A. MGN-232 | | |
| $2.0 \times 10^6$ | $8 \times 10^8$ | 4/5 (80%) |
| $2.0 \times 10^7$ | $8 \times 10^8$ | 5/5 (100%) |
| $2.0 \times 10^8$ | $8 \times 10^8$ | 5/5 (100%) |
| $2.0 \times 10^9$ | $8 \times 10^8$ | 5/5 (100%) |
| B. χ8217 | | |
| $1.2 \times 10^6$ | $8 \times 10^8$ | 2/5 (40%) |
| $1.2 \times 10^7$ | $8 \times 10^8$ | 1/5 (20%) |
| $1.2 \times 10^8$ | $8 \times 10^8$ | 2/5 (40%) |
| $1.2 \times 10^9$ | $8 \times 10^8$ | 2/5 (40%) |

[a]Data represented as colony forming units per ml.

The data presented in Table 10 indicate that, regardless of the dose used for vaccination, mice orally immunized with the rpos$^+$ ΔaroA mutant, χ3679 were better protected against oral wild-type challenge than were mice immunized with the isogenic rpoS mutant strain, χ8215. Similarly, Table 11 shows that immunization with rpoS$^+$ microbes attenuated with a Δcya mutation provided better protection against the wild-type challenge than immunization with the isogenic rpoS mutant derivative.

Thus, this study shows that a *S. typhimurium* strain having a functional rpoS gene provides protective immunity that is significantly better than that of the isogenic rpoS mutant strain when challenged orally with the wild-type virulent *Salmonella* strain. Thus, the presence of a functional rpoS allele in *S. typhimurium* increases the immunogenicity of the strain to facilitate the stimulation of a high level of protective immunity.

EXAMPLE 7

This example illustrates the superior immunogenicity of an attenuated RpoS$^+$ strain of *S. typhimurium* following intranasal administration compared to the immunogenicity of the corresponding RpoS$^-$ strain administered by the same route.

Bacteria for intranasal immunization in mice were grown overnight as standing cultures at 37° C. in L broth. The following morning, these cultures were diluted 1:200 into L broth and aerated at 37° C. until reaching an OD$_{600}$ of 0.8. The cells were concentrated by centrifugation in a Sorvall GSA rotor at 7,000 rpm for 10 min at 4° C. followed by suspension in BSG. Suitable dilutions were plated on L agar for titer determinations.

For each attenuated bacterial vaccine strain, intranasal immunizations were performed with eight-week-old female BALB/c mice such that each mouse received either $10^9$ or $10^8$ cfu in a total volume of 0.01 ml (10 μl) of BSG using a micropipette to administer droplets into one or both nostrils. Immunization was accomplished by inoculating each nostril with 0.005 ml (5 μl) of suspension or one nostril with 0.01 ml (10 μl) of suspension, or in the case of the controls with BSG lacking any bacteria. Food and water were returned within 30 min following intranasal immunization.

Intranasally immunized mice and non-immunized controls were orally challenged with either $10^8$ or $10^9$ cfu of the wild-type virulent *S. typhimurium* strain, χ3339, 30 days after the date of intranasal immunization. The χ3339 challenge strain was grown overnight as a standing culture at 37° C. in L broth. The following morning the culture was diluted 1:200 into L broth and aerated at 37° C. until reaching an OD$_{600}$ of 0.8. The cells were concentrated by centrifugation in a Sorvall GSA rotor at 7,000 rpm for 10 min at room temperature followed by suspension in BSG. The mice to be perorally challenged were deprived of food and water for approximately 4 h prior to the oral challenge. Mice were observed over a period of 30 days for morbidity and mortality. The data from this experiment are reported in Table 12.

TABLE 12

Effectiveness of intranasal immunization with *S. typhimurium* SL 1344 Δcya Δcrp RpoS$^+$ vs. Δcya Δcrp RpoS$^-$ mutants in protecting female BALB/c mice against peroral challenge with wild-type strain χ3339[a]

| Strain | Genotype | Immunizing dose (CFU) | Challenge dose (CFU) | Survivors/ total |
|---|---|---|---|---|
| χ8296 | Δcrp-28 | $1.2 \times 10^9$ | $1.1 \times 10^9$ | 1/4 |
| | Δcrp-27 | | $1.1 \times 10^8$ | 3/4 |
| | ΔasdA16 | $1.2 \times 10^8$ | $1.1 \times 10^9$ | 0/4 |
| | RpoS$^+$ | | $1.1 \times 10^8$ | 1/4 |
| | | | | 5/16 |
| χ8309 | Δcrp-28 | $1.5 \times 10^9$ | $1.1 \times 10^9$ | 0/4 |
| | Δcrp-27 | | $1.1 \times 10^8$ | 1/4 |
| | ΔasdA16 | $1.5 \times 10^8$ | $1.1 \times 10^9$ | 1/4 |
| | rpoS RpoS_ | | $1.1 \times 10^8$ | 0/4 |
| | | | | 2/16 |
| None | BSG | | $1.1 \times 10^8$ | 0/4 |

[a]Strains were grown in Luria broth with DAP. Preparation of bacterial inocula and animal infection were done as described in text. Oral challenge with *S. typhimurium* χ3339 was given thirty days after intra nasal immunization. Mortality was monitored for thirty days after challenge.

As shown in the table, intranasal administration of both the RpoS$^+$ microbe (χ8296) and the RpoS$^-$ microbe (χ8308) provided some protection against challenge by the wild-type strain (χ3339). The RpoS+ strain was more effective, however, in that this strain provided greater protection against challenge with the wild-type strain (5 out of 16 survivors) than did the corresponding RpoS− strain (2 out of 16 survivors).

The experiment in this example utilized Δcya Δcrp Δasd strains of *S. typhimurium* that were either RpoS+ (χ8296) or RpoS− (χ8309). These microbes did not contain an Asd+ plasmid vector which would functionally replace the chromosomal Δasd mutation so that they would be expected to die due to inability to synthesize diaminopimelic acid, within the first 24 hours after intransal immunization. This would, in turn, be expected to diminish the immunologic response that would have been elicited by the microbes had they been endowed with an Asd-containing plasmid that would normally be incorporated into a vaccine microbe. Nevertheless, as noted above, 5 of 16 mice immunized with the RpoS+ strain, χ8296, survived challenge whereas only 2 of 16 mice intranasally immunized with the RpoS− strain, χ8309, survived oral challenge with the wild type *S. typhimurium* strain, χ3339. Thus, even during the first 24 hours after administration, the RpoS+ strain showed a superior ability to elicit a protective immune response.

The experiment described above was repeated using derivatives of χ8296 (RpoS+) and χ8309 (RpoS−) that had been modified by introducing the Asd+ plasmid vector pYA3342 by electroporation. These strains would, therefore, not die due to DAPless death. The strains were grown the same way and the mice were immunized intranasally as described above although the doses used were reduced to ~3×10$^7$ CFU and ~3×10$^8$ CFU. As revealed by the data presented in Table 13, all 18 of 18 mice immunized intranasally with χ8296 (pYA3342), the RpoS+ strain, survived oral challenge with wild-type χ3339 whereas only 17 of 20 mice immunized intranasally with the χ8309(pYA3342), the RpoS− strain, survived oral challenge with χ3339.

TABLE 13

Effectiveness of intranasal immunization with *S. typhimurium* SL1344 Δcya Δcrp Δasd RpoS+ vs Δcya Δcrp Δasd RpoS− strains containing pYA3342 in protecting mice against p.o. challenge with wild-type χ3339*.

| strain | Genotype | Immunizing dose (CFU) | Challenge dose (CFU) | Survivors/total |
|---|---|---|---|---|
| χ8296 (pYA3342) | Δcya Δcrp Δasd (RpoS+) | 3.7 × 10$^8$ | 9.6 × 10$^8$ | 4/4 |
|  |  |  | 9.6 × 10$^7$ | 4/4 |
|  |  | 3.7 × 10$^7$ | 9.6 × 10$^8$ | 5/5 |
|  |  |  | 9.6 × 10$^7$ | 5/5 (18/18) |
| χ8309 (pYA3342) | Δcya Δcrp Δasd rpoS (RpoS−) | 3.5 × 10$^8$ | 9.6 × 10$^8$ | 5/5 |
|  |  |  | 9.6 × 10$^7$ | 5/5 |
|  |  | 3.5 × 10$^7$ | 9.6 × 10$^8$ | 3/5 |
|  |  |  | 9.6 × 10$^7$ | 4/5 (17/20) |

*Four weeks after mice were immunized I.N. with a single dose of the strains, they were challenged P.O. with wild-type SL1344 strain χ3339. Morbidity and mortality observations were recorded daily for an additional 30 days postchallenge. Both inoculating and challenge doses were measured in CFU.

As has been previously reported in the literature, recombinant attenuated *Salmonella* vaccine strains can be administered by various routes to stimulate mucosal and systemic immunity. For example, Srinivasan et al. (*Vaccines* 95, R. N. Chanock et al., Eds., Cold Spring Harbor Laboratory Press, Plainview, N.Y., p 273–280, 1995) and Hopkins et al. (*Infect Immun.* 63:3279–3286, 1995) reported that mice can be immunized not only perorally and intragastrically, but also intranasally, intravaginally and rectally. Nardelli-Haefliger et al. (*Infect Immun* 64:5219–5224, 1996) demonstrated that human volunteers could be immunized rectally with a recombinant attenuated *Salmonella typhi* vaccine strain. More recently, Galan et al. (*Vaccine* 15:700–708, 1998) demonstrated that recombinant attenuated *S. typhi* Ty2 strains of an RpoS− phenotype are able to elicit immune responses when intranasally administered to mice. It is well known that M cells overlie epithelial lymphoid tissues not only in the small intestine (the so-called Peyer's patches which are part of the GALT) but also in the rectum, in the CALT, in the BALT and possibly in other inductive sites leading to mucosal immune responses (*Mucosal Immunology*, 2nd Edition, Ogra et al., Eds. Academic Press, San Diego, 1999). The examples above demonstrated that RpoS+ *Salmonella* invade and collonize epithelial dome M cells in Peyer's patches of the GALT and elicit an immune response following administration by the oral route. This example shows that an immune response is also elicited upon administration by the intranasal route. On the basis of these results, it is logical to infer that RpoS+ *Salmonella* are better able to attach to and invade M cells overlying lymphoid tissues in the upper respiratory tract as well as to the M cells of the GALT than are *Salmonella* strains that are defective with respect to expression of the rpoS+ gene (i.e., are RpoS− in phenotype). It, therefore, follows that immunization of humans with recombinant attenuated *Salmonella* vaccines displaying an RpoS+ phenotype would be more efficacious than those displaying a RpoS− phenotype. Therefore, RpoS+ attenuated *Salmonella* would be superior to RpoS− attenuated *Salmonella* for intranasal, oral, intragastric and rectal immunization. Since administration of attenuated *Salmonella* expressing foreign antigens to colonize mucosal lymphoid tissues is of paramount importance in eliciting mucosal immunity, it follows that such can be accomplished by use of RpoS+ attenuated *Salmonella* of any of various serotypes not only including *S. typhi* but *S. paratyphi A*, *S. paratyphi B*, and *S. paratyphi C*, which are also restricted to humans, but also attenuated derivatives of such other serotypes of *S. enterica* such as *Typhimurium*, *Enteritidis*, *Dublin*, and *Choleraesuis*.

EXAMPLE 8

This example illustrates the superior ability of RpoS+ recombinant attenuated *Salmonella* vaccines to induce mucosal IgA and serum IgG antibodies to an expressed foreign antigen compared to that of the corresponding RpoS− *Salmonella*.

Figure 8:
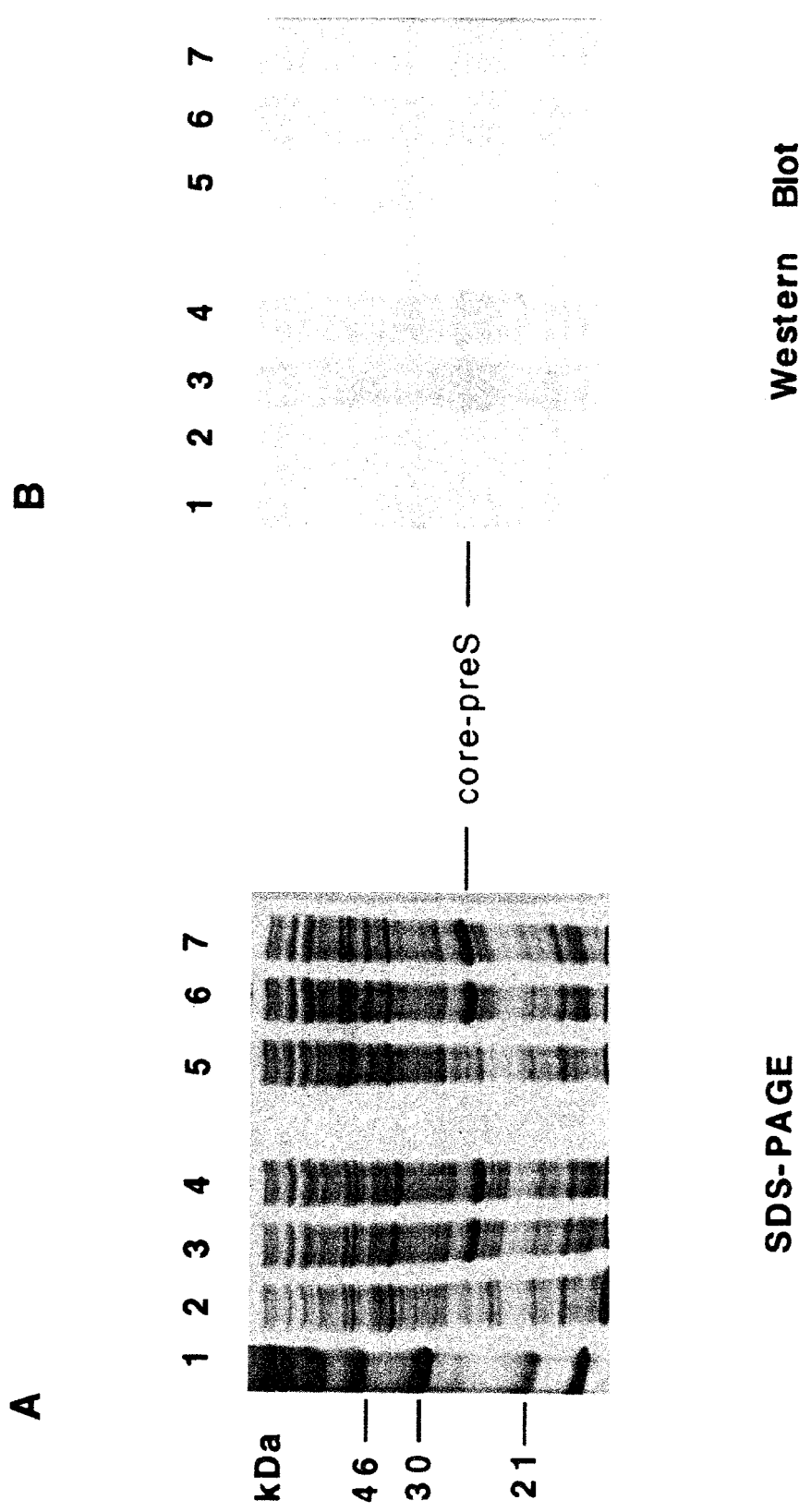

For these studies, the *S. typhimurium* strains used were attenuated with Δcya, Δcrp and Δasd mutations and were of either an RpoS+ phenotype (χ8296; Table 1) or an RpoS− phenotype (χ8309; Table 1). Both of these strains were genetically engineered to produce the hepatitis B virus core (HBVc) particles with pre-S1,S2 fusions according to methods reported in the literature (Schodel et al., *Infect. Immun.* 62:1669–1676, 1994); from pYA3167 (Nardelli-Haefliger et al., supra, 1996). The plasmid specifying the HBVc preS1, S2 fusion was electroporated into χ8296 and χ8309 and the resulting strains were evaluated for production of the HBVc particles with the preS1,S2 epitopes. FIG. 8A depicts Coomassie blue stained SDS gels whereas FIG. 8B depicts the results of analysis of gels by Western blot using a monoclonal antibody 2A42 from Hybridoma-5520 directed at the preS2 epitope. As shown in the figures, both constructs produced the fusion protein which is readily detectable on the Coomassie blue gels as well as following Western blot analysis.

To evaluate the relative immunogenicity of the two strains, groups of female BALB/c mice (eight-weeks old) were perorally immunized with $10^9$ cfu of the pYA3167-transformed vaccine strain derivatives of χ8296 and χ8309. According to the immunization schedule described by Schodel et al. (1994, supra), mice were immunized orally with two doses of vaccine given two days apart. Strains were grown in L broth as standing overnight cultures at 37° C. In the morning, 1:200 dilutions into L broth were grown with moderate aeration until achieving an $OD_{600}$ of 0.8. Bacteria were sedimented by centrifugation and suspended in BSG to desired densities so that the vaccine dose could be administered in a volume of 0.02 ml (20 µl). Food and water were withdrawn from the mice approximately 5 h prior to peroral immunization and were returned 30 min after immunization. Serum samples and vaginal washings were collected 4 and 6 weeks after initial immunization (for methodology, see Zhang et al., *Biol. Reprod.* 56:33–41, 1997). Serum IgG antibody and IgA antibody in vaginal washings were detected by ELISA measuring antibody to a full-length pre-S protein (histidine fusion).

The protocol for ELISA was as follows. Ninety-six-well Immulon-1 plates (Dynatech, Chantilly, Va.) were coated with 10 µg of recombinant HBV pre-S protein (awd)/ml in 0.2 M bicarbonate/carbonate buffer (pH 9.6) at 4° C. overnight. Nonspecific binding sites were blocked with 1% BSA in phosphate buffered saline (PBS)+0.1% Tween20 (pH 7.4) (blocking buffer) at room temperature for 1 h. Serum samples and vaginal washings were diluted 1:100 and 1:10, respectively, in blocking buffer. One hundred microliters of the diluted samples were added in duplicate to the plates and incubated at 37° C. for 2 h. The plates were then washed with PBS+0.1% Tween20 three times. One hundred microliters of biotin-labelled goat anti-mouse IgA or IgG were added, respectively, and incubated at 4° C. overnight. Alkaline phosphatase-labelled ExtrAvidin (Sigma) was added to the plates and incubated at room temperature for 1 h. Substrate solution (0.1 ml) containing p-nitro-phenylphosphate (1 mg/ml) in 0.1 M diethanolamine buffer (pH 9.8) was added and the optical density of the resulting substrate reaction read at 405 nm with an automated ELISA reader (BioTech, Burlington, Vt.). All the reagents were purchased from Sigma (St. Louis, Mo.).

Figure 9:
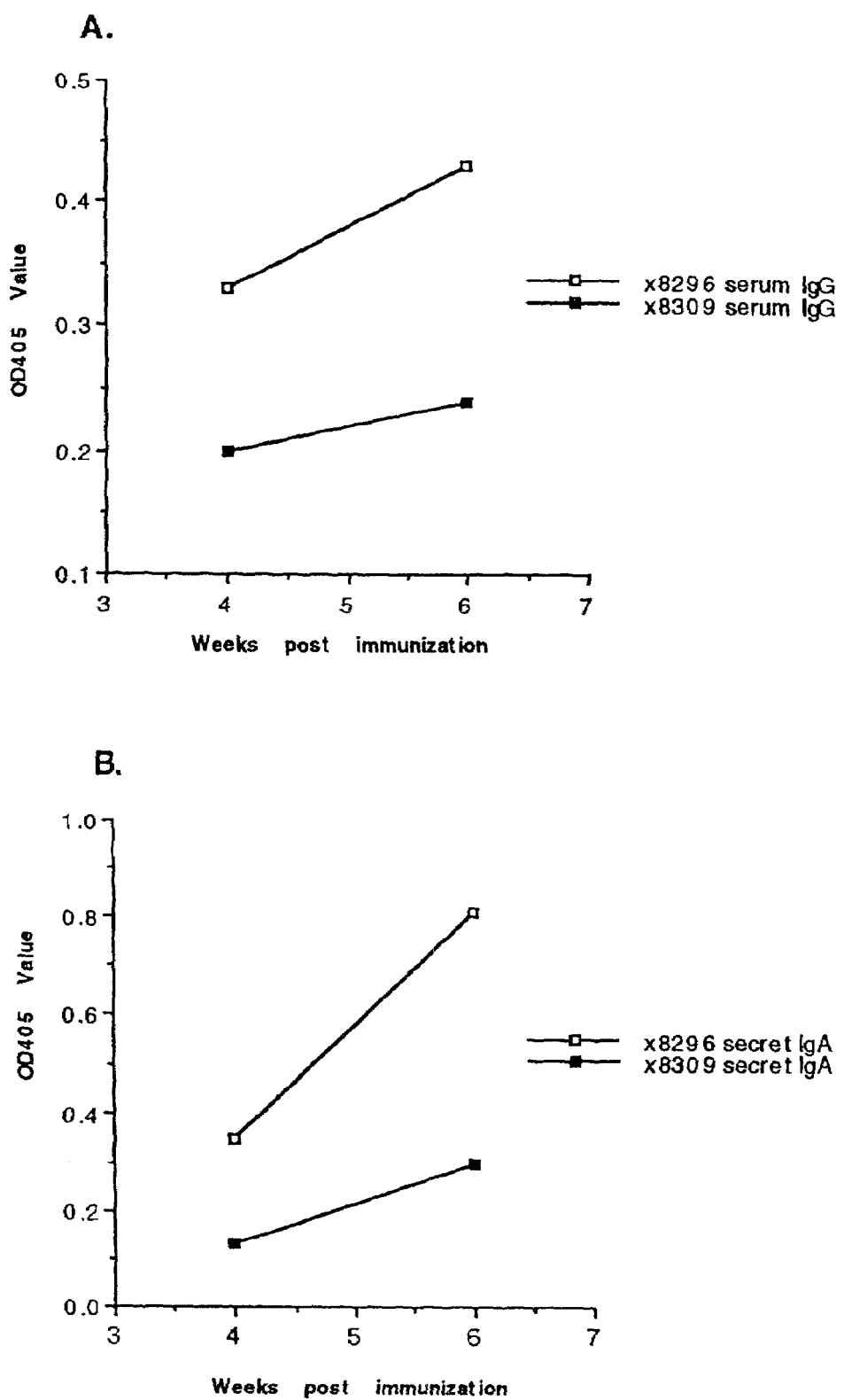

The results of the antibody titer determinations are in FIG. 9. As shown in the figure, the RpoS⁺ recombinant attenuated vaccine strain, χ8296, induced significantly higher antibody titers against the recombinant HBVc preS1, S2 antigen than did the corresponding RpoS⁻ microbe, χ8309, both in serum and in vaginal secretions at 4 and 6 weeks following peroral immunization. It is, therefore, evident that recombinant attenuated *Salmonella* vaccine strains of an RpoS⁺ phenotype are not only superior in inducing protective immunity against *Salmonella* as was shown in Example 7 above, but they are also superior in inducing immune responses against expressed foreign antigens.

Figure 10:
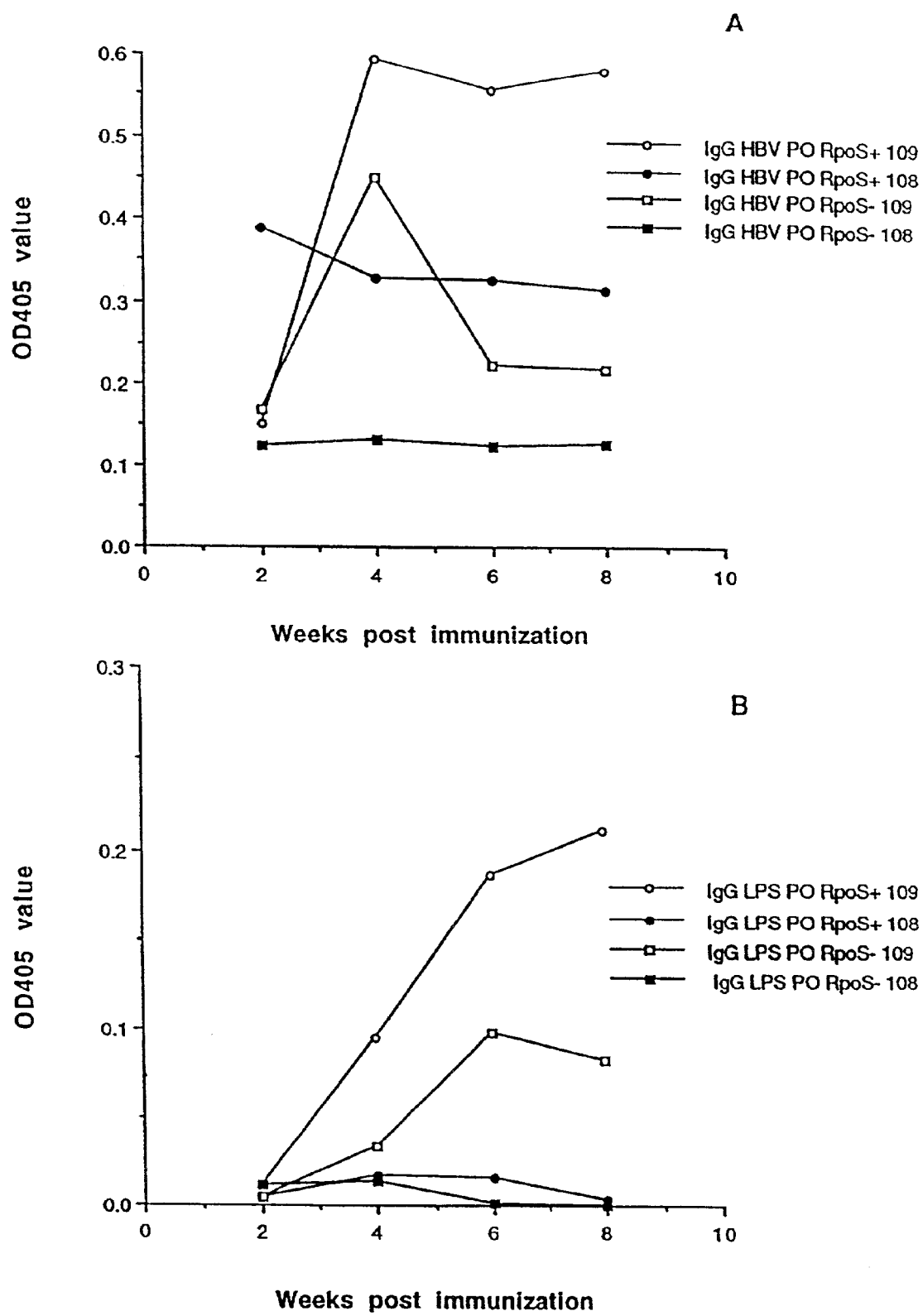
Figure 11:
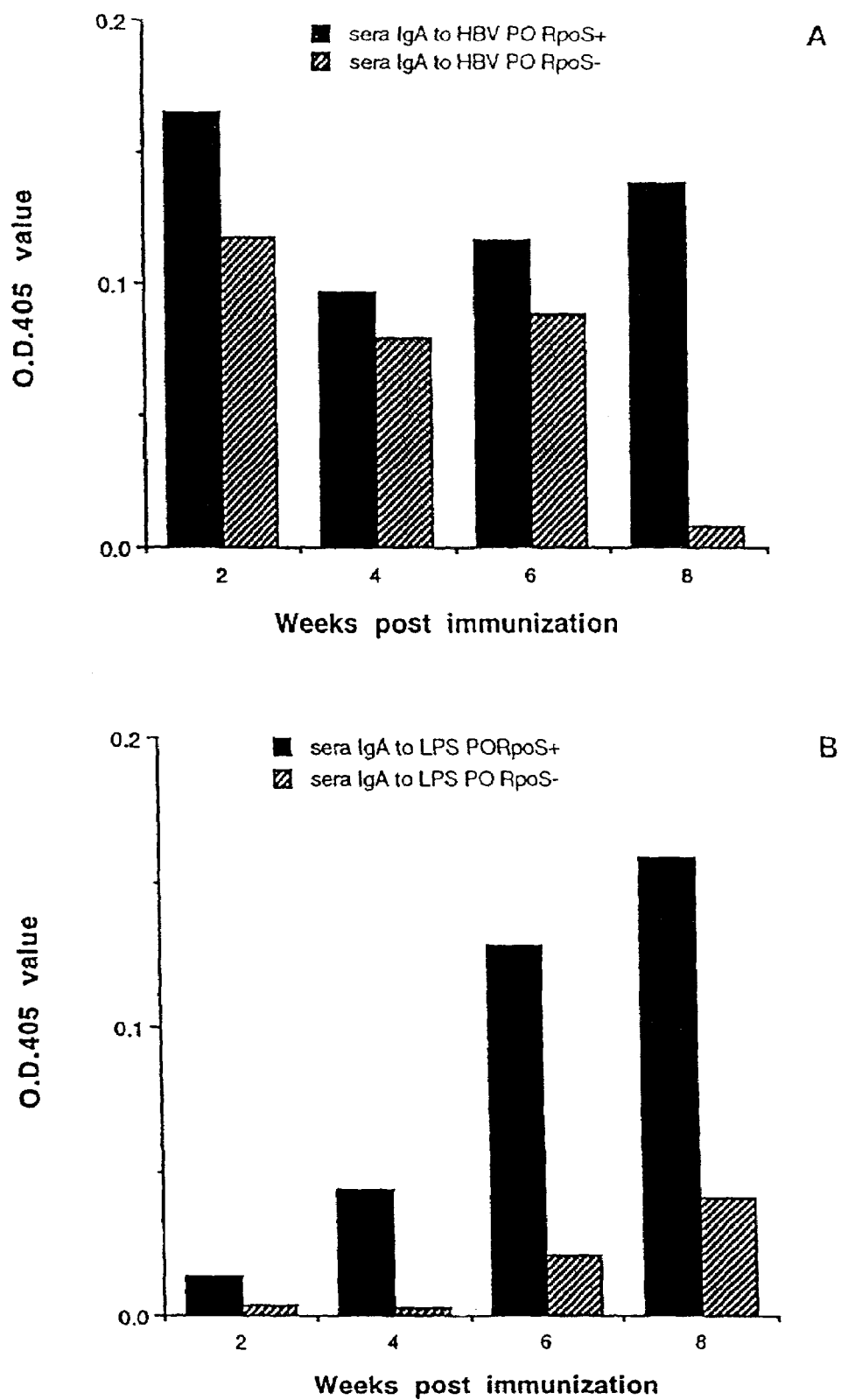

A more extensive repetition of the experiment yielding the data in FIG. 9, corroborated these results and revealed that the isogenic RpoS⁻ vaccine strain, χ8309(pYA3167), not only induced lower IgG and IgA antibody titers to the HBV pre-S peptide than the RpoS⁺ vaccine strain, χ8296 (pYA3167), (FIGS. 10A and 11A), but was also inferior in inducing IgG and IgA antibodies to the *Salmonella* LPS antigen (FIGS. 10B and 11B)

EXAMPLE 9

This example illustrates the method for screening for vaccine strains containing an RpoS⁺ phenotype.

The evaluation of strains for RpoS⁺ phenotype allows the identification and selection of RpoS⁺ strains. Such strains would be expected to show high immunogenicity. Strains for testing in a screening system for RpoS⁺ phenotype can be from any source. For example, strains obtained from depositories can be tested as illustrated below.

Testing for catalase activity and glycogen biosynthesis was performed as described in Example 4 above.

The results of testing for catalase or glycogen synthesis activity in typical *S. typhi* strains are shown below in Table 14. Strains χ8205 and χ8208 did not show catalase activity which is consistent with earlier reports that these microbes are rpoS mutants (Robbe-Saule et al., *FEMS Microbiol. Lett.* 126:171–176, 1995; Coynault et al., *Mol Microbiol.* 22:149–160, 1996). The results of the catalase test suggest that strains χ8204 and χ8207 may also have rpoS mutations, however, the glycogen test was positive for these two strains suggesting that the two strains have an intact rpoS gene. A final decision as to the rpoS allelic state in these two strains would, therefore, require use of other tests as described in Example 4. The remaining strains for which results were obtained in both the catalase and the glycogen test showed corresponding results in both tests.

TABLE 14

Catalase and Glycogen Synthesis Tests on *S. typhi* strains

| Strain | Relevant Genotype | Catalase Activity[a] | Glycogen Synthesis Activity | Source/ Reference |
|---|---|---|---|---|
| χ3743 | ISP1804 Type 46 | ± | + | See Table 1 |
| χ3744 | ISP1820 Type 46 | + | + | See Table 1 |
| χ3745 | ISP2822 Type E1 | + | + | See Table 1 |
| χ3746 | ISP2825 Type E1 | + | + | See Table 1 |
| χ3769 | Ty2 Type E1 | − | − | See Table 1 |
| χ8203 | cys, trp | + | + | ATCC 9992V |
| χ8204 | cys, trp | − | + | ATCC 33458 |
| χ8205 | Ty21a galE, rpoS, cys, trp | − | No Growth | ATCC 33459 |
| χ8206 | cys, trp, aroA serC, purA | + | + | ATCC 39926 |
| χ8207 | cys, trp | − | + | ATCC 10749 |
| χ8208 | Ty2 cys, rpoS | − | − | ATCC 19430 |
| χ8209 | cys, trp | + | + | ATCC 9993 |
| MGN-1256 | Ty2 rpoS cys ΔphoPQ23 ΔasdA16 | − | − | See Table 1 |
| MGN-1191 | ISP1820 cys trp ΔphoPQ23 ΔasdA16 | + | + | See Table 1 |

[a]Vigorous bubbling upon addition of $H_2O_2$ is indicated by +, an intermediate level of bubbling is indicated by ±, and little or no bubbling is indicated by −.

EXAMPLE 10

This example illustrates a method that can be used to introduce a wild-type rpoS allele into RpoS⁻ *S. typhi* strains such as χ3769, MGN-1018 or χ8280 using an allelic replacement strategy.

The wild-type rpoS gene can be introduced into the chromosome of χ3769, MGN-1018 or χ8280 by allelic exchange using the suicide properties of the R6K-based plasmid pMEG-149 or its derivative pMEG-375. Plasmids pMEG-149 and pMEG-375 are mobilizable suicide vectors which carry a λpir-dependent R6K replicon and thus require a host with the pir gene present in trans to allow replication. In addition, pMEG-149 encodes the selectable marker for Ap$^r$ and the counterselectable marker, levanosucrase whereas pMEG-375 also contains the cat gene specifying resistance to chloramphenicol (Cm$^r$). Since pMEG-149 and pMEG-375 cannot replicate in strains lacking the pir gene, selection of Ap$^r$ and Ap$^r$ Cm$^r$ transconjugants, respectively, demands the integration of the plasmid into the chromosome, an event which usually takes place through homology in the inserted fragment.

Figure 12:
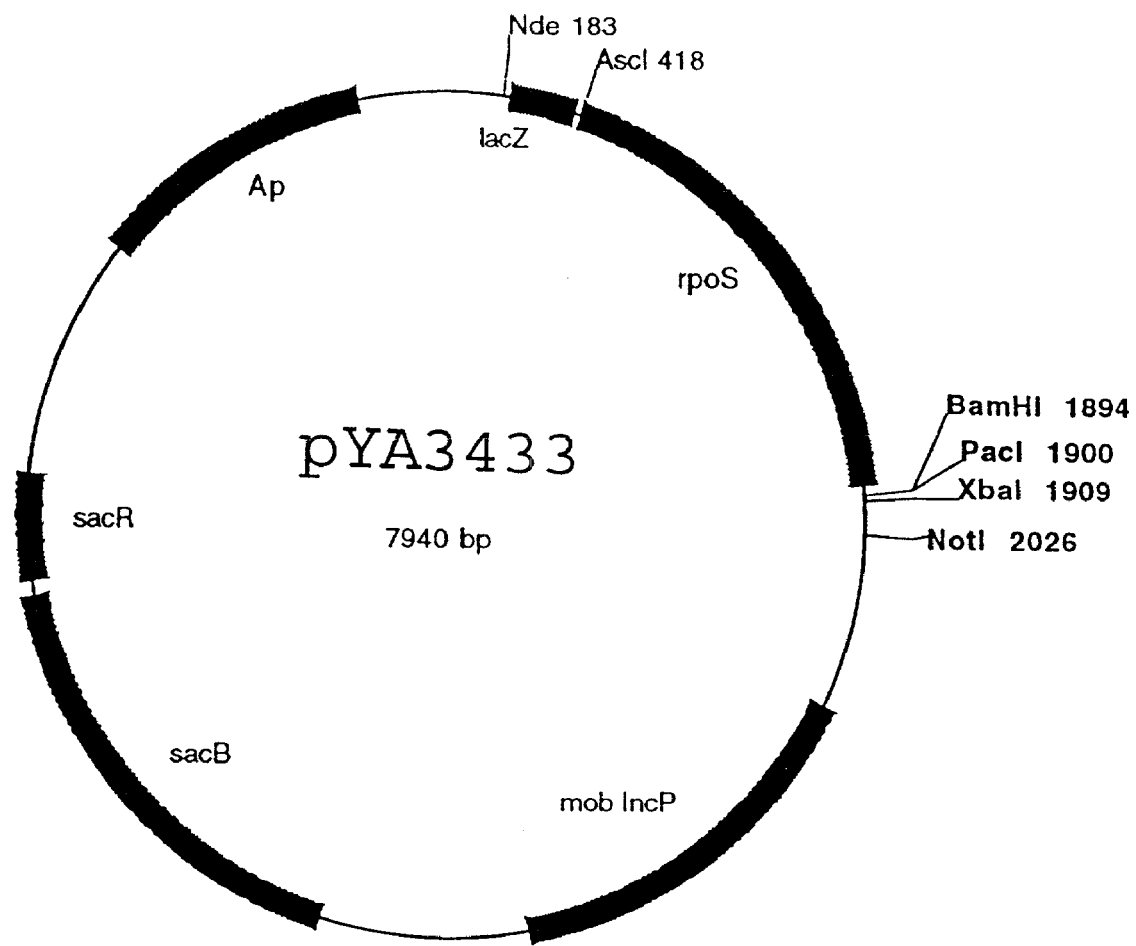
FIG. 12 illustrates the pYA3433 plasmid.

Plasmid pSK::rpoS contains the entire 1.7 kb *S. typhimurium* 14028 rpoS gene cloned into the EcoRV site of pBluescript/SK. The EcoRI-HindIII fragment containing the wild-type rpoS allele from pSK::rpoS was treated with T4 DNA polymerase and cloned into the SmaI site of the suicide vector pMEG-149. The resulting recombinant vector carrying the wild-type rpoS allele designated as pYA3433 (FIG. 12), would be introduced into the λPir$^+$ Asd$^-$ delivery host strain, MGN-617. This strain allows the conjugal transfer of any plasmid containing an IncP mob region to any Asd$^+$ recipient, followed by elimination of the donor on any media lacking diaminopimelic acid (DAP).

Figure 13:
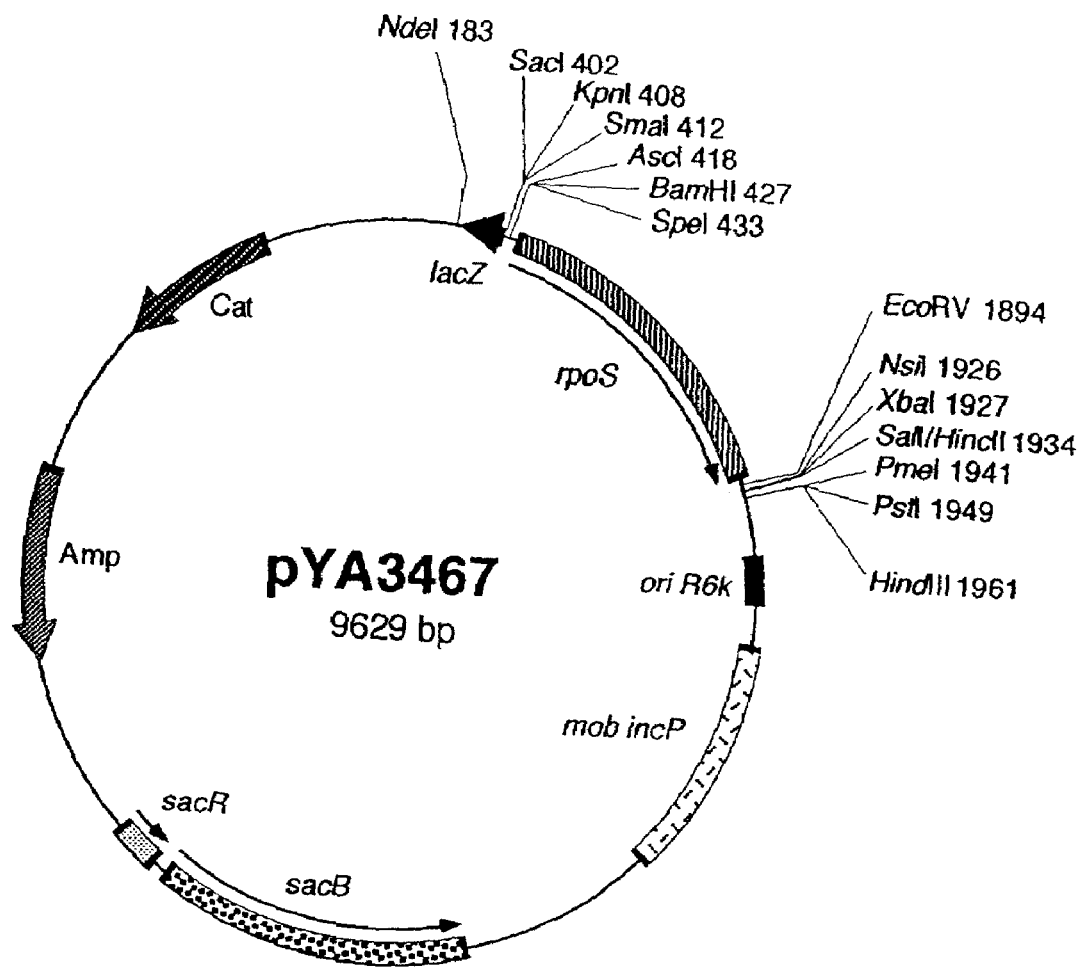
FIG. 13 illustrates the pYA3467 plasmid.

Since duel selection for two drug-resistance genes often enhances selection of merodiploid strains that have integrated a suicide vector into the chromosome by eliminating background growth that sometimes occurs when using Ap$^r$ alone due to the ability of β-lactamase to rapidly destroy the ampicillin in the selective medium, we also made a suicide vector with the rpoS$^+$ gene using pMEG-375 which specifies chloramphenicol resistance in addition to ampicillin resistance. The 1.409 kb *S. typhimurium* UK-1 rpoS$^+$ gene was recovered from pMEG-328 by digestion with PmeI and SmaI and cloned into pMEG-375 digested with the same two enzymes. The resulting suicide vector plasmid, pYA3467, is depicted in FIG. 13.

Plasmid pYA3467 carrying the wild-type rpoS allele was introduced via MGN-617 into the ΔphoPQ Δasd *S. typhi* Ty2 strain, MGN-1018, by electroporation. Transformants were selected by spreading on L-agar plates supplemented with DAP (100 μg/ml), ampicillin (50 μg/ml) and chlormphenicol (40 μg/ml) followed by incubation overnight at 37° C. Ampicillin- and chloramphenicol-resistant isolates obtained from this transformation procedure represent the integration of the entire plasmid including the wild-type rpoS allele into the chromosome by a single crossover event. Such isolates contain two copies of the rpoS gene, ie. a wild-type and a mutated rpoS allele. The isolates were then screened on Luria agar supplemented with DAP (100 μg/ml) and containing 5% sucrose to select for loss of the suicide vector sequences by a second crossover event. Sucrose-resistant isolates were screened for sensitivity to ampicillin and chloramphenicol and for the presence of a functional rpoS allele (using the catalase or glycogen synthesis test).

After identifying bonifide rpoS$^+$ derivatives, complete characterization is done to verify the presence of LPS, Vi antigen, all attenuating mutations and the presence of all other traits that are characteristic of an RpoS$^+$ derivative of the MGN-1018 parent. One such derivative was selected as χ8434 (Table 1). Since the wild-type *S. typhi*, Ty2 strain may possess excellent attributes as a recombinant attenuated *Salmonella* vaccine vector if provided with an RpoS$^+$ phenotype, the wild-type Ty2 strain χ3769 was also endowed with the rpoS$^+$ gene from pYA3467 using the method described above to generate the RpoS$^+$ derivative χ8438 (ATCC 202182) (Table 1). This strain can now be attenuated by introducing various defined deletion mutations as described in Examples 2 and 3 and then endowed with the ability to express various antigens as described in Example 11 below.

In order to further validate the method, pYA3467 was transferred by the donor MGN-617 to the candidate recombinant attenuated vaccine strain χ8280 [Ty2 ΔphoPQ23 rpoS ΔasdA16 (pYA3167)]. This strain synthesizes the hepatitis B virus core with pre S1, S2 epitopes due to the presence of pYA3167. Using the procedures described above, an RpoS$^+$ derivative was isolated and fully characterized. This was designated χ8435 (Table 1).

The abilities of these three RpoS$^+$ strains, constructed by introducing a recombinant wild-type rpoS$^+$ gene to replace the defective rpoS mutant gene present in *S. typhi* Ty2 and its descendents, to synthesize glycogen and to give a positive catalase test are shown in Table 14.

TABLE 15

Test for RpoS Phenotype in Recombinant Salmonella Strains and Their Parents.

| Salmonella typhi Ty2 | Glycogen Accumulation/ Biosynthesis | Catalase Activity |
|---|---|---|
| χ3769 *S. typhi* Ty2 wild-type | − | − |
| χ8438 *S. typhi* Ty2 rpoS$^+$ | + | + |
| MGN-1018; *S. typhi* Ty2 ΔphoPQ23 | − | − |
| χ8434 *S. typhi* Ty2 ΔphoPQ23 rpoS$^+$ | + | + |
| χ8280 (pYA3167) *S. typhi* Ty2 ΔphoPQ23 ΔasdA16 | − | − |
| χ8435 (pYA3167) *S. typhi* Ty2 ΔphoPQ23 ΔasdA16 rpoS$^+$ | + | + |

This method can also be used to introduce a recombinant wild-type rpoS gene into various Ty2 derived vaccine strains such as ATCC 55117 (χ3927; Δcya-12 Δcrp-11) or ATCC 55118 (χ4073; Δcya-12 Δ[crp-cdt]-10) to improve the balance between attenuation and immunogenicity.

EXAMPLE 11

This example illustrates the construction of recombinant attenuated rpoS$^+$ *S. typhi* strains expressing foreign antigens for use as oral vaccines to immunize against various infectious diseases.

The rpoS$^+$ vaccine strains are prepared based upon *S. typhi* strains containing a functional rpoS gene such as ISP1820 using defined deletions as described above in examples 2 and 3 or based upon attenuated rpoS mutant strains such as Ty2 which have a recombinant rpoS gene as described in example 10 above. In the construction of vaccines expressing foreign antigens, the preferred approach is to use a balanced, lethal host-vector system which confers stable maintenance and high-level expression of cloned genes on recombinant plasmids. For this, a chromosomal mutation of the asd gene encoding aspartate β-semialdehyde dehydrogenase is introduced into the RpoS$^+$ strain to impose an obligate requirement for diaminopimelic acid (DAP) which is an essential constituent of the rigid layer of the bacterial cell wall and which is not synthesized in humans. The chromosomal Δasd mutation is then complemented by a plasmid cloning vector possessing the wild-type asd+ gene as well as a recombinant gene encoding the desired foreign antigen. Loss of the plasmid results in DAP-less death and cell lysis. Such balanced-lethal host-vector combinations are stable for several weeks in the immunized animal host and elicit immune responses against the cloned gene product as well as against *Salmonella*.

The construction of a defined deletion in the chromosomal asd gene is described in example 3 above. The ISP1820 derivative, MGN-1191 and the Ty2 derivative, MGN-1256, which have ΔphoPQ23 and ΔasdA16 mutations were thus produced. The asd-complementing plasmid containing a recombinant gene encoding the desired foreign antigen can be constructed as described in U.S. Pat. No. 5,672,345. For example, one such plasmid expressing the Hepatitis B virus antigenic nucleocapsid pre-S1 pre-S2 (HBcAg-pre-S) particles, designated as pYA3167, has been constructed as reported in the literature (Schodel, et al., 1996, in Novel strategies in design and production of vaccines. S. Cohen and A. Shafferman, eds., Plenum Press, New York). Accordingly, *S. typhi* MGN-1191 and MGN-1256 have been transformed with plasmid pYA3167 via electroporation. Immunoblot analysis with HBV pre-S2-specific monoclonal antibody was used to determine the level of expression of the hybrid core pre-S gene in the transformed attenuated *S. typhi* carrier strains derived from MGN-1191 and MGN-1256. The expression of the hybrid HBcAg-pre-S antigen in ΔphoPQ Δasd mutant *S. typhi* strains was determined as follows. Proteins from whole bacterial cell lysates after overnight culture were separated using 12% sodium dodecyl sulfate (SDS-12%), polyacrylamide gel electrophoresis (PAGE) and stained with Coomassie brilliant blue. Results are shown in FIG. 14. Three transformants of MGN-1191 and three transformants of MGN-1256 were studied all of which showed a band at the position of the recombinant antigen (see arrow in FIG. 14). The MGN-1191 transformant #1 (lane 3) was designated χ8281 and the MGN-1256 transformant #1 (lane 7) was designated χ8280. Both strains express the Vi capsular antigen as determined by positive agglutination with Vi antiserum (Difco).

In addition, the expression of the recombinant antigen was assessed by immunoblotting. For immunoblotting, cells from overnight cultures were taken up in 2× sample buffer and boiled for 10 minutes to lyse the cells. Proteins were separated by SDS-12% PAGE. The proteins were subsequently transferred to nitrocellulose; incubated with monoclonal antibodies specific for HBV pre-S2; developed with peroxidase-coupled goat anti-mouse immunoglobin G (IgG) (heavy and light chains) and visualized on X-ray film (Kodak) after incubation with a chemiluminescent substrate (ECL; Amersham). Results are shown in FIG. 15. As was seen with Coomassie staining, the three transformants of MGN-1191 including χ8281 (lane 3) and the three transformants of MGN-1256 including χ8280 (lane 7) all showed a band at the position of the recombinant antigen (see arrow in FIG. 15).

For immunoscreening, the following procedure can be used. Bacterial colonies are lifted onto nitrocellulose filters and lysed in 1% SDS for 30 minutes at 70° C. Free binding sites on nitrocellulose are blocked by 10% horse serum in Tris-HCl-buffered saline. Subsequently, immunoscreens are treated like immunoblots and secondary goat anti-mouse IgG (heavy and light chains) is visualized with nitroblue tetrazolium-5-bromo-4-chloro-3-indolylphosphate toluidinium (Promega).

*S. typhi* rpoS+ strains expressing foreign antigens can also be constructed using plasmid vectors with selectable markers other than Asd+, including genes that confer resistance to drugs such as ampicillin and tetracycline. In addition, the recombinant vector encoding the desired foreign antigen may be constructed using well known techniques such that the vector will insert into the bacterial chromosome by homologous recombination or by transposition.

EXAMPLE 12

This example illustrates methods which can be used in constructing recombinant attenuated vaccine strains that express foreign proteins so as to suppress, modulate, or augment immune responses in a beneficial way.

It is well known that live attenuated bacterial vaccines induce long-lasting immunity by inducing T helper lymphocyte memory functions. *S. typhimurium* infection of mice leads predominantly to a Th-1 type of response although a Th-2 response with production of SIgA in mucosal secretions and serum antibodies against *Salmonella* and against foreign expressed antigens is also induced. IL-10 can be detected at levels indicating the occurrence of the Th-2 response (Van Cott et al., *J. Immunol.* 156:1504–1514, 1996). It also known that the recombinant attenuated *S. typhimurium* vaccine can also induce a CTL response involving CD-8+ cells against a foreign antigen (Sadoff et al., *Science* 240:336, 1988). In many cases, however, it would be desirable if a recombinant attenuated *Salmonella* vaccine elicits predominantly a Th-2 type of response to enhance mucosal immunity by the production of SIgA and a cellular memory response for that SIgA production. The lymphokines IL-4 and IL-5 when produced, potentiate such a Th-2 response. On the other hand, it is desirable in other instances to maximize the ability of the recombinant attenuated *Salmonella* to induce a Th-1 type of response which might be particularly important in providing protective immunity against a facultative or obligate intracellular parasite whose antigens are expressed by the recombinant attenuated *Salmonella* vaccine. Shifting the immune response to a predominantly Th-1 or to a Th-2 type of response can be achieved in part by expressing lymphokines via recombinant attenuated *Salmonella* strains. Thus, we have constructed *Salmonella* strains expressing IL-2 which enhances the Th-1 type of response and also potentiates a CTL response which is important in designing attenuated *Salmonella* vaccines to be protective in combating certain types of cancer (Saltzman et al., *Cancer BioTher. Radiol. Pharm.* 11:145–153, 1996; Saltzman et al., *J. Pediatric Surg.* 32:301–306, 1997). Generating the *Salmonella* to induce a predominant Th-2 response can be achieved by causing the strains to express IL-4 and IL-5 as has been done for the latter lymphokine by Whittle et al. (1997, *J. Med. Microbiol.* 46:1029–1038). IL-4 has been expressed by a recombinant aroA attenuated *Salmonella* vaccine strain but was not effective since it was not secreted (Denich et al., *Infect. Immun.* 61:4818–4827, 1993). Methods such as described by Hahn et al. (*FEMS Immunol. Med. Microbiol.* 20:111–119, 1998) are now available to succeed in such secreted expression of lymphokines by attenuated *Salmonella*. It is also possible to coexpress peptides such as factor P which is reported to stimulate the secretion of SIgA. Genes for cDNAs have been obtained which specify many different lymphokines, cytokines and other peptide or protein molecules which act to modulate the immune response. It is anticipated that these peptides or proteins could be coexpressed by recombinant attenuated *Salmonella* vaccine strains expressing some antigen from a particular pathogen or from a tumor cell line or some other molecule that was targeted for an immune response that would induce an immune response to protect against an infectious disease or to therapeutically correct against a systemic disease of the immunized human. Thus IL-6 has been expressed and in some cases secreted by recombinant attenuated *Salmonella* (Dunstan et al., *Infect Immun* 64:2730–2736, 1996; Hahn et al., *FEMS Immunol Med Microbiol* 20:111–119, 1998). The genes for murine macrophage inhibitory factor (MIF), IL-2, IFN-γ or TNF-α were individually cloned and expressed by recombinant attenuated *Salmonella* to alter immune responses against *Leishmania major* infection (Xu et al., *J. Immunol.* 160:1285–1289, 1998). TGF-β has also been expressed in recombinant attenuated *Salmonella* vaccine strains to decrease the inflammatory response by inhibiting endogenous synthesis of IL-2 and INF-γ but enhancing synthesis of IL-10 (Ianaro et al., *Immunology* 84:8–15, 1995). Based on data presented in preceding examples, it is evident that recombinant attenuated *Salmonella* vaccines of the RpoS$^+$ phenotype will be superior to vaccine strains of an RpoS$^-$ phenotype in expressing cytokines and other immunoactive molecules to suppress, enhance and/or modulate the immune response in a desired way.

EXAMPLE 13

This example illustrates methods which can be used in constructing recombinant attenuated vaccine strains to combat cancer by supressing tumor growth, by enhancing the immunized individuals immune system to eliminate tumor cells and/or by inducing an immune response against a tumor-specific antigen.

As stated in Example 12 above, we have constructed *Salmonella* strains expressing IL-2 which enhances the Th-1 type of response and also potentiates a CTL response which has been effective in decreasing metastases by murine adenocarcinoma MC-38 (Saltzman et al., 1996: Saltzman et al, 1997). Based on results presented, it is evident that a recombinant attenuated *Salmonella* vaccine designed to supress tumor growth and spread would be more efficacious if displaying an RpoS$^+$ phenotype rather than a RpoS$^-$ phenotype.

It is known that *Salmonella* will seek out and partially destroy solid tumors following infection of a tumor-bearing individual. (Pawelek et al., *Cancer Res* 57:4537–4544, 1997). Such wild-type *Salmonella* ultimately kill the host as well as destroy the tumor. It is, therefore, necessary to attenuate the *Salmonella* and also to modify it to eliminate the inflamatory response resulting from the induction of TNFα by the lipid A moiety of LPS. This has been accomplished by using a purine-requirement mutant that is attenuated with an inactivated msbB gene which renders the lipid A non-inflammatory (Low et al, *Nature Biotechnol.* 17:37–41, 1999). Such strains can be further modified by introduction of a Δasd mutation and endowed with an Asd$^+$ plasmid vector specifying an enzyme that converts a non-toxic prodrug into an anti-tumor drug within the tumor to further enhance the rate of tumor destruction (see, for example, WO9913053). Based on results presented, it is evident that a recombinant attenuated *Salmonella* vaccine designed to supress tumor growth and spread would be more efficacious if displaying an RpoS$^+$ phenotype rather than a RpoS$^-$ phenotype.

The attenuated *S. typhi* strains with the balanced-lethal host-vector system as described in Example 11 can also be used to express tumor-specific antigens to create a therapeutic anti-cancer vaccine. Such vaccines would thus be endowed with the ability to express a specific tumor-specific antigen often fused to a T-cell epitope to enhance induction of a CTL response. Such a vaccine could also be enhanced by secreting IL-2 and rendered less inflamatory by introducing a msbB mutation or one of similar effect in depressing the inflamatory effect of lipid A. Based on results presented, it is evident that a recombinant attenuated *Salmonella* vaccine designed to supress tumor growth and spread would be more efficacious if displaying an RpoS$^+$ phenotype rather than a RpoS$^-$ phenotype.

EXAMPLE 14

This Example illustrates the use of attenuated RpoS$^+$ *Salmonella* strains having high immunogenicity and low virulence, to express an autoantigen and to exert an antifertility benefit.

We have previously described how to use recombinant attenuated *Salmonella* strains to express autoantigens so as to induce a state of infertility. This technology is disclosed in U.S. Pat. No. 5,656,488. In addition, Srinivasan et al. (*Biol. Reproduct.* 53:462–471, 1995) describes how to express a sperm-specific antigen from a recombinant attenuated *Salmonella* so as to induce antibodies against that sperm antigen to effectively block the sperm-egg interaction in the mouse to induce a state of infertility. The specific antigen was specified by a murine cDNA sequence and the recombinant *Salmonella* was able to induce in mice an immune response against that autoantigen. Similarly, Zhang et al. (1997, Biol. Reproduct 56:33–41) expressed in an attenuated *S. typhimurium* strain, the murine cDNA sequence encoding the zona pellucida antigen, ZP-3. Mice immunized with *Salmonella* expressing this autoantigen mounted an immune response to ZP-3. Antibodies to ZP-3 coated the surface of ova in the ovary and effectively reduced the ability of sperm to fertilize such eggs. It is also well known that fusion of an autoantigen to a carrier antigen which is heterologous to the host can lead to the induction of an immune response which recognizes the autoantigen as well as the heterologous carrier. In the case of fertility, such immunization strategies could lead to the development of contraceptive vaccines.

EXAMPLE 15

This Example illustrates the use of an attenuated RpoS$^+$ *Salmonella* vaccine engineered to express an allergen and to induce an immune response to ameliorate the effect of that allergen.

Allergies to pollens, mold spores, insect parts, animal dander and the like are due to the inhalation of air and/or ingestion of food containing such allergens. The allergies that result are associated with a presence of IgE antibodies that bind to allergens which activate mast cells for release of histamines. As is well known, desensitization against allergens can be achieved by repetitive parenteral immunization of extracts containing the allergen. Likewise, it is known that oral ingestion of raw honey containing pollens can be used to effectively induce a state of tolerance against those allergens. Oral ingestion with such allergens can on the one hand induce an SIgA response that could block the ability of allergens to react with IgE and mast cells or if administered in sufficient quantity could serve to suppress the synthesis of IgE antibodies, that is to induce tolerance. Since the specific allergenic molecule in many allergens has been identified and the cDNA cloned to obtain the nucleotide sequence specifying the allergen, it is now possible to genetically engineer heterologous host cells to express the allergen (see for example, Valenta et al, *Allergy* 53:552–561. 1998; Olsson et al., *Clin. Exp. Allergy* 28:984–991. 1998; Soldatova et al., *J. Allergy Clin. Immunol.* 101:691–698, 1998; Asturias et al, *Clin. Exp. Allergy* 27:1307–1313; Twardosz et al, *Biochem. Biophys. Res. Comm.* 239:197–204, 1997). Accordingly, the attenuated RpoS+ *Salmonella* of the present invention can be engineered to express an allergen, possibly in a modified immunogenic but nonallergenic form to induce a state of tolerance or to actively promote the production of SIgA against the allergen. The RpoS+ attenuated *Salmonella* described herein have been shown to be effective in eliciting immune responses and, hence, it follows that use of such RpoS+ *Salmonella* to express modified allergens would be likely to be effective in ameliorating the consequences of exposure of humans to allergens by inhalation or ingestion.

EXAMPLE 16

This example illustrates a procedure that can be used for testing the safety, immunogenicity and efficacy of live oral vaccines comprising recombinant attenuated rpoS+ *S. typhi* carrier strains which express a desired foreign antigen.

Strains tested are attenuated derivatives of ISP1820 and ISP1822 or attenuated derivatives of Ty2 strain $\chi$8438 (Table 1) containing a recombinant rpoS gene.

The Individuals Studied: The individuals studied are volunteers who are healthy adult humans age 18–40 years of either sex. The prospective volunteers are screened before the study. The inclusion criteria includes:
1. general good health;
2. evaluation of medical history;
3. normal and regular bowel habits;
4. normal physical examination;
5. normal laboratory findings including:
   normal urinalysis,
   normal complete blood count and differential,
   normal blood chemistries (SGPT, alkaline phosphatase, BUN, creatinine, fasting blood glucose),
   negative ELISA for HIV-1
   negative pregnancy test (females);
6. able to understand and comply with required procedures including the practice of good hygiene, maintenance of daily logs and willingness to undergo stool collection.

The exclusion criteria includes:
1. history of gall bladder disease;
2. gastric achlorhydria (frequent antacid, $H^2$ blocker or $B_{12}$ usage);
3. history of immunodeficiency;
4. positive pregnancy test (females)
5. medical, psychiatric or occupational condition which would preclude compliance with protocol;
6. diarrheal illness;
7. history of antibiotic therapy within 7 days prior to immunization;
8. history of drug allergy or serious adverse reaction to vaccines.

Volunteers are screened and informed written consent is obtained.

Study Design: Groups of 5 or 6 volunteers are studied for each strain and dose. In the first group of volunteers, the subjects will receive a single dose of $10^5$ CFU of the attenuated vaccine. If this group develops no clinical symptoms of disease, an escalation in dose will proceed in subsequent groups to establish the maximal safe and minimal immunogenic dose. Subsequent groups will receive $10^6$ CFU or greater doses up to a maximal dose of $10^9$ CFU.

Preparation of the vaccine inocula: Stock cultures of the *S. typhi* candidate vaccine strains are stored as a cell suspension in 1% bactopeptone (Difco) containing 5% glycerol at −70° C. To make an inoculum of the strain, the suspension is thawed and then diluted to the appropriate CFU/ml for the particular dose.

Inoculation of Volunteers: On the day of inoculation of volunteers, blood, urine and stool samples are obtained and baseline values for clinical laboratory parameters are determined. In addition, immunoglobins are measured in serum and stool samples. The subjects receive nothing by mouth for 90 minutes before inoculation. Two grams of $NaHCO_3$ are dissolved in 5 ounces of distilled water. The subjects will drink 4 ounces of the bicarbonate water and one minute later the subjects will ingest the vaccine suspended in the remaining one ounce of bicarbonate water. Subjects will take no food or water for 90 minutes after inoculation.

Clinical monitoring of volunteers: The volunteers are followed as inpatients for a minimum of two weeks and thereafter as outpatients up to a total of four weeks. During this period observations are made for any adverse effects including but not limited to fever, headache, chills, vomiting, diarrhea and abdominal pain. Blood and stool samples are obtained during the testing period and cultures and antibody determinations are done. In addition, PCR for vaccine strain is done on serum. Any volunteer who develops a temperature of 100.8° F. at any time during the study will have stool samples and blood drawn for culture; if the temperature remains elevated for 12 hours and/or blood culture is positive, a 10 day course of oral antibiotics will be given.

Procedures for Specimen Collection.

Stool Specimens: A record will be kept of the number, consistency and description of all stools passed by volunteers for 14 days post vaccination. Stool volume will be measured and the stool will be graded on a 5 point system:
Grade 1—firm stool (normal)
Grade 2—soft stool (normal)
Grade 3—thick liquid (abnormal)
Grade 4—opaque watery (abnormal)
Grade 5—rice water (abnormal)

Stool cultures will be performed on a sample of stool (or rectal swab if stool was not passed) each day on consecutive days for *Salmonella* until negative times one.

Phlebotomy: Serum (20 ml blood) will be collected for prescreening evaluation. Serum for antibody (10 ml blood) determinations will be obtained on days 0, 7, 14 and 28. Heparinized blood for lymphocyte separation (30 ml) for antibody-secreting cell assays by ELISPOT will be collected on days 0, 7, 14 and 28 on a subset of volunteers. The subset will consist of 2 volunteers in groups 3, 4 and 5. Volunteers will be selected randomly by the computer. Blood (10 ml) will be obtained for culture on each day until negative during the post immunization observation period to detect viable vaccine organisms by both conventional culture and PCR. In total, no more than 450 ml of blood will be collected from any volunteer during any 2 month period. Bacteria in positive blood cultures will be evaluated for conformity to the genotype/phenotype of the vaccine strain.

Bacteriology: Stools and rectal swabs will be inoculated into selenite-cystine broth. Stools must be processed within 48 hours. After overnight incubation at 37° C., subcultures will be made onto XLT-4 agar. Colonies which appear consistent with *Salmonella* will be processed through API- 20 system of identification and confirmation made by a agglutenation with *S. typhi* O, H, and Vi antisera. These isolates will be saved at −70° C. in 5% glycerol-1% peptone for further analysis (e.g., for the presence of plasmids, for absence or presence of specific DNA sequences using PCR, or for Southern blotting with gene probes for cloned genes).

Blood cultures (10 ml) will be inoculated in 50 ml Septacheck bottles. Positive cultures are analyzed and saved as described above.

Immunology: Sera specimens will be tested for IgA, IgM and IgG to *S. typhi* O, H and Vi antigens measured by ELISA. H antibody will also be measured by Widal tube agglutination using *S. virginia* as antigen (*S. manhatten* also shares the identical flagellar antigen as *S. typhi* but not somatic antigen). Peripheral blood mononuclear cells will be collected and separated for antibody secreting cell (ASC) assays employing ELISPOT for cells producing antibody to *Salmonella* antigens. Lymphocytes that secrete IgG, IgA, or IgM against *S. typhi* O, H, or Vi antigens will be measured.

PCR: The *Salmonella* invA gene segment will be amplified by polymerase chain reaction to confirm the presence or absence of *Salmonella typhi* in blood specimens. The invA sequence is unique to *Salmonella* (Galan and Curtiss, 1991) and is diagnostic for the presence of invasive *Salmonella* by PCR methods (Rahn et al., 1992).

Excretion of the Vaccine Strain: It is expected that excretion of the vaccine strain would cease within 1 week after a dose of vaccine. If excretion continues for 7 or more days, the volunteer who continues to excrete is given a dose of ciprofloxacin (700 mg every 12 hours). Negative cultures for a ≧2 consecutive days are required for discharge.

EXAMPLE 17

This Example illustrates the potential use of attenuated RpoS⁺ *Salmonella enterica* of various serotypes for intranasal administration to elicit superior mucosal and systemic immune responses. Such candidate vaccines can also be administered orally, conjunctivally, or rectally.

The *Salmonella enterica* serotypes are, preferably, attenuated with known attenuation approaches such as by generating deletion mutations in a pab gene, a pur gene, an aro gene, asd, a dap gene, nadA, pncB, galE, pmi, fur, rpsL, ompR, htrA, hemA, cdt, cya, crp, dam, phoP, phoQ, rfc, poxA, galU, metL, metH, mviA, sodC, recA, ssrA, ssrB, sirA, sirB, sirC, inv, hilA, hilC, hilD, rpoE, flgM, tonB, slyA, or in a combination of these genes. Furthermore, the microbes would have an RpoS⁺ phenotype as determined by the catalase test or the glycogen synthesis test as described in Example 4. The RpoS⁺ attenuated *Salmonella enterica* strains could be of the serotypes *Typhi, Paratyphi A, Paratyphi B, Paratyphi C, Typhimurium, Enteritidis, Dublin,* or *Choleraesuis.* In the wide host range *S. enterica* serotypes, *Typhimurium* and *Enteritidis,* and in the more host-adapted serotypes, *Dublin* and *Choleraesuis,* it is desirable that they possess the *Salmonella* virulence plasmid which enhances their immunogenicity due to more rapid growth in intracellular in vivo environments (Gulig in *Escherichia coli* and *Salmonella*, Vol 2, F. Neidhardt et al., Editor, American Society for Microbiology, Washington D.C., pp. 2774–2787, 1996).

Study design for testing safety and efficacy in humans are as described in Example 16 above except for the serotype of *Salmonella* to be administered and the nasal route of immunization. Table 16 lists parental vaccine vector strains with differing serotypes and their test results for catalase and glycogen synthesis to indicate the RpoS⁺ phenotype.

TABLE 16

Determination of RpoS Phenotype of Bacterial Strains.

| Bacterial species | Glycogen Accumulation/ Biosynthesis[a] | Catalase Activity |
|---|---|---|
| χ3246 *Salmonella choleraesuis* | − | + |
| χ3759 *Salmonella enteritidis* | + | + |
| χ3841 *Salmonella infantis* | + | + |
| χ4952 *Salmonella pullorum* | + | + |
| χ4821 *Salmonella dublin* | n.g. | + |
| χ8274 *Salmonella typhimurium* 14028s | + | + |
| χ8219 *Salmonella paratyphi* A | + | − |
| χ8436 *Salmonella paratyphi* C | + | + |
| χ8437 *Salmonella sendai* | + | + |
| *Shigella flexneri* 2a 2457T | n.g. | + |
| *Shigella flexneri* 2a 15D | not tested | + |

[a]n.g.-no growth on Q-3 medium.

Note that *S choleraesuis* χ3246 is unable to synthesize glycogen, however, it tests as RpoS⁺ by the catalase test. *S. paratyphi* A, χ8219 synthesizes glycogen indicating an RpoS⁺ phenotype, but lacks the catalase regulated by the rpoS gene. Any of these strains can be attenuated by the methods described in Examples 2 and 3 and further modified with the asd mutation for use of an Asd⁺ vector encoding for a foreign antigen such as the pYA3167 specifying the hepatitis B virus core pre-S1/preS-2 fusion as described in Example 11 and used in Example 8. All of these strains display the RpoS⁺ phenotype.

The other difference between the procedures described in Example 16 is the route of immunization. Intranasal immunization can be achieved by administration of nose drops containing the vaccine strain at a suitable dose while the individual is lying prone with head turned back. Alternatively, intranasal immunization can be achieved by aerosolization into the nostrils with a nebulizer. The dose administered is determined by the number of squirts.

Other routes of administration can also be tested. For example, rectal immunization can be achieved by the procedures described by Nardelli-Haefliger et al. (Infect Immun, 1996). Intraconjunctival immunization can be achieved by administration of eye drops. All of the monitoring and well being of immunized subjects and for the elicitation of appropriate immune responses are as described in Example 16.

EXAMPLE 18

This example illustrates methods for preparation of RpoS⁺ *Salmonella, Shigella/Escherichia* and *Salmonella/Escherichia* hybrids for use in delivering DNA vaccine vectors to a human.

Circular plasmid DNA encoding antigens of various pathogens can be introduced into animal hosts to stimulate the induction of immunity to the pathogen from which the antigen gene was derived (Ullmer et al., *ASM News* 62:476–479, 1996; Ullmer et al., *Curr. Opin. Immunol*

8:531–536, 1996; Whalen, *Emerg. Infect. Dis.* 2:168–175, 1996; Robinson, *Vaccine* 15:785–787, 1997). DNA vaccines make use of expression systems such that the genetic information specifying the antigen of some pathogen is expressed by the immunized hosts using host machinery for transcription and translation. Initially, DNA vaccines were administered by injection into muscle tissue, but other injection sites have also been used. Most recently, DNA vaccines have been administered using particle guns to accelerate entry of DNA-coated gold beads into skin or mucosal tissues. The DNA vaccine vbectors are propagated in and isolated from recombinant *E. coli* strains grown in fermentors.

Sizemore et al. (*Science,* 270:299–302, 1995; *Vaccine* 15:804–807, 1997) described the use of *Shigella flexneri* 2a strain 15D with a Δasd mutation that harbored a DNA vaccine vector engineered to express *E. coli* β-galactosidase. The *Shigella* strain was attenuated due to the Δasd mutation which causes death due to absence of diaminopimelic acid upon invasion into eukaryotic cells. The strain was able to deliver the DNA vaccine vector intracellularly after attachment to, invasion into and lysis within the cytoplasm of eukaryotic cells in culture or within immunized mice. More recently, others have used *S. typhimurium* strains possessing a DNA vaccine vector and caused to lyse by spontaneous means (Powell et al., WO96/34631, 1996; Pasenal et al., *Behring. Inst. Mitt.* 98:143–152, 1997; Darji et al., *Cell* 91:765–775, 1997). In cases in which lysis was spontaneous, it was necessary that the bacterial strain possess one or more deletion mutations rendering the strain attenuated. *Shigella, Salmonella* and invasive *E. coli* are known to have a much enhanced ability to attach to and invade M cells overlying the GALT rather than to attach to and invade intestinal epithelial cells (enterocytes). Delivery of foreign antigens or the production of foreign antigens within the NALT, BALT, CALT and GALT which all have an M cell layer leads to induction of mucosal immune responses as well as systemic immunity. Because mucosal immune responses are protective against the vast majority of infectious disease agents that colonize on or invade through a mucosal surface, it would be expected that DNA vaccine vectors could thus be delivered by RpoS$^+$ *Salmonella, Shigella, Escherichia* or hybrids between any two of these genera. These microbes would have a superior ability to attach to and invade the M cells overlying the lymphoid tissues of the NALT, CALT, BALT and GALT. Because both oral and intranasal immunization with RpoS$^+$ microbes increase the immune response, it would be expected that attenuated bacterial DNA vaccine vector strains displaying an RpoS$^+$ phenotype will give an increased immune response when administered intranasally or perorally and presumably by other routes that stimulate mucosal immune responses.

We have used derivatives of the DNA vaccine vector pCMVβ to express foreign antigens. pCMVβ possesses the pUC origin of replication for propagation in *E. coli,* a β-lactamase gene to confer resistance to ampicillin, promoters and enhancers from CMV and SV40 viruses and an SV40 sequence to achieve polyadenylation of the transcribed mRNA (MacGregor et al., *Nucleic Acid Res.* 17:1265, 1989). pCMVβ contains the coding sequence for *E. coli* β-galactosidase which has been used as a test antigen in several studies. The lacZ gene encoding β-galactosidase can be easily removed with substitution of DNA encoding a diversity of antigens, especially from viral, fungal and parasitic pathogens. Since introducing antibiotic resistance genes as parts of vaccines into immunized animal and human hosts continues to be a concern, we have substituted the *S. typhimurium* asd gene for the ampicillin-resistance gene in pCMVβ to yield pCMVβ-asd (FIG. 16). This enables the use of an *E. coli* host that has a Δasd mutation to yield a balanced-lethal host-vector system that can be propagated in the fermentor in the absence of added costly antibiotics that could also potentially contaminate the purified DNA vaccine vector. Furthermore, the *S. typhimurium* asd gene possesses two natural CpG sequences (Kreig, *J. Lab. Clin. Med* 128:128–133, 1996) that strongly enhance the immunogenicity of the DNA vaccine vector. Such sequences are absent in the kanamycin-resistance gene that is now often used in lieu of the ampicillin-resistance gene in DNA vaccines. The use of the *S. typhimurium* asd gene in such DNA vaccine vectors is described in U.S. Pat. No. 5,840,483.

Further refinement of this technology to improve efficacy would be to have the attenuated bacteria release into the cytoplasm of antigen presenting cells within the immunized individual, mRNA copies of genes present in the DNA vaccine vector so that the mRNA would be directly translated into a protein product within the cytoplasm of the immunized host's cells. This could greatly enhance the efficiency of vaccine delivery since with traditional delivery of DNA vaccines, the DNA vaccine vector must migrate to the nucleus to permit transcription which even then might not occur in all cells, and then have the mRNA transit to the cytoplasm for translation into a protein product to stimulate an immune response. Since RpoS$^+$ strains are more efficient than RpoS$^-$ strain in antigen delivery, it is expected that they would also be more efficient in delivery of nucleic acid, either DNA or RNA.

Commercial Utility:

The bacterial strains provided herein are directly and indirectly suitable for production of immunogenic compositions, including vaccines, to prevent diseases caused by various bacterial, viral, fungal protazoal pathogens. These carrier bacterial strains which can be, for example, *S. typhi* strains or other Enterobacteriaceae, all have an RpoS$^+$ phenotype, and can serve as carriers for delivering to target tissues, heterologous proteins or nucleic acid molecules for expression of gene products. Examples of gene products deliverable by the microbes of the invention include but are not limited to: antigens, which can be from a human pathogen, or, for use in autoimmune applications, from the human itself, such as, for example, a gamete-specific antigen; enzymes that can synthesize antigens such as polysaccharides, lipoproteins, glycoproteins, and glycolipids; allergens of the human; immunoregulatory molecules; hormones; and pharmacologically active polypeptides. The microbes are not only attenuated, but also show high immunogenicity because of an improved ability to colonize lymphoid tissue compared to previously used recombinant attenuated bacteria. The present strains are useful as carrier microorganisms for the production of expression products encoded on recombinant genes in the bacterial cells. In addition, the strains which can be used with enhanced safety and improved immunogenicity are highly effective in the production of antibodies against recombinant antigens which can be expressed in the attenuated, immunogenic bacteria.

Deposit:

The following strains and plasmid are on deposit under the terms of the Budapest Treaty, with the American Type Culture Collection, 10801 University Boulevard, Manassas, Va. The accession number indicated was assigned after successful viability testing, and the requisite fees were paid.

Access to the cultures and plasmid will be available during pendency of the patent application to one determined by the Commissioner to be entitled thereto under 37 CFR 1.14 and 35 USC 122. All restriction on availability of the cultures and plasmid to the public will be irrevocably removed upon the granting of a patent based upon the application. Moreover, the designated deposits will be maintained for a period of thirty (30) years from the date of deposit, or for five (5) years after the last request for the deposit, or for the enforceable life of the U.S. patent, whichever is longer. Should a culture or plasmid become nonviable or be inadvertently destroyed, or, in the case of plasmid-containing strains, lose its plasmid, it will be replaced with a viable culture. The deposited materials mentioned herein are intended for convenience only, and are not required to practice the present invention in view of the description herein, and in addition, these materials are incorporated herein by reference.

| Deposit | Deposit Date | ATCC No. |
|---|---|---|
| Strains: | | |
| MGN-1191 | Nov. 14, 1997 | 202054 |
| MGN-1256 | Nov. 14, 1997 | 202053 |
| χ8280 | Nov. 14, 1997 | 202055 |
| χ8281 | Nov. 14, 1997 | 202056 |
| χ8438 | Nov. 18, 1998 | 202182 |
| Plasmid: | | |
| pYA3433 | Nov. 14, 1997 | 209462 |

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method for producing a carrier bacterium for delivery of a desired gene product to a host, comprising the steps of:
   (a) converting a rpoS-bacterium to a rpoS+ bacterium by introducing a recombiumt rpoS+ gene;
   (b) introducing one or more inactivating mutations which render said carrier bacterium attenuated; and
   (c) introducing a second recombinant gene encoding the desired gene product to a bacterium, wherein steps (a), (b), or (c) may be performed in any order.

2. The method according to claim 1 wherein the bacterium is a strain of Salmonella.

3. The method according to claim 2 wherein the strain of Salmonella is a strain of S. typhi.

4. The method according to claim 1 wherein the second recombinant gene encodes a gene product from a pathogen to said host.

5. A method for delivery of a desired gene product to a host with a carrier bacterium, the method comprising:
   (a) converting a rpoS− bacterium to a rpoS+ bacterium by introducing a recombinant rpoS+ gene;
   (b) introducing one or more inactivating mutations in a bacterium which render the bacterium attenuated;
   (c) introducing a second recombinant gene encoding the desired gene product to a bacterium, wherein steps (a), (b), or (c) may be performed in any order to yield said carrier bacterium; and
   (d) administering to the host said carrier bacterium.

6. The method of claim 5 wherein the bacterium is a strain of Salmonella.

7. The method of claim 6 wherein the strain of Salmonella is a strain of S. typhi.

8. The method of claim 5 wherein the recombinant gene encodes a product from a pathogen to said host.

9. A method for delivery of a desired gene product to a host, said method comprising
   (a) selecting for a strain of bacteria having (i) an RpoS+ phenotype, (ii) one or more inactivating mutations which render the strain attenuated, and (iii) a recombinant gene encoding the desired gene product; and
   (b) administering the strain to the host.

10. The method of claim 9 wherein the strain of bacteria is a strain of Salmonella.

11. The method of claim 10 wherein the strain of Salmonella is a strain of S. typhi.

12. The method of claim 9 wherein the recombinant gene encodes a gene product from a pathogen to said host.

13. The method of claim 9 wherein the one or more inactivating mutations are in a gene selected from the group consisting of a pab gene, a pur gene, an aro gene, asd, a dap gene, nadA, pncB, galE, pmi, fur, rpsL, ompR, htrA, hemA, cdt, cya, crp, dam, phoP, phoQ, rfc, poxA, galU, metL, metH, mviA, sodC, recA, ssrA, ssrB, sirA, sirB, sirC, inv, hilA, hilC, hilD, rpoE, flgM, tonB, and slyA.

14. A method for producing from a parent bacteria strain, a carrier bacteria for the delivery of a desired gene product to a host, said method comprising generating a strain of bacteria having (a) a recombinant rpoS+ gene (b) one or more inactivating mutations which render said bacteria attenuated and (c) a second recombinant gene encoding the desired gene product, wherein said carrier bacteria expresses a higher level of RpoS gene product than said parent bacteria strain and wherein said higher level of RpoS gene product confers upon the carrier bacteria high immunogenicity relative to said parent bacteria strain.

15. The method according to claim 14 wherein the bacteria is a strain of Salmonella.

16. The method according to claim 15 wherein the Salmonella is a strain of S. typhi.

17. The method of claim 14 wherein the one or more inactivating mutations are in a gene selected from the group consisting of a pab gene, a pur gene, an aro gene, asd, a dap gene, nadA, pncB, galE, pmi, fur, rspL, ompR, htrA, hemA, cdt, cya, crp, dam, phoP, phoQ, rfc, poxA, galU, metL, metH, mviA, sodC, recA, ssrA, ssrB, sirA, sirB, sirC, inv, hilA, hilC, hilD, rpoE, flgM, tonB, and slyA.

18. The method according to claim 17 wherein the second recombinant gene encodes a gene product from a pathogen to said host.

19. The method according to claim 18 wherein the pathogen is a virus, bacterium, protozoan, parasite or fungus.

20. A method for producing a carrier bacteria for delivery of a desired gene product to a host, said method comprising selecting for a strain of bacteria having
   (a) an RpoS+ phenotype;
   (b) one or more inactivating mutations which render the strain attenuated; and
   (c) a recombinant gene encoding the desired gene product.

21. The method of claim 9 wherein the recombinant gene encodes an immunoregulatory molecule, allergen, or autoantigen.

22. The method of claim 21, wherein the immunoregulatory molecule is selected from the group consisting of IL-2, IL-4, IL-5, IL-6, MIF, IFN-γ, TNF-α and TGF-β.

23. The method of claim 21, wherein the auto-antigen is ZP-3.

24. The method of claim 14 wherein the second recombinant gene encodes a immunoregulatory molecule, allergen, or auto-antigen.

25. The method of claim 24, wherein the immunoregulatory molecule is selected from the group consisting of IL-2, IL-4, IL-5, IL-6, MIF, IFN-γ, TNF-α and TGF-β.

26. The method of claim 24, wherein the auto-antigen is ZP-3.

27. The method of claim 20 wherein the recombinant gene encodes a immunoregulatory molecule, allergen, or auto-antigen.

28. The method of claim 27, wherein the immunoregulaory molecule is selected from the group consisting of IL-2, IL-4, IL-5, IL-6, MIF, IFN-γ, TNF-α and TGF-β.

29. The method of claim 27, wherein the auto-antigen is ZP-3.

* * * * *